United States Patent
Bouche et al.

(10) Patent No.: US 12,421,209 B2
(45) Date of Patent: Sep. 23, 2025

(54) COMPOUNDS

(71) Applicant: Hoffmann-La Roche Inc., Little Falls, NJ (US)

(72) Inventors: Lea Aurelie Bouche, Basel (CH); Wolfgang Guba, Müllheim (DE); Georg Jaeschke, Basel (CH); Stefanie Katharina Mesch, Basel (CH); Angelique Patiny-Adam, Kembs (FR); Christian Schnider, Biel-Benken (CH); Sandra Steiner, Sursee (CH); Andreas Michael Tosstorff, Basel (CH)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 19/063,141

(22) Filed: Feb. 25, 2025

(65) Prior Publication Data
US 2025/0197370 A1     Jun. 19, 2025

Related U.S. Application Data

(63) Continuation of application No. 18/524,678, filed on Nov. 30, 2023, which is a continuation of application No. PCT/EP2022/064995, filed on Jun. 2, 2022.

(30) Foreign Application Priority Data

| Jun. 4, 2021 | (EP) | ................................. 21177660 |
| Jul. 30, 2021 | (EP) | ................................. 21188639 |
| Dec. 20, 2021 | (EP) | ................................. 21215875 |

(51) Int. Cl.
| C07D 401/12 | (2006.01) |
| C07D 253/07 | (2006.01) |
| C07D 405/14 | (2006.01) |
| C07D 471/04 | (2006.01) |

(52) U.S. Cl.
CPC ......... *C07D 401/12* (2013.01); *C07D 253/07* (2013.01); *C07D 405/14* (2013.01); *C07D 471/04* (2013.01)

(58) Field of Classification Search
CPC .............. C07D 401/12; C07D 253/07; C07D 405/14; C07D 471/04
See application file for complete search history.

(56) References Cited

FOREIGN PATENT DOCUMENTS

| CN | 11562172 | * 12/2020 | ........... C07D 237/14 |
| WO | 2019/034690 A1 | 2/2019 | |
| WO | 2019/092170 A1 | 5/2019 | |
| WO | 2020/021447 | 1/2020 | |
| WO | 2020/163248 A1 | 8/2020 | |
| WO | 2020/234715 A1 | 11/2020 | |
| WO | 2021/150574 A1 | 7/2021 | |
| WO | 2021/193897 A1 | 9/2021 | |
| WO | 2022/135567 A1 | 6/2022 | |
| WO | 2022/166890 A1 | 8/2022 | |
| WO | 2022/216971 | 10/2022 | |
| WO | 2022/230912 A1 | 11/2022 | |
| WO | 2022/253326 A1 | 12/2022 | |
| WO | 2023/275366 A1 | 1/2023 | |
| WO | 2023/028536 A1 | 3/2023 | |
| WO | 2023/066377 A1 | 4/2023 | |
| WO | 2023/131277 A1 | 7/2023 | |
| WO | 2023/183943 A1 | 9/2023 | |
| WO | 2024/090469 A1 | 2/2024 | |
| WO | 2024/141535 A1 | 4/2024 | |
| WO | 2024/169858 A1 | 8/2024 | |
| WO | 2024/094185 A1 | 10/2024 | |

OTHER PUBLICATIONS

Baldwin, A., et al., "Inhibiting the Inflammasome: A Chemical Perspective" ACS J Med Chem 59(5):1691-1710 (Sep. 30, 2015).
Cocco, M., et al.,"Electrophilic Warhead-Based Design of Compounds Preventing NLRP3 Inflammasome-Dependent Pyroptosis" ACS J Med Chem 57(24):10366-10382 (Nov. 24, 2014).
"International Preliminary Report on Patentability—PCT/EP2022/064995" (Report Issuance Date: Nov. 21, 2023; Chapter I),:pp. 1-8 (Dec. 14, 2023).
"International Search Report—PCT/EP2022/064995" (w/Written Opinion),:pp. 1-13 (Aug. 31, 2022).
Kakusawa, N., et al., "Reaction of 1,2,4-Triazine 1-Oxides with Benzyne: Formation of 1,3-Benzoxazepine and 1,3,5,6-Benzoxatriazonine Derivatives" Heterocycles—JPN 43(10):2091-2094 (Oct. 1, 1996).
Liu, Y., et al., "NLRP3 inflammasome activation mediates radiation-induced pyroptosis in bone marrow-derived macrophages" Cell Death Dis 8(2):e2579 (1-9) (Feb. 2, 2017).
Menu, P., et al., "The NLRP3 inflammasome in health and disease: the good, the bad and the ugly" Clin Exp Immunol 166(1):1-15 (Jul. 15, 2011).
Ozaki, E., et al., "Targeting the NLRP3 inflammasome in chronic inflammatory diseases: current perspectives" J Inflamm Res 8:15-27 (Jan. 16, 2015).
Satoh, T., et al., "NLRP3 activation induces ASC-dependent programmed necrotic cell death, which leads to neutrophilic inflammation" Cell Death Dis 4(5):e644 (1-10) (May 23, 2013).

(Continued)

*Primary Examiner* — Joseph K McKane
*Assistant Examiner* — David M Shim
(74) *Attorney, Agent, or Firm* — Daniel Shelton

(57) ABSTRACT

The invention relates to novel compounds having the general formula Ib

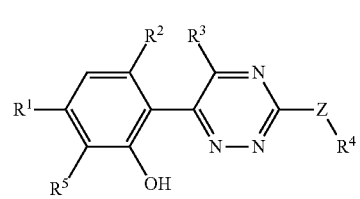

wherein $R^1$, $R^2$, $R^3$, $R^4$, $R^5$ and Z are as described herein, composition including the compounds and methods of using the compounds.

2 Claims, 1 Drawing Sheet

(56) References Cited

OTHER PUBLICATIONS

Strowig, T., et al., "Inflammasomes in health and disease" Nature 481(7381):278-286 (Jan. 18, 2012).
Wree, A., et al., "NLRP3 inflammasome activation results in hepatocyte pyroptosis, liver inflammation and fibrosis" Hepatology 59(3):898-910 (Jan. 30, 2014).
Xie, Z., et al., "Pyroptosis and neurological diseases" Neuroimmunol Neuroinflamm 1(2):60-65 (Apr. 30, 2014).

* cited by examiner

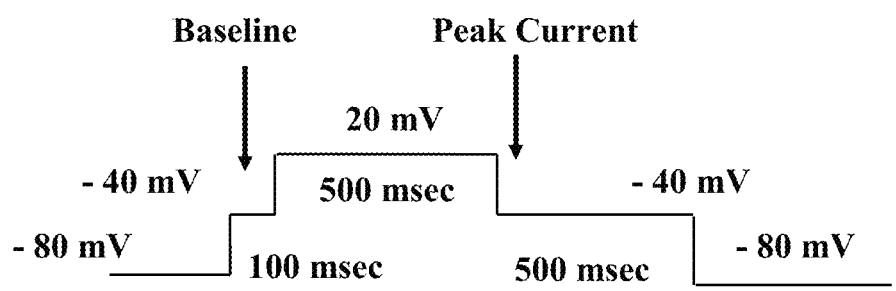

COMPOUNDS

CROSS-REFERENCE TO RELATED APPLICATIONS

This application is a Continuation of U.S. application Ser. No. 18/524,678, filed Nov. 30, 2023, which is a Continuation of International Application No. PCT/EP2022/064995, filed Jun. 2, 2022, which claims benefit of priority to European Application Nos. 21177660.4 filed Jun. 4, 2021, 21188639.5 filed on Jul. 30, 2021, and 21215875.2 filed Dec. 20, 2021, each of which is incorporated herein by reference in its entirety.

FIELD OF THE INVENTION

The present invention relates to organic compounds useful for therapy and/or prophylaxis in a mammal, and in particular to compounds that modulate NLRP3 inhibition.

The present invention provides novel compounds of formula Ib

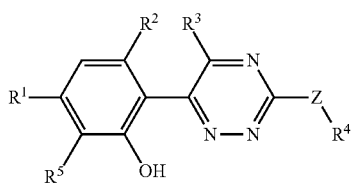

wherein
$R^1$ is H, halo, alkyl, haloalkyl, haloalkoxy or nitrile;
$R^5$ is H;
or $R^1$ and $R^5$, and the atoms to which they are bonded, form either a 4-6 membered heterocycle ring comprising a single O heteroatom optionally substituted with one or two substituents independently selected from halo or alkyl, or $R^1$ and $R^5$, and the atoms to which they are bonded, form a 3-6 membered cycloalkyl ring optionally substituted with one or two substituents independently selected from halo or alkyl;
$R^2$ is H, halo, alkyl, haloalkyl, cycloalkyl, or cycloalkylalkyl, wherein cycloalkyl or cycloalkylalkyl is optionally substituted with halo or haloalkoxy;
$R^3$ is H, alkyl, haloalkyl, or cycloalkyl optionally substituted with halo;
Z is —O—, —NH—, or —NHCH$_2$—;
$R^4$ is a heterocycle ring optionally substituted with 1 to 2 substituents independently selected from halo, alkyl, haloalkyl, hydroxyalkyl, —OH, oxo, —CO$_2$H, or cycloalkyl optionally substituted with halo; or
$R^4$ is a cycloalkyl optionally substituted with 1 to 3 substituents independently selected from alkyl, halo, haloalkyl and —OH;
and pharmaceutically acceptable salts.

Furthermore, the invention includes all racemic mixtures, all their corresponding enantiomers and/or optical isomers.

BACKGROUND OF THE INVENTION

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signaling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1β and pro-IL-18 respectively) to thereby activate these cytokines. Caspase-1 also mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NO-MID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using Nlrp3$^{-/-}$ mice, but there have also been insights into the specific activation of NLRP3 in these diseases. In type 2 diabetes mellitus (T2D), the deposition of islet amyloid polypeptide in the pancreas activates NLRP3 and IL-1β signalling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-β-nitrostyrene and dimethyl sulfoxide (DMSO), although these agents have limited potency and are nonspecific.

Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

There is a need to provide compounds with improved pharmacological and/or physiological and/or physicochemical properties and/or those that provide a useful alternative to known compounds.

SUMMARY OF THE INVENTION

The present invention provides novel compounds of formula Ib:

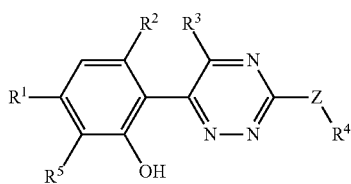

wherein
$R^1$ is H, halo, alkyl, haloalkyl, haloalkoxy or nitrile;
$R^5$ is H;
or $R^1$ and $R^5$, and the atoms to which they are bonded, form either a 4-6 membered heterocycle ring comprising a single O heteroatom optionally substituted with one or two substituents independently selected from halo or alkyl, or $R^1$ and $R^5$, and the atoms to which they are bonded, form a 3-6 membered cycloalkyl ring optionally substituted with one or two substituents independently selected from halo or alkyl;
$R^2$ is H, halo, alkyl, haloalkyl, cycloalkyl, or cycloalkylalkyl, wherein cycloalkyl or cycloalkylalkyl is optionally substituted with halo or haloalkoxy;
$R^3$ is H, alkyl, haloalkyl, or cycloalkyl optionally substituted with halo;
Z is —O—, —NH—, or —NHCH$_2$—;
$R^4$ is a heterocycle ring optionally substituted with 1 to 2 substituents independently selected from halo, alkyl, haloalkyl, hydroxyalkyl, —OH, oxo, —CO$_2$H, or cycloalkyl optionally substituted with halo; or
$R^4$ is a cycloalkyl optionally substituted with 1 to 3 substituents independently selected from alkyl, halo, haloalkyl and —OH;
and pharmaceutically acceptable salts.

The term "alkyl" denotes a monovalent linear or branched saturated hydrocarbon group of 1 to 6 carbon atoms. In some embodiments, if not otherwise described, alkyl comprises 1 to 6 carbon atoms ($C_{1-6}$-alkyl), or 1 to 4 carbon atoms ($C_{1-4}$-alkyl). Examples of $C_{1-6}$-alkyl include methyl, ethyl, propyl, isopropyl, n-butyl, iso-butyl, sec-butyl, tert-butyl and pentyl. Particular alkyl groups include methyl and ethyl. When an alkyl residue having a specific number of carbons is named, all geometric isomers having that number of carbons may be encompassed. Thus, for example, "butyl" can include n-butyl, sec-butyl, isobutyl and t-butyl, and "propyl" can include n-propyl and isopropyl.

The term "alkoxy" denotes a group of the formula —O—R', wherein R' is a $C_{1-6}$-alkyl group. Examples of $C_{1-6}$-alkoxy groups include methoxy, ethoxy, n-propoxy, isopropoxy, n-butoxy, isobutoxy and tert-butoxy. Particular examples are methoxy and ethoxy.

The term "cycloalkyl" denotes monocyclic or polycyclic saturated or partially unsaturated, non-aromatic hydrocarbon. In some embodiments, unless otherwise described, cycloalkyl comprises 3 to 8 carbon atoms, 3 to 6 carbon atoms, or 3 to 5 carbon atoms. In some embodiments, cycloalkyl is a saturated monocyclic or polycyclic hydrocarbon. In other embodiments, cycloalkyl comprises one or more double bonds (e.g., cycloalkyl fused to an aryl or heteroaryl ring, or a non-aromatic monocyclic hydrocarbon comprising one or two double bonds). Examples of cycloalkyl groups include cyclopropyl, cyclobutyl, cyclopentyl, cyclohexyl, octahydropentalenyl, spiro[3.3]heptanyl, and the like. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Particular examples are cyclopropyl, cyclobutyl and cyclohexyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, and hydroxycylopropylmethyl.

The term "halogen", "halide" and "halo" are used interchangeably herein and denote fluoro, chloro, bromo or iodo. Particular halogens are fluoro and chloro.

The term "haloalkyl" denotes a $C_{1-6}$-alkyl group wherein at least one of the hydrogen atoms of the $C_{1-6}$-alkyl group has been replaced by the same or different halogen atoms. Particular examples are fluoromethyl, difluoromethyl and trifluoromethyl.

The term "haloalkoxy" denotes a $C_{1-6}$-alkoxy group wherein at least one of the hydrogen atoms of the $C_{1-6}$-alkoxy group has been replaced by the same or different halogen atoms. Examples of haloalkoxy are difluoromethoxy, trifluoromethoxy, difluoroethoxy and trifluoroethoxy. Particular example is trifluoromethoxy.

The term "heterocycle" denotes a monovalent saturated or partly unsaturated mono- or bicyclic ring system of 4 to 10 ring atoms, or 4 to 9 ring atoms, comprising 1, 2, or 3 ring heteroatoms selected from N, O and S, the remaining ring atoms being carbon. Examples for monocyclic saturated heterocycle rings are oxetanyl, azetidinyl, pyrrolidinyl, tetrahydrofuranyl, pyrazolidinyl, imidazolidinyl, oxazolidinyl, isoxazolidinyl, thiazolidinyl, piperidinyl, tetrahydropyranyl, tetrahydrothiopyranyl, or piperazinyl. Examples for partly unsaturated heterocycle rings are dihydrofuryl, imidazolinyl, dihydro-oxazolyl, tetrahydro-pyridinyl, or dihydropyranyl. Particular examples of a heterocycle ring are piperidinyl, furanyl, 5,6,7,8-tetrahydroimidazo[1,2-a]pyridin-8-yl, and 1,2,3,5,6,7,8,8a-octahydroindolizin-8-yl.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl.

The term "nitrile" denotes a —C≡N group.

The term "pharmaceutically acceptable salts" refers to those salts which retain the biological effectiveness and properties of the free bases or free acids, which are not biologically or otherwise undesirable. The salts are formed with inorganic acids such as trifluoroacetic acid, hydrochloric acid, hydrobromic acid, sulfuric acid, nitric acid, phosphoric acid, particularly hydrochloric acid, and organic acids such as formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared from addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula Ib can also be present in the form of zwitterions. Particularly preferred pharmaceutically acceptable salts of compounds of formula Ib are the salts formed with formic acid and the salts formed with hydrochloric acid yielding a hydrochloride, dihydrochloride or trihydrochloride salt.

The abbreviation uM means microMolar and is equivalent to the symbol µM.

The abbreviation uL means microliter and is equivalent to the symbol µL.

The abbreviation ug means microgram and is equivalent to the symbol µg.

The compounds of formula Ib can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention provides compounds according to formula Ib as described herein and pharmaceutically acceptable salts or esters thereof, in particular compounds according to formula Ib as described herein and pharmaceutically acceptable salts thereof, more particularly compounds according to formula Ib as described herein.

An embodiment of the present invention provides compounds according to formula Ib as described herein, wherein
$R^1$ is halo, haloalkyl, haloalkoxy or nitrile;
$R^5$ is H;
or $R^1$ and $R^5$, and the atoms to which they are bonded, form either
a 5 membered heterocycle ring comprising a single O heteroatom, or
$R^1$ and $R^5$, and the atoms to which they are bonded, form a 4-5 membered cycloalkyl ring.

An embodiment of the present invention provides compounds according to formula Ib as described herein, wherein
$R^1$ is haloalkyl or haloalkoxy;
$R^5$ is H;
or $R^1$ and $R^5$, and the atoms to which they are bonded, form either
a 5 membered heterocycle ring comprising a single O heteroatom, or
$R^1$ and $R^5$, and the atoms to which they are bonded, form a 4-5 membered cycloalkyl ring.

An embodiment of the present invention provides compounds according to formula Ib as described herein, wherein
$R^1$ is haloalkyl;
$R^5$ is H;
or $R^1$ and $R^5$, and the atoms to which they are bonded, form either
a 5 membered heterocycle ring comprising a single O heteroatom, or
$R^1$ and $R^5$, and the atoms to which they are bonded, form a 4 membered cycloalkyl ring.

An embodiment of the present invention provides compounds according to formula Ib as described herein, wherein $R^1$ is H, halo, alkyl, haloalkyl, or haloalkoxy.

An embodiment of the present invention provides compounds according to formula Ib as described herein, wherein $R^1$ is halo or haloalkyl.

An embodiment of the present invention provides compounds according to formula Ib as described herein, wherein $R^1$ is F, Cl, $OCF_3$, $CF_3$, or $CH_3$.

An embodiment of the present invention provides compounds according to formula Ib as described herein, wherein $R^1$ is $CF_3$.

An embodiment of the present invention provides compounds according to formula Ib as described herein, where $R^2$ is H, halo, alkyl, haloalkyl, cycloalkyl, or cycloalkylalkyl, wherein cycloalkyl or cycloalkylalkyl is optionally substituted with halo;

An embodiment of the present invention provides compounds according to formula Ib as described herein, where $R^2$ is H, halo, alkyl, haloalkyl, or cycloalkyl, wherein cycloalkyl or cycloalkylalkyl is optionally substituted with halo;

An embodiment of the present invention provides compounds according to formula Ib as described herein, wherein $R^2$ is H, halo, alkyl or haloalkyl.

An embodiment of the present invention provides compounds according to formula Ib as described herein, wherein $R^2$ is H, halo, or alkyl.

An embodiment of the present invention provides compounds according to formula Ib as described herein, wherein $R^2$ is H or alkyl.

An embodiment of the present invention provides compounds according to formula Ib as described herein, wherein $R^2$ is alkyl.

An embodiment of the present invention provides compounds according to formula Ib as described herein, wherein $R^2$ is H.

An embodiment of the present invention provides compounds according to formula Ib as described herein, wherein $R^3$ is H, alkyl or haloalkyl.

An embodiment of the present invention provides compounds according to formula Ib as described herein, wherein $R^3$ is H or alkyl.

An embodiment of the present invention provides compounds according to formula Ib as described herein, wherein $R^3$ is H.

An embodiment of the present invention provides compounds according to formula Ib as described herein, wherein $R^3$ is alkyl.

An embodiment of the present invention provides compounds according to formula Ib as described herein, wherein $R^3$ is methyl.

An embodiment of the present invention provides compounds according to formula Ib as described herein, wherein $R^4$ is
- a 6-to-9-membered heterocycle ring comprising a 1 or 2 N heteroatom; or
- a 6-membered heterocycle ring comprising 1 N heteroatom, substituted with 1 to 2 substituents independently selected from alkyl and —OH; or
- a 4-to-6 membered cycloalkyl substituted with 1 to 2 substituents independently selected from alkyl and —OH—.

An embodiment of the present invention provides compounds according to formula Ib as described herein, wherein $R^4$ is
- a 9-membered heterocycle ring comprising a single N heteroatom; or
- a 6-membered heterocycle ring comprising 1 N heteroatom, substituted with 1 alkyl substituent.

An embodiment of the present invention provides compounds according to formula Ib as described herein, wherein $R^4$ is methylpiperidyl or ethylpiperidyl.

An embodiment of the present invention provides compounds according to formula Ib as described herein, wherein $R^4$ is a heterocycle ring optionally substituted with alkyl, or a cycloalkyl ring optionally substituted with 1 to 2 substituents selected from alkyl and —OH.

An embodiment of the present invention provides compounds according to formula Ib as described herein, wherein $R^4$ is a heterocycle ring optionally substituted with alkyl.

An embodiment of the present invention provides compounds according to formula Ib as described herein, wherein $R^4$ is a heterocycle ring comprising 1 heteroatom substituted with alkyl.

An embodiment of the present invention provides compounds according to formula Ib as described herein, wherein $R^4$ is either ethylpiperidine or cyclobutane substituted with alkyl and —OH.

An embodiment of the present invention provides compounds according to formula Ib as described herein, wherein $R^4$ is ethylpiperidine.

An embodiment of the present invention provides compounds according to formula Ib as described herein, wherein Z is —O— or —NH—.

An embodiment of the present invention provides compounds according to formula Ib as described herein, wherein Z is —NH—.

An embodiment of the present invention provides compounds according to formula Ib as described herein, wherein $R^1$ and $R^5$, and the atoms to which they are bonded, form either a 4-6 membered heterocycle ring comprising a single O heteroatom optionally substituted with one or two substituents independently selected from halo or alkyl, or $R^1$ and $R^5$, and the atoms to which they are bonded, form a 3-6 membered cycloalkyl ring optionally substituted with one or two substituents independently selected from halo or alkyl.

An embodiment of the present invention provides compounds according to formula Ib as described herein, wherein $R^1$ and $R^5$, and the atoms to which they are bonded, form either a 4-6 membered heterocycle ring comprising a single O heteroatom, or $R^1$ and $R^5$, and the atoms to which they are bonded, form a 3-6 membered cycloalkyl ring.

An embodiment of the present invention provides compounds according to formula Ib as described herein, wherein $R^1$ and $R^5$, and the atoms to which they are bonded, form a 5 membered heterocycle ring comprising a single O heteroatom.

An embodiment of the present invention provides compounds according to formula Ib as described herein, wherein
- $R^1$ is halo, haloalkyl, haloalkoxy or nitrile;
- $R^5$ is H;
- or $R^1$ and $R^5$, and the atoms to which they are bonded, form either
  - a 5 membered heterocycle ring comprising a single O heteroatom, or
  - $R^1$ and $R^5$, and the atoms to which they are bonded, form a 4-5 membered cycloalkyl ring;
- $R^2$ is H, halo, or alkyl;
- $R^3$ is H, alkyl or haloalkyl;
- Z is-NH—;
- $R^4$ is
  - a 6-to-9-membered heterocycle ring comprising a 1 or 2 N heteroatom; or
  - a 6-membered heterocycle ring comprising 1 N heteroatom, substituted with 1 to 2 substituents independently selected from alkyl and —OH; or
  - a 4-to-6 membered cycloalkyl substituted with 1 to 2 substituents independently selected from alkyl and —OH—;
- and pharmaceutically acceptable salts thereof.

An embodiment of the present invention provides compounds according to formula Ib as described herein, wherein
- $R^1$ is halo, haloalkyl, haloalkoxy or nitrile;
- $R^5$ is H;
- or $R^1$ and $R^5$, and the atoms to which they are bonded, form either
  - a 5 membered heterocycle ring comprising a single O heteroatom, or
  - $R^1$ and $R^5$, and the atoms to which they are bonded, form a 4-5 membered cycloalkyl ring;
- $R^2$ is H;
- $R^3$ is alkyl;
- Z is-NH—;
- $R^4$ is
  - a 9-membered heterocycle ring comprising a single N heteroatom; or
  - a 6-membered heterocycle ring comprising 1 N heteroatom, substituted with 1 alkyl substituent;
- and pharmaceutically acceptable salts thereof.

An embodiment of the present invention provides compounds according to formula Ib as described herein, wherein
- $R^1$ is haloalkyl or haloalkoxy;
- $R^5$ is H;
- or $R^1$ and $R^5$, and the atoms to which they are bonded, form either
  - a 5 membered heterocycle ring comprising a single O heteroatom, or
  - $R^1$ and $R^5$, and the atoms to which they are bonded, form a 4-5 membered cycloalkyl ring;
- $R^2$ is H;
- $R^3$ is alkyl;
- Z is —NH—;
- $R^4$ is methylpiperidyl or ethylpiperidyl;
- and pharmaceutically acceptable salts thereof.

An embodiment of the present invention provides compounds according to formula Ib as described herein, wherein
- $R^1$ is haloalkyl;
- $R^5$ is H;
- or $R^1$ and $R^5$, and the atoms to which they are bonded, form either
  - a 5 membered heterocycle ring comprising a single O heteroatom, or
  - $R^1$ and $R^5$, and the atoms to which they are bonded, form a 4 membered cycloalkyl ring;

$R^2$ is H;
$R^3$ is alkyl;
Z is -NH-;
$R^4$ is ethylpiperidyl;
and pharmaceutically acceptable salts thereof.

An embodiment of the present invention provides compounds according to formula Ib as described herein, wherein
$R^1$ and $R^5$, and the atoms to which they are bonded, form either a 4-6 membered heterocycle ring comprising a single O heteroatom optionally substituted with one or two substituents independently selected from halo or alkyl, or $R^1$ and $R^5$, and the atoms to which they are bonded, form a 3-6 membered cycloalkyl ring optionally substituted with one or two substituents independently selected from halo or alkyl;
$R^2$ is H;
$R^3$ is methyl;
Z is -NH-;
$R^4$ is a piperidine ring substituted with alkyl;
and pharmaceutically acceptable salts thereof.

An embodiment of the present invention provides compounds according to formula Ib as described herein, wherein
$R^1$ and $R^5$, and the atoms to which they are bonded, form either a 4-6 membered heterocycle ring comprising a single O heteroatom, or $R^1$ and $R^5$, and the atoms to which they are bonded, form a 3-6 membered cycloalkyl ring:
$R^2$ is H;
$R^3$ is methyl;
Z is -NH-;
$R^4$ is a piperidine ring substituted with alkyl;
and pharmaceutically acceptable salts thereof.

An embodiment of the present invention provides compounds according to formula I, wherein the compound of formula I is a compound of formula Ib

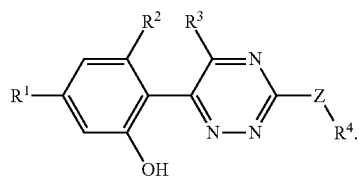

I

The compounds of formula Ib can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

Also an embodiment of the present invention provides compounds according to formula I as described herein and pharmaceutically acceptable salts or esters thereof, in particular compounds according to formula I as described herein and pharmaceutically acceptable salts thereof, more particularly compounds according to formula I as described herein.

An embodiment of the present invention provides compounds according to formula I as described herein, wherein
$R^1$ is H, halo, alkyl, haloalkyl, haloalkoxy, or nitrile;
$R^2$ is H, halo, alkyl, haloalkyl, cycloalkyl, or cycloalkylalkyl, wherein cycloalkyl or cycloalkylalkyl is optionally substituted with halo or haloalkoxy;
$R^3$ is H, alkyl, haloalkyl, or cycloalkyl optionally substituted with halo;
Z is -O-, -NH-, or -NHCH$_2$-;
$R^4$ is a heterocycle ring optionally substituted with 1 to 2 substituents independently selected from halo, alkyl, haloalkyl, hydroxyalkyl, -OH, oxo, -CO$_2$H, or cycloalkyl optionally substituted with halo; or
$R^4$ is a cycloalkyl optionally substituted with 1 to 3 substituents independently selected from alkyl, halo, haloalkyl and -OH;
and pharmaceutically acceptable salts.

An embodiment of the present invention provides compounds according to formula I as described herein, wherein
$R^1$ is H, halo, alkyl, haloalkyl, or haloalkoxy;
$R^2$ is H, halo, alkyl, haloalkyl, cycloalkyl, or cycloalkylalkyl, wherein cycloalkyl or cycloalkylalkyl is optionally substituted with halo or haloalkoxy;
$R^3$ is H, alkyl, haloalkyl, or cycloalkyl optionally substituted with halo;
Z is -O-, -NH-, or -NHCH$_2$-;
$R^4$ is a heterocycle ring optionally substituted with 1 to 2 substituents independently selected from halo, alkyl, haloalkyl, hydroxyalkyl, -OH, oxo, -CO$_2$H, or cycloalkyl optionally substituted with halo; or
$R^4$ is a cycloalkyl optionally substituted with 1 to 3 substituents independently selected from alkyl, halo, haloalkyl and -OH;
and pharmaceutically acceptable salts.

An embodiment of the present invention provides compounds according to formula I as described herein, wherein $R^1$ is H, halo, alkyl, haloalkyl, or haloalkoxy.

An embodiment of the present invention provides compounds according to formula I as described herein, wherein $R^1$ is halo or haloalkyl.

An embodiment of the present invention provides compounds according to formula I as described herein, wherein $R^1$ is F, Cl, OCF$_3$, CF$_3$, or CH$_3$.

An embodiment of the present invention provides compounds according to formula I as described herein, wherein $R^1$ is CF$_3$.

An embodiment of the present invention provides compounds according to formula I as described herein, where $R^2$ is H, halo, alkyl, haloalkyl, cycloalkyl, or cycloalkylalkyl, wherein cycloalkyl or cycloalkylalkyl is optionally substituted with halo;

An embodiment of the present invention provides compounds according to formula I as described herein, where $R^2$ is H, halo, alkyl, haloalkyl, or cycloalkyl, wherein cycloalkyl or cycloalkylalkyl is optionally substituted with halo;

An embodiment of the present invention provides compounds according to formula I as described herein, wherein $R^2$ is H, halo, alkyl or haloalkyl.

An embodiment of the present invention provides compounds according to formula I as described herein, wherein $R^2$ is H or alkyl.

An embodiment of the present invention provides compounds according to formula I as described herein, wherein $R^2$ is alkyl.

An embodiment of the present invention provides compounds according to formula I as described herein, wherein $R^2$ is H.

An embodiment of the present invention provides compounds according to formula I as described herein, wherein $R^3$ is H, alkyl or haloalkyl.

An embodiment of the present invention provides compounds according to formula I as described herein, wherein $R^3$ is H or alkyl.

An embodiment of the present invention provides compounds according to formula I as described herein, wherein $R^3$ is H.

An embodiment of the present invention provides compounds according to formula I as described herein, wherein $R^3$ is methyl.

An embodiment of the present invention provides compounds according to formula I as described herein, wherein $R^4$ is a heterocycle ring optionally substituted with alkyl, or a cycloalkyl ring optionally substituted with 1 to 2 substituents selected from alkyl and —OH.

An embodiment of the present invention provides compounds according to formula I as described herein, wherein $R^4$ is a heterocycle ring optionally substituted with alkyl.

An embodiment of the present invention provides compounds according to formula I as described herein, wherein $R^4$ is a heterocycle ring comprising 1 heteroatom substituted with alkyl.

An embodiment of the present invention provides compounds according to formula I as described herein, wherein $R^4$ is either ethylpiperidine or cyclobutane substituted with alkyl and —OH.

An embodiment of the present invention provides compounds according to formula I as described herein, wherein $R^4$ is ethylpiperidine.

An embodiment of the present invention provides compounds according to formula I as described herein, wherein Z is —O— or —NH—.

An embodiment of the present invention provides compounds according to formula I as described herein, wherein Z is —NH—.

An embodiment of the present invention provides compounds according to formula I as described herein, wherein
$R^1$ is Cl, $OCF_3$, alkyl or haloalkyl;
$R^2$ is H, halo, alkyl, haloalkyl or cycloalkyl optionally substituted with F;
$R^3$ is H, alkyl, haloalkyl, or cycloalkyl optionally substituted with F;
Z is —O—, or —NH—;
$R^4$ is a heterocycle ring optionally substituted with 1 to 2 substituents independently selected from halo, alkyl, haloalkyl, hydroxyalkyl, —OH, oxo, —$CO_2H$, or cycloalkyl optionally substituted with halo; or
$R^4$ is a cycloalkyl optionally substituted with 1 to 3 substituents independently selected from alkyl, halo, haloalkyl and —OH.

An embodiment of the present invention provides compounds according to formula I as described herein, wherein
$R^1$ is Cl, $CH_3$, $OCF_3$, or $CF_3$;
$R^2$ is H, halo, alkyl, or haloalkyl;
$R^3$ is H, alkyl or haloalkyl;
Z is —O—, or —NH—;
$R^4$ is a heterocycle ring comprising 1 heteroatom, optionally substituted with 1 to 2 substituents independently selected from halo, alkyl, haloalkyl, hydroxyalkyl, —OH, oxo, —$CO_2H$, or cycloalkyl optionally substituted with halo; or
$R^4$ is a cycloalkyl optionally substituted with 1 to 3 substituents independently selected from alkyl, halo, haloalkyl and —OH.

An embodiment of the present invention provides compounds according to formula I as described herein, wherein
$R^1$ is Cl, $CH_3$, $OCF_3$, or $CF_3$;
$R^2$ is H, halo, alkyl, or haloalkyl;
$R^3$ is H, alkyl or haloalkyl;
Z is —O—, or —NH—;
$R^4$ is a heterocycle ring comprising 1 heteroatom, optionally substituted with 1 to 2 substituents independently selected from halo, alkyl, or haloalkyl.

An embodiment of the present invention provides compounds according to formula I as described herein, wherein
$R^1$ is Cl, $CH_3$, $OCF_3$, or $CF_3$;
$R^2$ is H, halo, alkyl, or haloalkyl;
$R^3$ is H, alkyl or haloalkyl;
Z is —NH—;
$R^4$ is a heterocycle ring comprising 1 heteroatom, optionally substituted with 1 to 2 substituents independently selected from halo, alkyl, or haloalkyl.

An embodiment of the present invention provides compounds according to formula I as described herein, wherein
$R^1$ is halo or haloalkyl;
$R^2$ is H or alkyl;
$R^3$ is H or alkyl;
Z is —NH—;
$R^4$ is a heterocycle ring comprising 1 heteroatom, substituted with alkyl, or $R^4$ is a cycloalkyl ring substituted with 1 to 2 substituents independently selected from alkyl and —OH.

An embodiment of the present invention provides compounds according to formula I as described herein, wherein
$R^1$ is halo or $CF_3$;
$R^2$ is H or methyl;
$R^3$ is H or methyl;
Z is —NH—;
$R^4$ is a piperidine ring substituted with alkyl or a cyclobutane ring substituted with 1 to 2 substituents selected from alkyl and —OH.

An embodiment of the present invention provides compounds according to formula I as described herein, wherein
$R^1$ is $CF_3$ or Cl;
$R^2$ is H;
$R^3$ is methyl;
Z is —NH—;
$R^4$ is a piperidine ring substituted with alkyl.

An embodiment of the present invention provides compounds according to formula I as described herein, wherein
$R^1$ is $CF_3$;
$R^2$ is H;
$R^3$ is methyl;
Z is —NH—;
$R^4$ is a piperidine ring substituted with alkyl.

Particular examples of compounds of formula Ib as described herein are selected from
2-[3-[[(3R)-1-Ethyl-3-piperidyl]amino]-1,2,4-triazin-6-yl]-3-methyl-5-(trifluoromethyl) phenol;
5-Chloro-2-[3-[(1-ethyl-3-piperidyl)amino]-5-methyl-1,2,4-triazin-6-yl]phenol;
2-[3-[[(3R)-1-Ethyl-3-piperidyl]amino]-5-methyl-1,2,4-triazin-6-yl]-5-(trifluoromethyl) phenol;
2-[3-[(3-Hydroxy-3-methyl-cyclobutyl)amino]-5-methyl-1,2,4-triazin-6-yl]-5-(trifluoromethyl) phenol;
5-Chloro-2-[3-[[(3R)-1-ethyl-3-piperidyl]amino]-5-methyl-1,2,4-triazin-6-yl]phenol;
2-[3-[[(3R)-1-Ethyl-3-piperidyl]amino]-5-methyl-1,2,4-triazin-6-yl]-5-fluoro-phenol;
5-[3-[[(3R)-1-Ethyl-3-piperidyl]amino]-5-methyl-1,2,4-triazin-6-yl]-2,3-dihydrobenzofuran-4-ol;
and pharmaceutically acceptable salts thereof.

Other particular examples of compounds of formula Ib as described herein are selected from
3-[3-[[(3R)-1-Ethyl-3-piperidyl]amino]-5-methyl-1,2,4-triazin-6-yl]bicyclo[4.2.0]octa-1(6),2,4-trien-2-ol;

2-[3-[[(3R)-1-ethyl-3-piperidyl]amino]-5-methyl-1,2,4-triazin-6-yl]-3-fluoro-5-(trifluoromethyl) phenol;
2-[3-[[(3R or 3S)-1-tert-Butyl-3-piperidyl]amino]-5-methyl-1,2,4-triazin-6-yl]-5-(trifluoromethyl) phenol;
2-[3-[[(3S or 3R)-1-tert-Butyl-3-piperidyl]amino]-5-methyl-1,2,4-triazin-6-yl]-5-(trifluoromethyl) phenol;
4-[3-[[(3R)-1-ethyl-3-piperidyl]amino]-5-methyl-1,2,4-triazin-6-yl]-3-hydroxy-benzonitrile;
2-[3-[[(3R,5S)-5-Fluoro-1-methyl-3-piperidyl]amino]-5-methyl-1,2,4-triazin-6-yl]-5-(trifluoromethyl) phenol;
2-[5-Methyl-3-(5,6,7,8-tetrahydroimidazo[1,2-a]pyridin-8-ylamino)-1,2,4-triazin-6-yl]-5-(trifluoromethyl) phenol;
5-Fluoro-2-[5-methyl-3-[[(3R)-1-methyl-3-piperidyl]amino]-1,2,4-triazin-6-yl]phenol;
5-Chloro-2-[5-methyl-3-[[(3R)-1-methyl-3-piperidyl]amino]-1,2,4-triazin-6-yl]phenol;
2-[5-Methyl-3-[[(3R)-3-piperidyl]amino]-1,2,4-triazin-6-yl]-5-(trifluoromethyl) phenol;
2-[5-Methyl-3-[[(3R)-1-methyl-3-piperidyl]amino]-1,2,4-triazin-6-yl]-5-(trifluoromethyl) phenol;
2-[3-[[(1R,2R)-2-Hydroxycyclohexyl]amino]-5-methyl-1,2,4-triazin-6-yl]-5-(trifluoromethyl) phenol;
2-[3-[[(3R)-1-Ethyl-3-piperidyl]amino]-5-methyl-1,2,4-triazin-6-yl]-3-methyl-5-(trifluoromethyl) phenol;
2-[3-[[(3R)-1-Ethyl-3-piperidyl]amino]-5-methyl-1,2,4-triazin-6-yl]-5-(trifluoromethoxy) phenol;
(3S,5R)-1-Ethyl-5-[[6-[2-hydroxy-4-(trifluoromethyl)phenyl]-5-methyl-1,2,4-triazin-3-yl]amino]piperidin-3-ol;
(3S,5R)-1-Ethyl-5-[[6-[2-hydroxy-6-methyl-4-(trifluoromethyl)phenyl]-5-methyl-1,2,4-triazin-3-yl]amino]piperidin-3-ol;
5-[3-[[(3R)-1-Ethyl-3-piperidyl]amino]-5-methyl-1,2,4-triazin-6-yl]indan-4-ol;
2-[5-Methyl-3-[[rac-(8S,8aR)-1,2,3,5,6,7,8,8a-octahydroindolizin-8-yl]amino]-1,2,4-triazin-6-yl]-5-(trifluoromethyl) phenol;
2-[5-Methyl-3-[[rac-(8S,8aS)-1,2,3,5,6,7,8,8a-octahydroindolizin-8-yl]amino]-1,2,4-triazin-6-yl]-5-(trifluoromethyl) phenol;
2-[3-[[(8R,8aS or 8S,8aR)-1,2,3,5,6,7,8,8a-Octahydroindolizin-8-yl]amino]-5-methyl-1,2,4-triazin-6-yl]-3-methyl-5-(trifluoromethyl) phenol;
2-[3-[[(8S,8aR or 8R,8aS)-1,2,3,5,6,7,8,8a-Octahydroindolizin-8-yl]amino]-5-methyl-1,2,4-triazin-6-yl]-3-methyl-5-(trifluoromethyl) phenol;
2-[3-[[(3R)-1-Ethyl-3-piperidyl]amino]-5-(trifluoromethyl)-1,2,4-triazin-6-yl]-5-(trifluoromethyl) phenol;
2-[3-[[(6S or 6R,8aS or 8aR)-1,2,3,5,6,7,8,8a-octahydroindolizin-6-yl]amino]-5-methyl-1,2,4-triazin-6-yl]-5-(trifluoromethyl) phenol;
2-[3-[[(6R or 6S,8aS or 8aR)-1,2,3,5,6,7,8,8a-octahydroindolizin-6-yl]amino]-5-methyl-1,2,4-triazin-6-yl]-5-(trifluoromethyl) phenol;
2-[3-[[(6S or 6R,8aR or 8aS)-1,2,3,5,6,7,8,8a-octahydroindolizin-6-yl]amino]-5-methyl-1,2,4-triazin-6-yl]-5-(trifluoromethyl) phenol;
2-[3-[[(6R or 6S, 8aR or 8aS)-1,2,3,5,6,7,8,8a-octahydroindolizin-6-yl]amino]-5-methyl-1,2,4-triazin-6-yl]-5-(trifluoromethyl) phenol;
and pharmaceutically acceptable salts thereof.

Preferred example of compounds of formula Ib as described herein is 5-[3-[[(3R)-1-Ethyl-3-piperidyl]amino]-5-methyl-1,2,4-triazin-6-yl]-2,3-dihydrobenzofuran-4-ol, or pharmaceutically acceptable salts thereof.

Other preferred examples of compounds of formula Ib as described herein are selected from
2-[3-[[(3R)-1-Ethyl-3-piperidyl]amino]-5-methyl-1,2,4-triazin-6-yl]-5-(trifluoromethyl) phenol;
5-Chloro-2-[3-[[(3R)-1-ethyl-3-piperidyl]amino]-5-methyl-1,2,4-triazin-6-yl]phenol;
2-[3-[[(3R)-1-Ethyl-3-piperidyl]amino]-5-methyl-1,2,4-triazin-6-yl]-5-fluoro-phenol;
5-[3-[[(3R)-1-Ethyl-3-piperidyl]amino]-5-methyl-1,2,4-triazin-6-yl]-2,3-dihydrobenzofuran-4-ol;
3-[3-[[(3R)-1-Ethyl-3-piperidyl]amino]-5-methyl-1,2,4-triazin-6-yl]bicyclo[4.2.0]octa-1(6),2,4-trien-2-ol;
4-[3-[[(3R)-1-ethyl-3-piperidyl]amino]-5-methyl-1,2,4-triazin-6-yl]-3-hydroxy-benzonitrile;
5-Chloro-2-[5-methyl-3-[[(3R)-1-methyl-3-piperidyl]amino]-1,2,4-triazin-6-yl]phenol;
2-[5-Methyl-3-[[(3R)-1-methyl-3-piperidyl]amino]-1,2,4-triazin-6-yl]-5-(trifluoromethyl) phenol;
2-[3-[[(3R)-1-Ethyl-3-piperidyl]amino]-5-methyl-1,2,4-triazin-6-yl]-5-(trifluoromethoxy) phenol;
5-[3-[[(3R)-1-Ethyl-3-piperidyl]amino]-5-methyl-1,2,4-triazin-6-yl]indan-4-ol;
2-[3-[[(8R,8aS)-1,2,3,5,6,7,8,8a-octahydroindolizin-8-yl]amino]-5-methyl-1,2,4-triazin-6-yl]-3-methyl-5-(trifluoromethyl) phenol;
and pharmaceutically acceptable salts thereof.

More preferred examples of compounds of formula Ib as described herein are selected from
2-[3-[[(3R)-1-Ethyl-3-piperidyl]amino]-5-methyl-1,2,4-triazin-6-yl]-5-(trifluoromethyl) phenol;
5-[3-[[(3R)-1-Ethyl-3-piperidyl]amino]-5-methyl-1,2,4-triazin-6-yl]-2,3-dihydrobenzofuran-4-ol;
3-[3-[[(3R)-1-Ethyl-3-piperidyl]amino]-5-methyl-1,2,4-triazin-6-yl]bicyclo[4.2.0]octa-1(6),2,4-trien-2-ol;
2-[5-Methyl-3-[[(3R)-1-methyl-3-piperidyl]amino]-1,2,4-triazin-6-yl]-5-(trifluoromethyl) phenol;
2-[3-[[(3R)-1-Ethyl-3-piperidyl]amino]-5-methyl-1,2,4-triazin-6-yl]-5-(trifluoromethoxy) phenol;
5-[3-[[(3R)-1-Ethyl-3-piperidyl]amino]-5-methyl-1,2,4-triazin-6-yl]indan-4-ol;
and pharmaceutically acceptable salts thereof.

Most preferred examples of compounds of formula Ib as described herein are selected from
2-[3-[[(3R)-1-Ethyl-3-piperidyl]amino]-5-methyl-1,2,4-triazin-6-yl]-5-(trifluoromethyl) phenol;
5-[3-[[(3R)-1-Ethyl-3-piperidyl]amino]-5-methyl-1,2,4-triazin-6-yl]-2,3-dihydrobenzofuran-4-ol;
3-[3-[[(3R)-1-Ethyl-3-piperidyl]amino]-5-methyl-1,2,4-triazin-6-yl]bicyclo[4.2.0]octa-1(6),2,4-trien-2-ol;
and pharmaceutically acceptable salts thereof.

Particular examples of compounds of formula I as described herein are selected from
2-[3-[[(3R)-1-Ethyl-3-piperidyl]amino]-1,2,4-triazin-6-yl]-3-methyl-5-(trifluoromethyl) phenol;
5-Chloro-2-[3-[(1-ethyl-3-piperidyl)amino]-5-methyl-1,2,4-triazin-6-yl]phenol;
2-[3-[[(3R)-1-Ethyl-3-piperidyl]amino]-5-methyl-1,2,4-triazin-6-yl]-5-(trifluoromethyl) phenol;
2-[3-[(3-Hydroxy-3-methyl-cyclobutyl)amino]-5-methyl-1,2,4-triazin-6-yl]-5-(trifluoromethyl) phenol;
5-Chloro-2-[3-[[(3R)-1-ethyl-3-piperidyl]amino]-5-methyl-1,2,4-triazin-6-yl]phenol;
2-[3-[[(3R)-1-Ethyl-3-piperidyl]amino]-5-methyl-1,2,4-triazin-6-yl]-5-fluoro-phenol;
and pharmaceutically acceptable salts thereof.

Processes for the manufacture of compounds of formula I as described herein are an object of the invention.

The synthesis of the compound of formula I can, for example, be accomplished according to scheme 1.

Processes for the manufacture of compounds of formula Ib as described herein are an object of the invention.

The synthesis of the compound of formula I can, for example, be accomplished according to scheme 3.

General Synthesis Scheme for the Triazine Compounds:

The compounds of formula I may be prepared in accordance with the process variant described above and with the following scheme 1. The starting materials are commercially available or may be prepared in accordance with known methods.

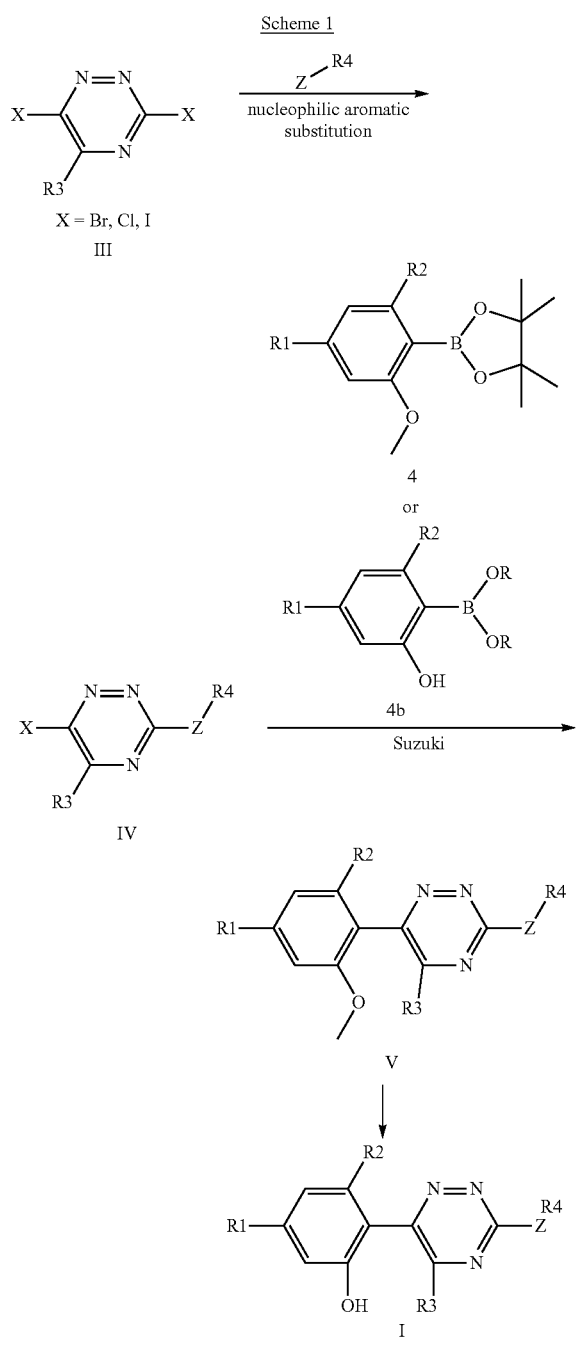

The synthesis of the compounds of formula I of the present invention are synthesized following to the general synthesis depicted in Scheme 1.

The commercially available building blocks of formula (III) where X is a halogen atom such as bromine, chlorine or iodine more preferably chlorine, can be submitted to a nucleophilic aromatic substitution in order to prepare compounds of formula (IV). The nucleophilic aromatic substitution are carried out with a suitable amine Z—$R^4$, wherein Z and $R^4$ have the meaning given for general formula I in the presence of bases as N,N-diisopropylethylamine (DIEA) or trimethylamine which are common and known to the skilled person and/or commercially available. Usually 1,4-dioxane as solvent was used, but solvents such as dimethyl sulfoxide (DMSO) or N-methyl-2-pyrrolidine (NMP) are also suitable. Other similar methods as Buchwald-Hartwig amination could be used. The left-hand side is added to the compound of general formula (IV) to form the compound of formula (V) using a Suzuki cross coupling in the presence of a palladium catalyst and a boronic acid or boronic pinacol ester such as 4 or 4b according to standard conditions well known to the skilled person. In a final step, the methyl ether group is cleaved with boron tribromide ($BBr_3$) in dichloromethane delivering the compounds of general formula I. Specific examples are described in more detail for each exemplified compound below.

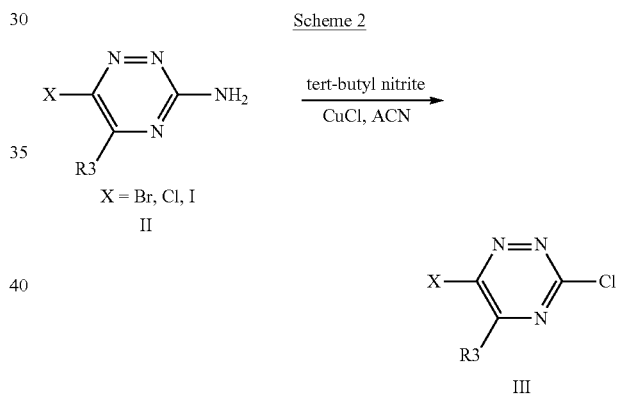

In the case where X is $NH_2$, the building block of formula (II) was also prepared via a Sandmeyer-type reaction to afford building block (III) wherein X=Cl. Specific examples are described for each exemplified compound below.

Further, in the cases where the amine Z—$R^4$ and $R^4$ contains e.g. a tert-butyloxycarbonyl (BOC) protecting group, an additional deprotection step was carried out either at an initial stage as described for Example 1 using TFA (trifluoroacetic acid) or at a final stage during the methyl ether cleavage.

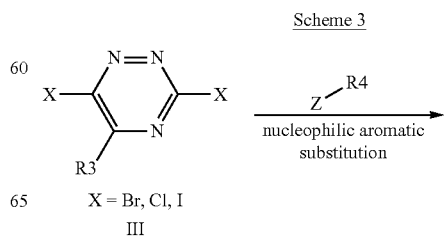

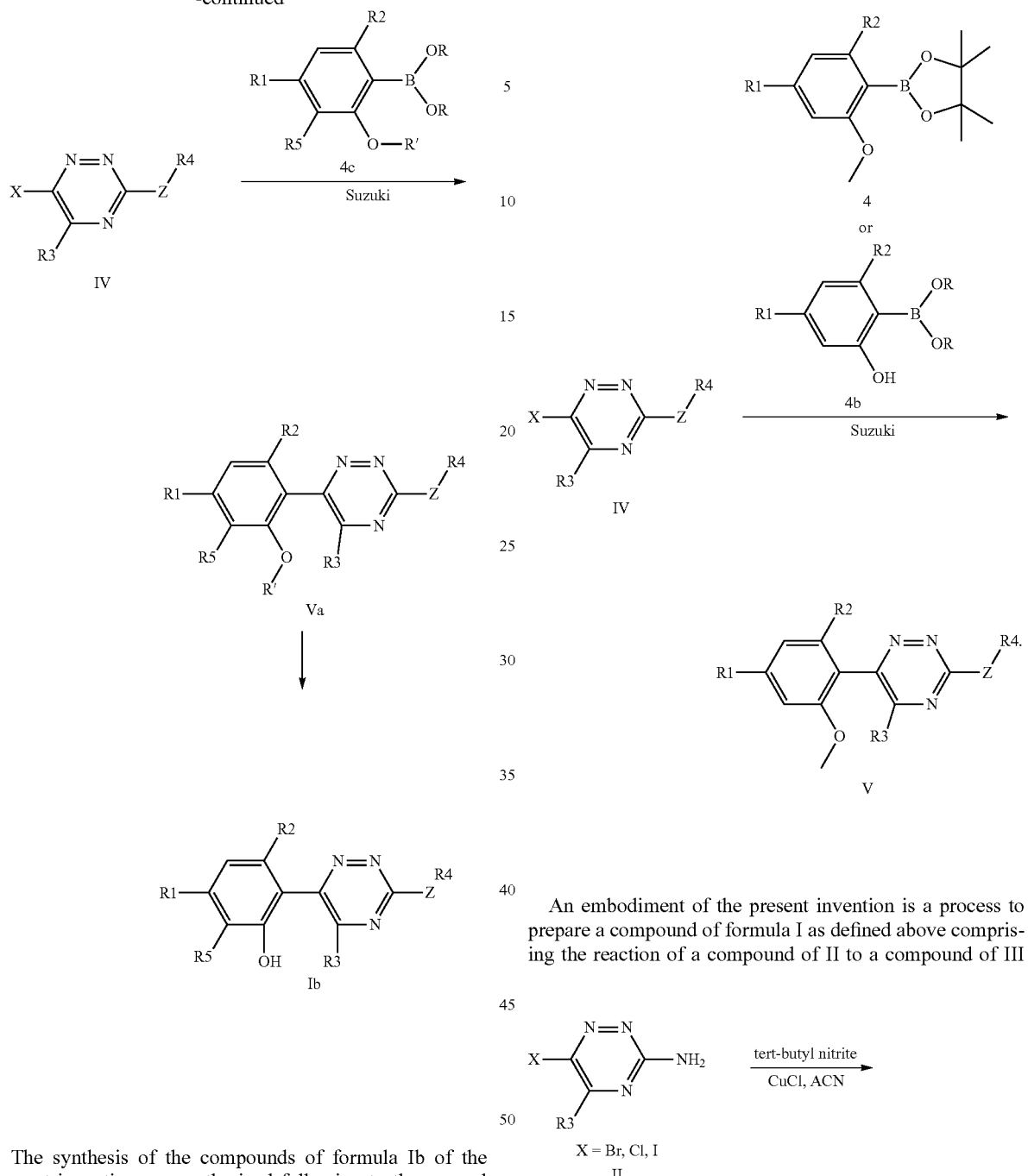

The synthesis of the compounds of formula Ib of the present invention are synthesized following to the general synthesis depicted in Scheme 3, wherein R' can be H or a protecting group known to the skilled person such as SEM, benzyl or any other suitable protecting group for phenols. In the case where R'=H, Va equals to Ib.

The invention thus relates to a compound according to the invention when manufactured according to a process of the invention.

An embodiment of the present invention is a process to prepare a compound of formula I as defined above comprising the reaction of a compound of IV to a compound of formula V in the presence of a palladium catalyst and a boronic acid or boronic pinacol ester, wherein $R^1$, $R^2$, $R^3$, $R^4$, and Z are as defined above An embodiment of the present invention is a process to prepare a compound of formula I as defined above comprising the reaction of a compound of II to a compound of III An embodiment of the present invention is a process to prepare a compound of formula Ib as defined above comprising the reaction of a compound of IV to a compound of formula Va in the presence of a palladium catalyst and a boronic acid or boronic pinacol ester, wherein $R^1$, $R^2$, $R^3$, $R^4$, $R^5$ and Z are as defined above

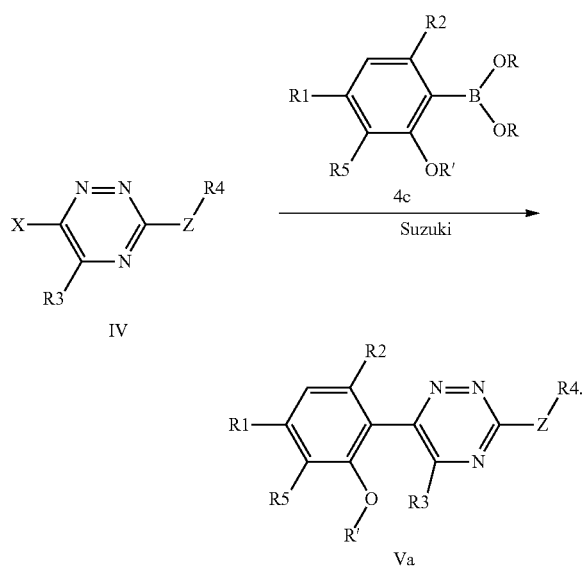

An embodiment of the present invention is a process to prepare a compound of formula Ib as defined above comprising the reaction of a compound of II to a compound of III Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula Ib may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula Ib is formulated in an acetate buffer, at pH 5. In another embodiment, the compound of formula Ib is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The compounds of formula Ib and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

The compounds of formula I and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

An embodiment of the present invention is a compound according to formula Ib as described herein for use as a therapeutically active substance.

An embodiment of the present invention is a compound according to formula Ib as described herein for use in the treatment or prevention of a disease, disorder or condition, wherein the disease, disorder or condition is responsive to NLRP3 inhibition.

An embodiment of the present invention is a compound according to formula Ib as described herein for the treatment or prophylaxis of a disease, disorder or condition, wherein the disorder or condition is responsive to NLRP3 inhibition.

An embodiment of the present invention is a compound according to formula I as described herein for use as a therapeutically active substance.

An embodiment of the present invention is a compound according to formula I as described herein for use in the treatment or prevention of a disease, disorder or condition, wherein the disease, disorder or condition is responsive to NLRP3 inhibition.

An embodiment of the present invention is a compound according to formula I as described herein for the treatment or prophylaxis of a disease, disorder or condition, wherein the disorder or condition is responsive to NLRP3 inhibition.

As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481:278-286, 2012).

In one embodiment, the disease, disorder or condition is selected from:
(i) inflammation;
(ii) an auto-immune disease;
(iii) cancer;
(iv) an infection;
(v) a central nervous system disease;
(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder;
(xv) graft versus host disease;
(xvi) allodynia;
(xvii) a condition associated with diabetes; and
(xviii) any disease where an individual has been determined to carry a germline or somatic non-silent mutation in NLRP3

In another embodiment, the disease, disorder or condition is selected from:
(i) cancer;
(ii) an infection;
(iii) a central nervous system disease;
(iv) a cardiovascular disease;
(v) a liver disease;
(vi) an ocular disease; or
(vii) a skin disease.

In a further typical embodiment of the invention, the disease, disorder or condition is inflammation. Examples of inflammation that may be treated or prevented include inflammatory responses occurring in connection with, or as a result of:
(i) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;
(ii) a joint condition such as osteoarthritis, systemic juvenile idiopathic arthritis, adult-onset Still's disease, relapsing polychondritis, rheumatoid arthritis, juvenile chronic arthritis, gout, or a seronegative spondyloarthropathy (e.g. ankylosing spondylitis, psoriatic arthritis or Reiter's disease);
(iii) a muscular condition such as polymyositis or myasthenia gravis;
(iv) a gastrointestinal tract condition such as inflammatory bowel disease (including Crohn's disease and ulcerative colitis), colitis, gastric ulcer, Coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);
(v) a respiratory system condition such as chronic obstructive pulmonary disease (COPD), asthma (including eosinophilic, bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, volcanic ash induced inflammation, adult respiratory distress syndrome, hypersensitivity pneumonitis, or idiopathic interstitial pneumonia;
(vi) a vascular condition such as atherosclerosis, Behcet's disease, vasculitides, or Wegener's granulomatosis;

(vii) an autoimmune condition such as systemic lupus erythematosus, Sjögren's syndrome, systemic sclerosis, Hashimoto's thyroiditis, type I diabetes, idiopathic thrombocytopenia purpura, or Graves disease;

(viii) an ocular condition such as uveitis, allergic conjunctivitis, or vernal conjunctivitis;

(ix) a nervous condition such as multiple sclerosis or encephalomyelitis;

(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis* (including *Mycobacterium tuberculosis* and HIV co-infection), *Mycobacterium avium intracellulare*, *Pneumocystis carinii* pneumonia, orchitis/epidydimitis, *legionella*, Lyme disease, influenza A, Epstein-Barr virus infection, viral encephalitis/aseptic meningitis, or pelvic inflammatory disease;

(xi) a renal condition such as mesangial proliferative glomerulonephritis, nephrotic syndrome, nephritis, glomerular nephritis, obesity related glomerulopathy, acute renal failure, acute kidney injury, uremia, nephritic syndrome, kidney fibrosis including chronic crystal nephropathy, or renal hypertension;

(xii) a lymphatic condition such as Castleman's disease;

(xiii) a condition of, or involving, the immune system, such as hyper IgE syndrome, lepromatous leprosy, familial hemophagocytic lymphohistiocytosis, or graft versus host disease;

(xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH), primary biliary cirrhosis, fulminant hepatitis, liver fibrosis, or liver failure;

(xv) a cancer, including those cancers listed above;

(xvi) a burn, wound, trauma, haemorrhage or stroke;

(xvii) radiation exposure;

(xviii) a metabolic disease such as type 2 diabetes (T2D), atherosclerosis, obesity, gout or pseudo-gout; and/or (xix) pain such as inflammatory hyperalgesia, pelvic pain, allodynia, neuropathic pain, or cancer-induced bone pain.

An embodiment of the present invention is a compound according to formula Ib as described herein for the treatment or prophylaxis of a disease, disorder or condition selected from:

(i) inflammation;
(ii) an auto-immune disease;
(iii) cancer;
(iv) an infection;
(v) a central nervous system disease;
(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder;
(xv) graft versus host disease;
(xvi) allodynia;
(xvii) a condition associated with diabetes; and
(xviii) any disease where an individual has been determined to carry a germline or somatic non-silent mutation in NLRP3.

An embodiment of the present invention is the use of a compound according to formula Ib as described herein in the treatment or prophylaxis of a disease, disorder or condition selected from Alzheimer's disease and Parkinson's disease.

An embodiment of the present invention is the use a compound according to formula Ib as described herein for use in the treatment or prophylaxis of a disease, disorder or condition selected from Asthma or COPD.

An embodiment of the present invention is the use a compound according to formula Ib as described herein for use in the treatment or prophylaxis of a disease, disorder or condition selected from inflammatory bowel disease (including Crohn's disease and ulcerative colitis).

An embodiment of the present invention is a compound according to formula Ib as described herein for the treatment or prophylaxis of a disease, disorder or condition selected from Alzheimer's disease and Parkinson's disease.

An embodiment of the present invention is a compound according to formula Ib as described herein for the treatment or prophylaxis of a disease, disorder or condition selected from Asthma or COPD.

An embodiment of the present invention is a compound according to formula Ib as described herein for the treatment or prophylaxis of a disease, disorder or condition selected from inflammatory bowel disease (including Crohn's disease and ulcerative colitis).

An embodiment of the present invention is the use of a compound according to formula Ib as described herein for preparation of a medicament for the treatment or prophylaxis of a disease, disorder or condition selected from Alzheimer's disease and Parkinson's disease.

An embodiment of the present invention is the use of a compound according to formula Ib as described herein for the preparation of a medicament for the treatment or prophylaxis of a disease, disorder or condition selected from Asthma or COPD.

An embodiment of the present invention is the use of a compound according to formula Ib as described herein for the preparation of a medicament for the treatment or prophylaxis of a disease, disorder or condition selected from inflammatory bowel disease (including Crohn's disease and ulcerative colitis).

An embodiment of the present invention is a method of treatment or prophylaxis of a disease, disorder or condition selected from Alzheimer's disease and Parkinson's disease, which method comprises administering an effective amount of a compound according to formula Ib as described herein.

An embodiment of the present invention is a method of treatment or prophylaxis of a disease, disorder or condition selected from Asthma or COPD, which method comprises administering an effective amount of a compound according to formula Ib as described herein.

An embodiment of the present invention is a method of treatment or prophylaxis of a disease, disorder or condition selected from inflammatory bowel disease (including Crohn's disease and ulcerative colitis), which method comprises administering an effective amount of a compound according to formula Ib as described herein.

An embodiment of the present invention relates to a method of inhibiting NLRP3, which method comprises administering an effective amount of a compound according to formula Ib as described herein.

Also an embodiment of the present invention are compounds of formula Ib as described herein, when manufactured according to any one of the described processes.

An embodiment of the present invention is a pharmaceutical composition comprising a compound according to formula Ib as described herein and a therapeutically inert carrier.

An embodiment of the present invention is a compound according to formula I as described herein for the treatment or prophylaxis of a disease, disorder or condition selected from:
(i) inflammation;
(ii) an auto-immune disease;
(iii) cancer;
(iv) an infection;
(v) a central nervous system disease;
(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder;
(xv) graft versus host disease;
(xvi) allodynia;
(xvii) a condition associated with diabetes; and
(xviii) any disease where an individual has been determined to carry a germline or somatic non-silent mutation in NLRP3.

An embodiment of the present invention is the use of a compound according to formula I as described herein in the treatment or prophylaxis of a disease, disorder or condition selected from Alzheimer's disease and Parkinson's disease.

An embodiment of the present invention is the use a compound according to formula I as described herein for use in the treatment or prophylaxis of a disease, disorder or condition selected from Asthma or COPD.

An embodiment of the present invention is a compound according to formula I as described herein for the treatment or prophylaxis of a disease, disorder or condition selected from Alzheimer's disease and Parkinson's disease.

An embodiment of the present invention is a compound according to formula I as described herein for the treatment or prophylaxis of a disease, disorder or condition selected from Asthma or COPD.

An embodiment of the present invention is the use of a compound according to formula I as described herein for preparation of a medicament for the treatment or prophylaxis of a disease, disorder or condition selected from Alzheimer's disease and Parkinson's disease.

An embodiment of the present invention is the use of a compound according to formula I as described herein for the preparation of a medicament for the treatment or prophylaxis of a disease, disorder or condition selected from Asthma or COPD.

An embodiment of the present invention is a method of treatment or prophylaxis of a disease, disorder or condition selected from Alzheimer's disease and Parkinson's disease, which method comprises administering an effective amount of a compound according to formula I as described herein.

An embodiment of the present invention is a method of treatment or prophylaxis of a disease, disorder or condition selected from Asthma or COPD, which method comprises administering an effective amount of a compound according to formula I as described herein.

An embodiment of the present invention relates to a method of inhibiting NLRP3, which method comprises administering an effective amount of a compound according to formula I as described herein.

Also an embodiment of the present invention are compounds of formula I as described herein, when manufactured according to any one of the described processes.

An embodiment of the present invention is a pharmaceutical composition comprising a compound according to formula I as described herein and a therapeutically inert carrier.

Assay Procedures

NLRP3 and Pyroptosis

It is well established that the activation of NLRP3 leads to cell pyroptosis and this feature plays an important part in the manifestation of clinical disease (Yan-gang Liu et al., Cell Death & Disease, 2017, 8 (2), e2579; Alexander Wree et al., Hepatology, 2014, 59 (3), 898-910; Alex Baldwin et al., Journal of Medicinal Chemistry, 2016, 59 (5), 1691-1710; Ema Ozaki et al., Journal of Inflammation Research, 2015, 8, 15-27; Zhen Xie & Gang Zhao, Neuroimmunology Neuroinflammation, 2014, 1 (2), 60-65; Mattia Cocco et al., Journal of Medicinal Chemistry, 2014, 57 (24), 10366-10382; T. Satoh et al., Cell Death & Disease, 2013, 4, e644). Therefore, it is anticipated that inhibitors of NLRP3 will block pyroptosis, as well as the release of pro-inflammatory cytokines (e.g. IL-1B) from the cell.

THP-1 Cells: Culture and Preparation

THP-1 cells (ATCC #TIB-202) were grown in RPMI containing L-glutamine (Gibco #11835) supplemented with 1 mM sodium pyruvate (Sigma #S8636) and penicillin (100 units/ml)/streptomycin (0.1 mg/ml) (Sigma #P4333) in 10% Fetal Bovine Serum (FBS) (Sigma #F0804). The cells were routinely passaged and grown to confluency ($\sim 10^6$ cells/ml). On the day of the experiment, THP-1 cells were harvested and resuspended into RPMI medium (without FBS). The cells were then counted and viability (>90%) checked by Trypan blue (Sigma #T8154). Appropriate dilutions were made to give a concentration of 625,000 cells/ml. To this diluted cell solution was added LPS (Sigma #L4524) to give a 1ug/ml Final Assay Concentration (FAC). 40 µl of the final preparation was aliquoted into each well of a 96-well plate. The plate thus prepared was used for compound screening.

THP-1 Cells Pyroptosis Assay

The following method step-by-step assay was followed for compound screening.
1. Seed THP-1 cells (25,000 cells/well) containing 1.0 µg/ml LPS in 40 µl of RPMI medium (without FBS) in 96-well, black walled, clear bottom cell culture plates coated with poly-D-lysine (VWR #734-0317)
2. Add 5 µl compound (8 points half-log dilution, with 10 µM top dose) or vehicle (DMSO 0.1% FAC) to the appropriate wells
3. Incubate for 3 hours at 37° C., 5% $CO_2$
4. Add 5 µl nigericin (Sigma #N7143) (FAC 5 µM) to all wells
5. Incubate for 1 hr at 37° C., 5% $CO_2$
6. At the end of the incubation period, spin plates at 300×g for 3 mins and remove supernatant
7. Then add 50 µl of resazurin (Sigma #R7017) (FAC 100 µM resazurin in RPMI medium without FBS) and incubate plates for a further 1-2 hours at 37° C. and 5% $CO_2$
8. Plates were read in an Envision reader at Ex 560 nm and Em 590 nm
9. $IC_{50}$ data is fitted to a non-linear regression equation (log inhibitor vs response-variable slope 4-parameters)

The results of the pyroptosis assay are summarised in Table 1 below as THP $IC_{50}$.

Human Whole Blood IL-1β Release Assay

For systemic delivery, the ability to inhibit NLRP3 when the compounds are present within the bloodstream is of great importance. For this reason, the NLRP3 inhibitory activity of a number of compounds in human whole blood was investigated in accordance with the following protocol.

Human whole blood in Li-heparin tubes was obtained from healthy donors from a volunteer donor panel.

1. Plate out 80 µl of whole blood containing 1ug/ml of LPS in 96-well, clear bottom cell culture plate (Corning #3585)
2. Add 10 µl compound (8 points half-log dilution with 10 µM top dose) or vehicle (DMSO 0.1% FAC) to the appropriate wells
3. Incubate for 3 hours at 37° C., 5% $CO_2$
4. Add 10 µl nigericin (Sigma #N7143) (10 µM FAC) to all wells
5. Incubate for 1 hr at 37° C., 5% $CO_2$
6. At the end of the incubation period, spin plates at 300×g for 5 mins to pellet cells and remove 20 µl of supernatant and add to 96-well v-bottom plates for IL-1β analysis (note: these plates containing the supernatants can be stored at −80° C. to be analysed at a later date)
7. IL-1β was measured according to the manufacturer protocol (Perkin Elmer-AlphaLisa IL-1 Kit AL220F-5000)
8. IC50 data is fitted to a non-linear regression equation (log inhibitor vs response-variable slope 4-parameters)

The results of the human whole blood assay are summarised in Table 1 below as HWB $IC_{50}$.

hERG Screening Assay

Cells

The CHO crelox hERG cell line (ATCC reference Nr. PTA-6812, female Chinese hamster cells) was generated and validated at Roche. Ready-to-use frozen instant CHO-hERG cells were cryopreserved at Evotec (Germany) and used directly in the experiments.

Experimental Solutions

The extracellular solution contains (in mM): NaCl 150; KCl 4; $CaCl_2$ 1; $MgCl_2$ 1; HEPES 10; pH 7.2-7.4 with NaOH, osmolarity 290-330 mOsm. The internal solution contains (in mM): KCl, 10; KF, 100; NaCl, 10; HEPES, 10; EGTA, 20; pH=7.0-7.4 with KOH, osmolarity 260-300 mOsm.

Electrophysiology

The effects of a compound on hERG K+-currents parameters will be evaluated at 2 concentrations in at least 4 cells.

The hERG test is performed using automated patch clamp system SynchroPatch® 384 (Nanion Technologies GmbH, Germany). K+ currents are measured with the patch-voltage-clamp technique in the whole-cell configuration at 35-37° C.

Cells were held at a resting voltage of −80 mV and they were stimulated by a voltage pattern shown in FIG. 1 to activate hERG channels and conduct outward IKhERG current, at a stimulation frequency of 0.1 Hz (6 bpm)

Data Analysis

The amplitudes of IKhERG were recorded in each concentration of drug and they were compared to the vehicle control values (taken as 100%) to define fractional blocks. The concentration-response data were fitted with the following relationship:

$$I(C) = \frac{100}{1 + (C/IC50)^h}$$

where C is the concentration,
$IC_{50}$ is the concentration producing 50% block
h is the Hill coefficient.

Concentration-response curves were fitted by non-linear regression analysis using EworkBook suite (ID Business Solutions Ltd, UK). Data fit was done with the 4 Parameter Logistic Model (fit=(A+(B/(1+((x/C)^D)))), where A=0 and B=100).

TABLE 1

NLRP3 inhibitory activity

| Example No. | Structure | Name | THP-1 pyroptosis assay $IC_{50}$ (nM) | Human whole blood IL-1β Assay $IC_{50}$ (nM) |
|---|---|---|---|---|
| 1 | 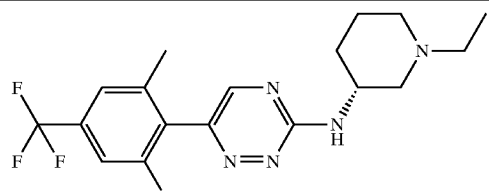 | 2-[3-[[(3R)-1-Ethyl-3-piperidyl]amino]-1,2,4-triazin-6-yl]-3-methyl-5-(trifluoromethyl) phenol; 2,2,2-trifluoroacetic acid | 9 | 39 |
| 2 | 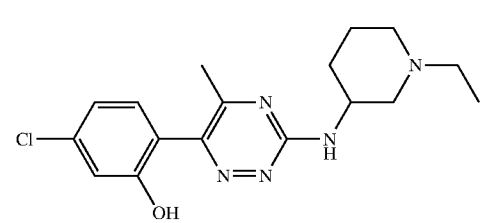 [SMILES: CCN1CCCC(Nc2nnc(-c3ccc(Cl)cc3O)c(C)n2)C1] | 5-Chloro-2-[3-[(1-ethyl-3-piperidyl)amino]-5-methyl-1,2,4-triazin-6-yl]phenol | | |

TABLE 1-continued

NLRP3 inhibitory activity

| Example No. | Structure | Name | THP-1 pyroptosis assay IC$_{50}$ (nM) | Human whole blood IL-1β Assay IC$_{50}$ (nM) |
|---|---|---|---|---|
| 3 | 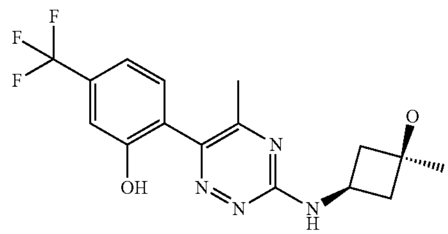 [SMILES: Cc1nc(N[C@H]2C[C@@](C)(O)C2)nnc1-c1ccc(C(F)(F)F)cc1O] | 2-[3-[(3-Hydroxy-3-methyl-cyclobutyl)amino]-5-methyl-1,2,4-triazin-6-yl]-5-(trifluoromethyl)phenol | 107.3 | 190.9 |
| 4 | 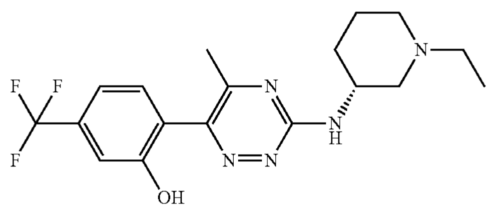 [SMILES: CCN1CCC[C@@H](Nc2nnc(-c3ccc(C(F)(F)F)cc3O)c(C)n2)C1] | 2-[3-[[(3R)-1-Ethyl-3-piperidyl]amino]-5-methyl-1,2,4-triazin-6-yl]-5-(trifluoromethyl)phenol | 1.7 | 5.4 |
| 5 | 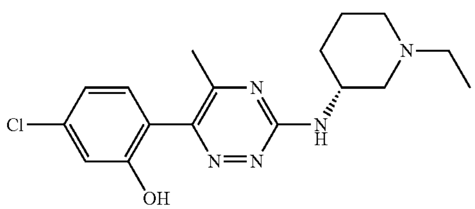 | 5-Chloro-2-[3-[[(3R)-1-ethyl-3-piperidyl]amino]-5-methyl-1,2,4-triazin-6-yl]phenol | 1.3 | 3.8 |
| 6 | 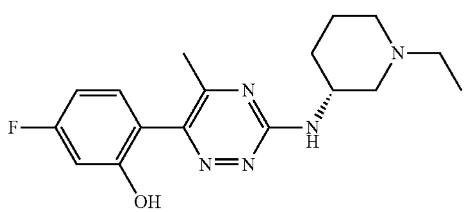 [SMILES: CCN1CCC[C@@H](Nc2nnc(-c3ccc(F)cc3O)c(C)n2)C1] | 2-[3-[[(3R)-1-Ethyl-3-piperidyl]amino]-5-methyl-1,2,4-triazin-6-yl]-5-fluoro-phenol | 15.5 | 14.6 |
| 7 | 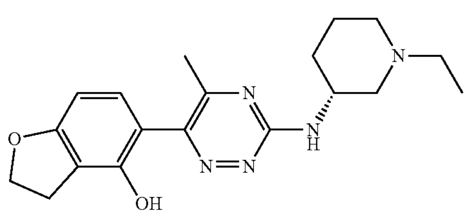 [SMILES: CCN1CCC[C@@H](Nc2nnc(-c3ccc4c(c3O)CCO4)c(C)n2)C1] | 5-[3-[[(3R)-1-Ethyl-3-piperidyl]amino]-5-methyl-1,2,4-triazin-6-yl]-2,3-dihydrobenzofuran-4-ol | 1.1 | 3.7 |
| 8 | 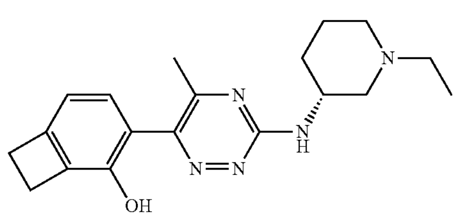 [SMILES: CCN1CCC[C@@H](Nc2nnc(-c3ccc4c(c3O)CC4)c(C)n2)C1] | 3-[3-[[(3R)-1-Ethyl-3-piperidyl]amino]-5-methyl-1,2,4-triazin-6-yl]bicyclo[4.2.0]octa-1(6),2,4-trien-2-ol | 0.4 | 4.3 |

TABLE 1-continued

NLRP3 inhibitory activity

| Example No. | Structure | Name | THP-1 pyroptosis assay IC$_{50}$ (nM) | Human whole blood IL-1β Assay IC$_{50}$ (nM) |
|---|---|---|---|---|
| 9 | 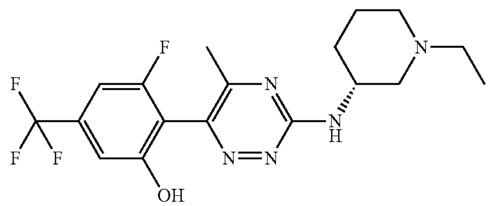 [SMILES: CCN1CCC[C@@H](Nc2nnc(-c3c(O)cc(C(F)(F)F)cc3F)c(C)n2)C1] | 2-[3-[[(3R)-1-Ethyl-3-piperidyl]amino]-5-methyl-1,2,4-triazin-6-yl]-3-fluoro-5-(trifluoromethyl)phenol | 3.5 | 27.4 |
| 10 | | 2-[3-[[(3R or 3S)-1-tert-Butyl-3-piperidyl]amino]-5-methyl-1,2,4-triazin-6-yl]-5-(trifluoromethyl)phenol | 434 | |
| 11 | | 2-[3-[[(3S or 3R)-1-tert-Butyl-3-piperidyl]amino]-5-methyl-1,2,4-triazin-6-yl]-5-(trifluoromethyl)phenol | 2.2 | 15.6 |
| 12 | 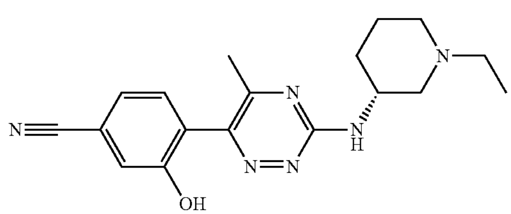 [SMILES: CCN1CCC[C@@H](Nc2nnc(-c3ccc(C#N)cc3O)c(C)n2)C1] | 4-[3-[[(3R)-1-Ethyl-3-piperidyl]amino]-5-methyl-1,2,4-triazin-6-yl]-3-hydroxybenzonitrile | 20.5 | 23.9 |

TABLE 1-continued

NLRP3 inhibitory activity

| Example No. | Structure | Name | THP-1 pyroptosis assay IC$_{50}$ (nM) | Human whole blood IL-1β Assay IC$_{50}$ (nM) |
|---|---|---|---|---|
| 13 | 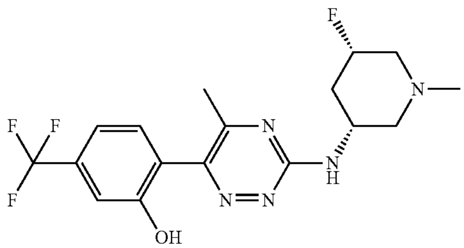 [SMILES: Cc1nc(N[C@@H]2C[C@H](F)CN(C)C2)nnc1-c1ccc(C(F)(F)F)cc1O] | 2-[3-[[(3R,5S)-5-Fluoro-1-methyl-3-piperidyl]amino]-5-methyl-1,2,4-triazin-6-yl]-5-(trifluoromethyl)phenol | 77.0 | |
| 14 | 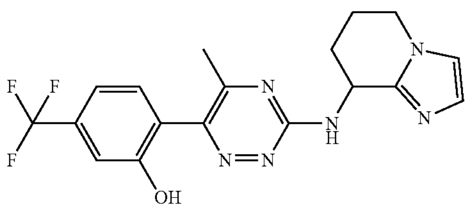 [SMILES: Cc1nc(NC2CCCn3ccnc32)nnc1-c1ccc(C(F)(F)F)cc1O] | 2-[5-Methyl-3-(5,6,7,8-tetrahydroimidazo[1,2-a]pyridin-8-ylamino)-1,2,4-triazin-6-yl]-5-(trifluoromethyl)phenol | 350.1 | |
| 15 | 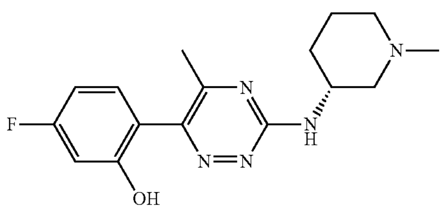 [SMILES: Cc1nc(N[C@@H]2CCCN(C)C2)nnc1-c1ccc(F)cc1O] | 5-Fluoro-2-[5-methyl-3-[[(3R)-1-methyl-3-piperidyl]amino]-1,2,4-triazin-6-yl]phenol | 18.3 | 15.1 |
| 16 | 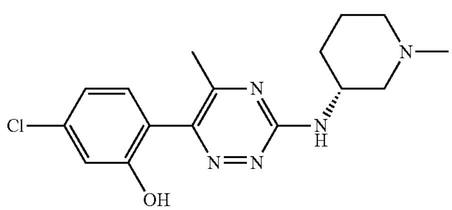 [SMILES: Cc1nc(N[C@@H]2CCCN(C)C2)nnc1-c1ccc(Cl)cc1O] | 5-Chloro-2-[5-methyl-3-[[(3R)-1-methyl-3-piperidyl]amino]-1,2,4-triazin-6-yl]phenol | 1.5 | 13.2 |
| 17 | 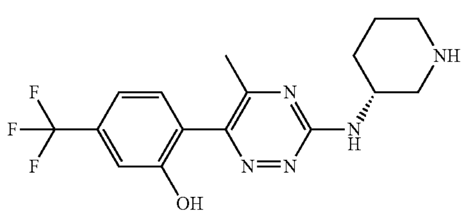 [SMILES: Cc1nc(N[C@@H]2CCCNC2)nnc1-c1ccc(C(F)(F)F)cc1O] | 2-[5-Methyl-3-[[(3R)-3-piperidyl]amino]-1,2,4-triazin-6-yl]-5-(trifluoromethyl)phenol | 13.4 | 46.5 |
| 18 | 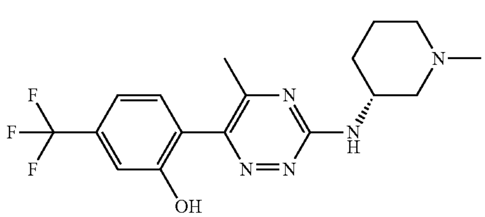 [SMILES: Cc1nc(N[C@@H]2CCCN(C)C2)nnc1-c1ccc(C(F)(F)F)cc1O] | 2-[5-Methyl-3-[[(3R)-1-methyl-3-piperidyl]amino]-1,2,4-triazin-6-yl]-5-(trifluoromethyl)phenol | 1.0 | 20.2 |

TABLE 1-continued

NLRP3 inhibitory activity

| Example No. | Structure | Name | THP-1 pyroptosis assay IC$_{50}$ (nM) | Human whole blood IL-1β Assay IC$_{50}$ (nM) |
|---|---|---|---|---|
| 19 | 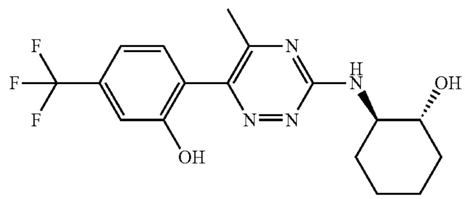 [SMILES: Cc1nc(N[C@@H]2CCCC[C@H]2O)nnc1-c1ccc(C(F)(F)F)cc1O] | 2-[3-[[(1R,2R)-2-Hydroxycyclohexyl]amino]-5-methyl-1,2,4-triazin-6-yl]-5-(trifluoromethyl)phenol | 32.2 | 227.8 |
| 21 | 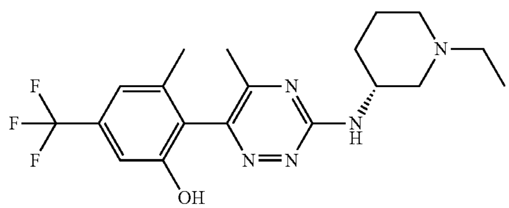 | 2-[3-[[(3R)-1-Ethyl-3-piperidyl]amino]-5-methyl-1,2,4-triazin-6-yl]-3-methyl-5-(trifluoromethyl)phenol | 1.6 | 57.6 |
| 22 | 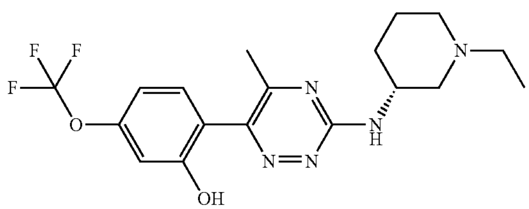 [SMILES: CCN1CCC[C@@H](Nc2nnc(-c3ccc(OC(F)(F)F)cc3O)c(C)n2)C1] | 2-[3-[[(3R)-1-Ethyl-3-piperidyl]amino]-5-methyl-1,2,4-triazin-6-yl]-5-(trifluoromethoxy)phenol | 1.2 | 10.2 |
| 23 | 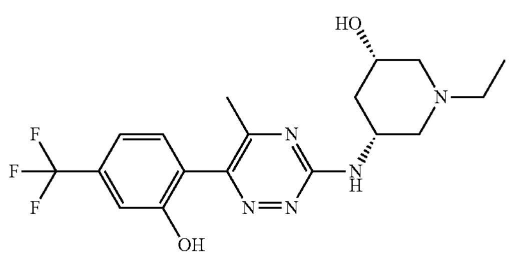 [SMILES: CCN1C[C@@H](O)C[C@@H](Nc2nnc(-c3ccc(C(F)(F)F)cc3O)c(C)n2)C1] | (3S,5R)-1-Ethyl-5-[[6-[2-hydroxy-4-(trifluoromethyl)phenyl]-5-methyl-1,2,4-triazin-3-yl]amino]piperidin-3-ol | 40.1 | 40.5 |
| 24 | 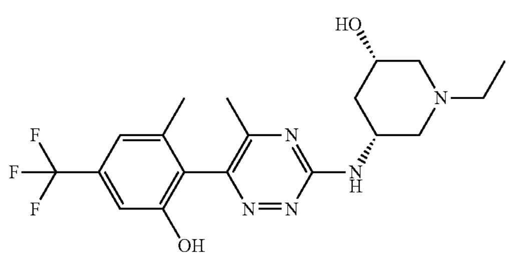 [SMILES: CCN1C[C@@H](O)C[C@@H](Nc2nnc(-c3c(C)cc(C(F)(F)F)cc3O)c(C)n2)C1] | (3S,5R)-1-Ethyl-5-[[6-[2-hydroxy-6-methyl-4-(trifluoromethyl)phenyl]-5-methyl-1,2,4-triazin-3-yl]amino]piperidin-3-ol | 49.6 | 124.9 |
| 25 | 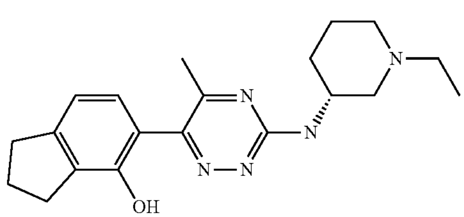 [SMILES: CCN1CCC[C@@H](Nc2nnc(-c3ccc4c(c3O)CCC4)c(C)n2)C1] | 5-[3-[[(3R)-1-Ethyl-3-piperidyl]amino]-5-methyl-1,2,4-triazin-6-yl]indan-4-ol | 0.7 | 6.3 |

TABLE 1-continued

NLRP3 inhibitory activity

| Example No. | Structure | Name | THP-1 pyroptosis assay IC$_{50}$ (nM) | Human whole blood IL-1β Assay IC$_{50}$ (nM) |
|---|---|---|---|---|
| 26 | 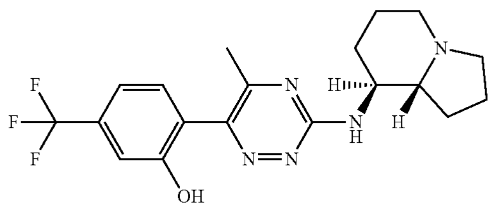 [SMILES: Cc1nc(N[C@H]2CCCN3CCC[C@H]23)nnc1-c1ccc(C(F)(F)F)cc1O] | 2-[5-Methyl-3-[[rac-(8S,8aR)-1,2,3,5,6,7,8,8a-octahydroindolizin-8-yl]amino]-1,2,4-triazin-6-yl]-5-(trifluoromethyl)phenol | 5.1 | |
| 27 | 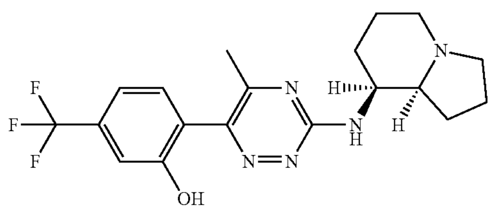 [SMILES: Cc1nc(N[C@H]2CCCN3CCC[C@@H]23)nnc1-c1ccc(C(F)(F)F)cc1O] | 2-[5-Methyl-3-[[rac-(8S,8aS)-1,2,3,5,6,7,8,8a-octahydroindolizin-8-yl]amino]-1,2,4-triazin-6-yl]-5-(trifluoromethyl)phenol | 20.9 | |
| 28 | | 2-[3-[[(8R,8aS or 8S,8aR)-1,2,3,5,6,7,8,8a-Octahydroindolizin-8-yl]amino]-5-methyl-1,2,4-triazin-6-yl]-3-methyl-5-(trifluoromethyl)phenol | 2.4 | 18.8 |
| 29 | | 2-[3-[[(8S,8aR or 8R,8aS)-1,2,3,5,6,7,8,8a-Octahydroindolizin-8-yl]amino]-5-methyl-1,2,4-triazin-6-yl]-3-methyl-5-(trifluoromethyl)phenol | 163.3 | |

TABLE 1-continued

NLRP3 inhibitory activity

| Example No. | Structure | Name | THP-1 pyroptosis assay IC$_{50}$ (nM) | Human whole blood IL-1β Assay IC$_{50}$ (nM) |
|---|---|---|---|---|
| 30 | 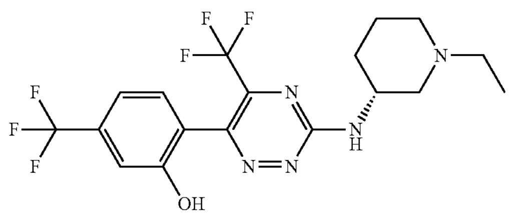 [SMILES: CCN1CCC[C@@H](Nc2nnc(-c3ccc(C(F)(F)F)cc3O)c(C(F)(F)F)n2)C1] | 2-[3-[[(3R)-1-Ethyl-3-piperidyl]amino]-5-(trifluoromethyl)-1,2,4-triazin-6-yl]-5-(trifluoromethyl) phenol; 2,2,2-trifluoroacetic acid | 111.3 | |
| 31 | 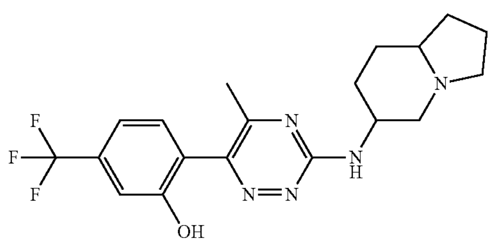 [SMILES: Cc1nc(NC2CCC3CCCN3C2)nnc1-c1ccc(C(F)(F)F)cc1O] | 2-[3-[[(6S or 6R, 8aS or 8aR)-1,2,3,5,6,7,8,8a-octahydroindolizin-6-yl]amino]-5-methyl-1,2,4-triazin-6-yl]-5-(trifluoromethyl) phenol | >1000 | |
| 32 | 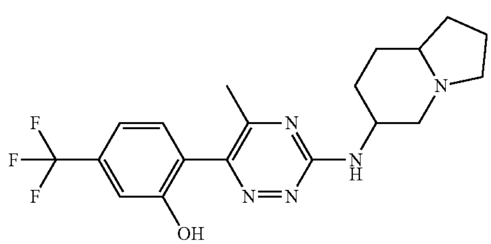 [SMILES: Cc1nc(NC2CCC3CCCN3C2)nnc1-c1ccc(C(F)(F)F)cc1O] | 2-[3-[[(6R or 6S, 8aS or 8aR)-1,2,3,5,6,7,8,8a-octahydroindolizin-6-yl]amino]-5-methyl-1,2,4-triazin-6-yl]-5-(trifluoromethyl) phenol | 16.1 | 36.5 |
| 33 | 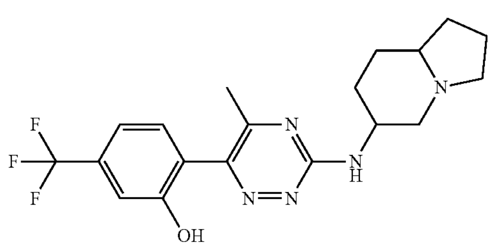 [SMILES: Cc1nc(NC2CCC3CCCN3C2)nnc1-c1ccc(C(F)(F)F)cc1O] | 2-[3-[[(6S or 6R, 8aR or 8aS)-1,2,3,5,6,7,8,8a-octahydroindolizin-6-yl]amino]-5-methyl-1,2,4-triazin-6-yl]-5-(trifluoromethyl) phenol | 46.1 | 300 |
| 34 | 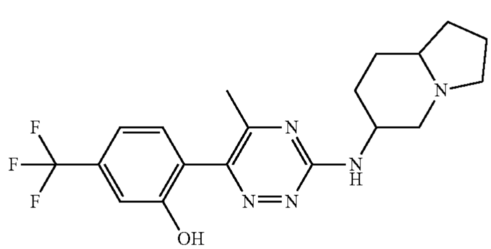 [SMILES: Cc1nc(NC2CCC3CCCN3C2)nnc1-c1ccc(C(F)(F)F)cc1O] | 2-[3-[[(6R or 6S, 8aR or 8aS)-1,2,3,5,6,7,8,8a-octahydroindolizin-6-yl]amino]-5-methyl-1,2,4-triazin-6-yl]-5-(trifluoromethyl) phenol | 208.8 | |

TABLE 2

Inhibitory activity at hERG

| Example No. | Structure | Name | hERG assay IC$_{50}$ (μM) |
|---|---|---|---|
| 4 | (structure) | 2-[3-[[(3R)-1-Ethyl-3-piperidyl]amino]-5-methyl-1,2,4-triazin-6-yl]-5-(trifluoromethyl)phenol | >10 μM |
| 7 | (structure) | 5-[3-[[(3R)-1-Ethyl-3-piperidyl]amino]-5-methyl-1,2,4-triazin-6-yl]-2,3-dihydrobenzofuran-4-ol | >20 μM |
| RE-A* | (structure) | 2-[6-[(1-ethyl-3-piperidyl)amino]-4-methyl-pyridazin-3-yl]-5-(trifluoromethyl)phenol | 1.2 μM |

*RE-A was described in WO20200234715.

The invention will now be illustrated by the following examples which have no limiting character.

In case the preparative examples are obtained as a mixture of enantiomers, the pure enantiomers can be obtained by methods described herein or by methods known to those skilled in the art, such as e.g. chiral chromatography or crystallization.

| Experimental Methods Abbreviations: | |
|---|---|
| ACN | acetonitrile |
| BBr$_3$ | boron tribromide |
| DIEA | diisopropylethylamine |
| DMSO | dimethylsulfoxide |
| EtOAc | ethyl acetate |
| NBS | N-Bromo Succinimide |
| PE | petroleum ether |
| Prep-HPLC | preparative high performance liquid chromatography |
| rac | racemic |
| RP | Reverse phase |
| TBME | tert-Butyl Methyl Ether |
| TFA | trifluoroacetic acid |

Analytical Methods

NMR spectra were run on Bruker 400 MHz spectrometers using ICON-NMR, under TopSpin program control. Spectra were measured at 298 K, unless indicated otherwise, and were referenced relative to the solvent resonance.

LC-MS Methods: Using SHIMADZU LCMS-2020, Agilent 1200 LC/G1956A MSD and Agilent 1200\G6110A, Agilent 1200 LC & Agilent 6110 MSD. Mobile Phase: A: 0.025% NH3·H2O in water (v/v); B: Acetonitrile. Column: Kinetex EVO C18 2.1×30 mm, 5 μm.

Purification Method (Step E)

Automated reversed phase column chromatography was carried out using a Gilson GX-281 system driven by a Gilson-322 pump module, Gilson-156 UV photometer detection unit and Gilson-281 fraction collector.

Phenomenex Gemini: 75*30 mm*3 um pH (water (0.1% TFA)-ACN): 3-4

Average particle size: 3 μm

The column was conditioned before use with 100% MeCN (2 min) then brought to 1% MeCN (in 0.8 min). Flow rate=25 mL/min.

| Separation runs: | | |
|---|---|---|
| Time (min) | A: water (10 mM TFA) | B: MeCN |
| 0 | 72% | 28% |
| 1.0 | 72% | 28% |
| 10.0 | 42% | 48% |
| 10.2 | 0% | 100% |
| 12.0 | 0% | 100% |
| 12.2 | 95% | 5% |
| 13.0 | 95% | 5% |

Purification Method (Step F)

Automated reversed phase column chromatography was carried out using a Gilson GX-281 system driven by a Gilson-322 pump module, Gilson-156 UV photometer detection unit and Gilson-281 fraction collector.

Phenomenex Gemini: 75*30 mm*3 um pH (water (0.1% TFA)-ACN): 3-4

Average particle size: 3 μm

The column was conditioned before use with 100% MeCN (2 min) then brought to 1% MeCN (in 0.8 min). Flow rate=25 mL/min.

| Separation runs: | | |
|---|---|---|
| Time (min) | A: water (10 mM TFA) | B: MeCN |
| 0 | 77% | 23% |
| 1.0 | 77% | 23% |
| 10.0 | 57% | 43% |
| 10.2 | 0% | 100% |
| 12.0 | 0% | 100% |
| 12.2 | 95% | 5% |
| 13.0 | 95% | 5% |

Detection wavelength: 220 and 254 nm. Before each new run, the cartridge was cleaned using the conditioning method.

BRIEF DESCRIPTION OF THE FIGURES

FIG. 1: Pulse pattern used to elicit outward K⁺ current at 35-37° C.

EXAMPLES

All examples and intermediates were prepared under nitrogen atmosphere if not specified otherwise.

Example 1: 2-[3-[[(3R)-1-Ethyl-3-piperidyl]amino]-1,2,4-triazin-6-yl]-3-methyl-5-(trifluoromethyl) phenol; 2,2,2-trifluoroacetic acid

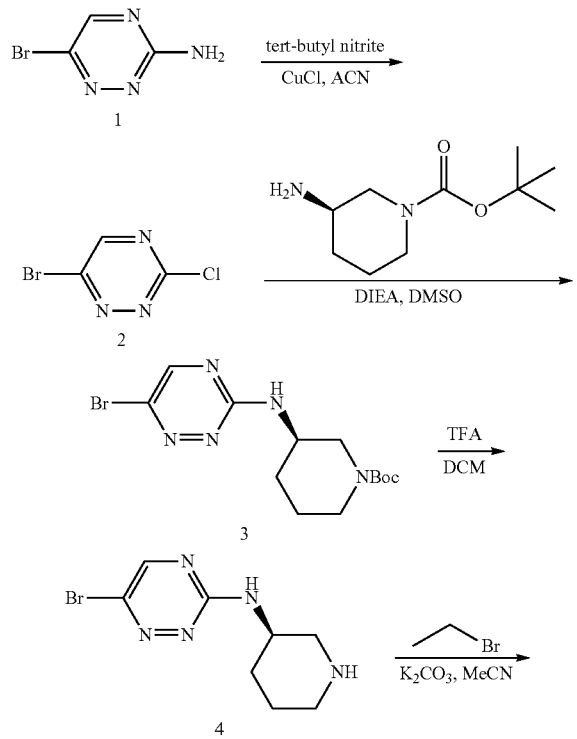

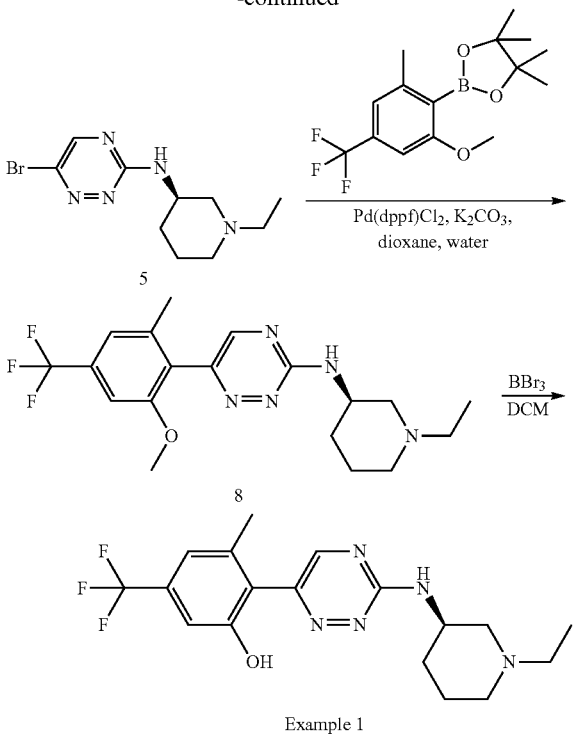

Example 1

Step A: 6-Bromo-3-chloro-1,2,4-triazine

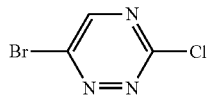

To a solution of 6-bromo-1,2,4-triazin-3-amine (5.0 g, 29 mmol, 1 eq) in ACN (100 mL) was added tert-butylnitrite (4.7 g, 46 mmol, 1.6 eq) and CuCl (3.7 g, 37 mmol, 1.3 eq). The mixture was stirred at 70° C. for 2 hours. The residue was concentrated in vacuum and purified by column chromatography (PE:EtOAc=1:0 to 10:1) to obtain the title compound (1.6 g, 29% yield) as yellow oil.

Step B: (R)-Tert-butyl 3-((6-bromo-1,2,4-triazin-3-yl)amino) piperidine-1-carboxylate

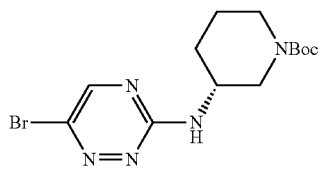

To a solution of tert-butyl (3R)-3-aminopiperidine-1-carboxylate (620 mg, 3.1 mmol, 1.2 eq) in DMSO (5 mL) was added DIEA (1.0 mL, 5.7 mmol, 2.2 eq) and 6-bromo-3-chloro-1,2,4-triazine (500 mg, 2.6 mmol, 1 eq). The mixture was stirred at 20° C. for 2 hours. The mixture was poured into water (100 mL) and extracted with EtOAc (30 mL*3).

The combined organic layers were washed with brine (20 mL), dried over anhydrous sodium sulfate, filtered, and the filtrate was concentrated under reduced pressure. The residue was purified by prep-TLC (SiO$_2$, PE/EtOAc=5/1) to afford the title compound (590 mg, 64% yield) as a yellow solid. LCMS: m/z 304.0, [M-C$_4$H$_9$+2+H]+, ESI pos.

Step C: 6-Bromo-N-[(3R)-3-piperidyl]-1,2,4-triazin-3-amine; 2,2,2-trifluoroacetic acid

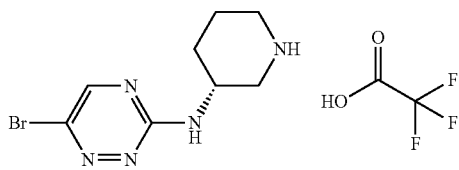 [SMILES: Brc1cnc(N[C@@H]2CCCNC2)nn1 ; O=C(O)C(F)(F)F]

To a solution of tert-butyl (3R)-3-[(6-bromo-1,2,4-triazin-3-yl)amino]piperidine-1-carboxylate (490 mg, 1.4 mmol, 1 eq) in CH$_2$Cl$_2$ (4 mL) was added TFA (1.0 mL). The mixture was stirred at 20° C. for 2 hours. The reaction was concentrated under reduced pressure to afford the title compound as yellow gum (TFA salt, 500 mg). LCMS: m/z 258.0 [M+H]$^+$, ESI pos.

Step D: 6-Bromo-N-[(3R)-1-ethyl-3-piperidyl]-1,2,4-triazin-3-amine

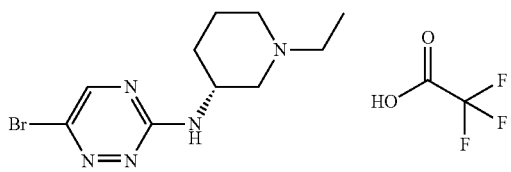 [SMILES: CCN1CCC[C@@H](Nc2ncc(Br)nn2)C1 ; O=C(O)C(F)(F)F]

To a solution of 6-bromo-N-[(3R)-3-piperidyl]-1,2,4-triazin-3-amine; 2,2,2-trifluoroacetic acid (100 mg, 0.3 mmol, 1 eq) in ACN (1 mL) was added K$_2$CO$_3$ (74 mg, 0.5 mmol, 2 eq) and ethyl bromide (0.02 mL, 0.3 mmol, 1.1 eq). The reaction mixture was stirred at 20° C. for 16 hours. Then, water (1 mL) was added to the mixture and purified by reversed-phase flash (0.1% TFA aqueous-ACN condition) to give the title compound (20 mg, 25% yield) as a yellow solid. LCMS: m/z 286.0 [M+H]$^+$, ESI pos.

Step E: N-[(3R)-1-ethyl-3-piperidyl]-6-[2-methoxy-6-methyl-4-(trifluoromethyl)phenyl]-1,2,4-triazin-3-amine; 2,2,2-trifluoroacetic acid

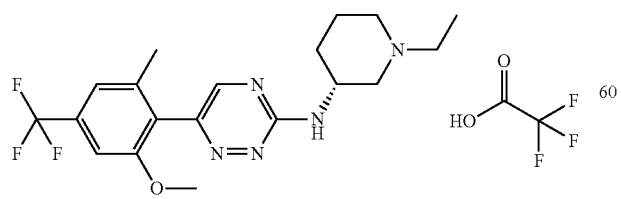

A mixture of 2-[2-methoxy-6-methyl-4-(trifluoromethyl)phenyl]-4,4,5,5-tetramethyl-1,3,2-dioxaborolane (320 mg, 1.0 mmol, 1.6 eq), 6-bromo-N-[(3R)-1-ethyl-3-piperidyl]-1,2,4-triazin-3-amine; 2,2,2-trifluoroacetic acid (250 mg, 0.6 mmol, 1 eq) and K$_2$CO$_3$ (463 mg, 4.4 mmol, 7 eq) in 1,4-dioxane (5 mL) and water (1 mL) was degassed and purged with nitrogen three times and Pd(dppf)Cl$_2$ (153 mg, 0.2 mmol, 0.3 eq) was added to the mixture. The mixture was stirred at 100° C. for 12 hours. Then, water (1 mL) was added to the mixture. The residue was purified by reversed-phase flash (0.1% TFA condition) twice and prep-HPLC (Method: Column 3_Phenomenex Luna C18 75*30 mm*3 um; Condition: water (0.1% TFA)-ACN; Begin B 28 End B 48; Gradient Time (min): 7; 100% B; Hold Time (min): 2; FlowRate (ml/min): 25) to afford the title compound as a yellow solid (TFA salt, 12 mg, 4% yield). LCMS: m/z 396.3 [M+H]$^+$, ESI pos.

Step F: 2-[3-[[(3R)-1-ethyl-3-piperidyl]amino]-1,2,4-triazin-6-yl]-3-methyl-5-(trifluoromethyl) phenol; 2,2,2-trifluoroacetic acid

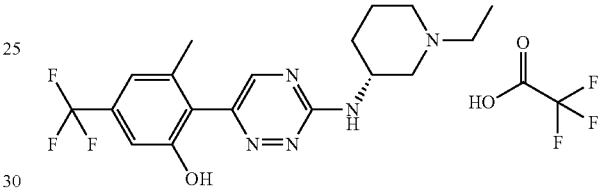

To a solution of N-[(3R)-1-ethyl-3-piperidyl]-6-[2-methoxy-6-methyl-4-(trifluoromethyl)phenyl]-1,2,4-triazin-3-amine; 2,2,2-trifluoroacetic acid (40 mg, 0.08 mmol, 1 eq) in CH$_2$Cl$_2$ (1 mL) was added BBr$_3$ (0.07 mL, 0.8 mmol, 10 eq) at −70° C. Afterwards, the mixture was stirred at 20° C. for 1 hour. Them, ice water (1 mL) was added to the mixture and the pH was adjusted to pH ~8 with NH$_3$·H$_2$O and the mixture was lyophilized. The residue was purified by prep-HPLC (Column 3_Phenomenex Luna C18 75*30 mm*3 um; Condition: water (0.1% TFA)-ACN; Begin B 23 End B 43; Gradient Time (min): 7; 100% B; Hold Time (min): 2; Flow Rate (mL/min): 25) to give the title compound as a yellow solid (TFA salt, 25 mg, 63% yield). LCMS: m/z 382.2 [M+H]$^+$, ESI pos.

Example 2: 5-Chloro-2-[3-[(1-ethyl-3-piperidyl)amino]-5-methyl-1,2,4-triazin-6-yl]phenol (rac)

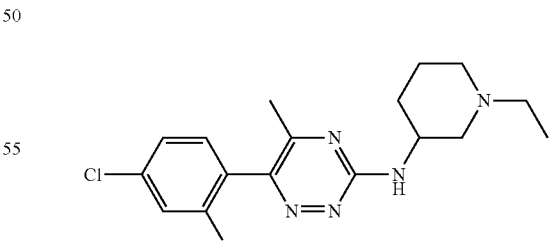

Step A: 6-Chloro-N-(1-ethyl-3-piperidyl)-5-methyl-1,2,4-triazin-3-amine

To a mixture of 3,6-dichloro-5-methyl-1,2,4-triazine (CAS #132434-82-3, 150 mg, 0.915 mmol, 1.0 eq) and 1-ethylpiperidin-3-amine (CAS #6789-94-2, 196 µL, 1.37 mmol, 1.5 eq) in 1,4-dioxane (3 mL) was added DIEA (160 µL, 1.37 mmol, 1.03 eq). The reaction mixture was stirred at room temperature for 16 hours. The reaction mixture was extracted with EtOAc. The organic layer was washed with brine. The aqueous layers were back extracted twice with EtOAc. The combined organic layers were dried over sodium sulfate, filtered and concentrated in vacuo. The crude product was adsorbed on ISOLUTE HM-N and purified by flash chromatography (silica gel, 12 g, EtOAc isocratic) to afford the title compound (221 mg, traces of dichloromethane) as a light yellow solid. m/z 256.1 [M+H]+, ESI pos.

Step B: 6-Chloro-N-(1-ethyl-3-piperidyl)-5-methyl-1,2,4-triazin-3-amine (rac)

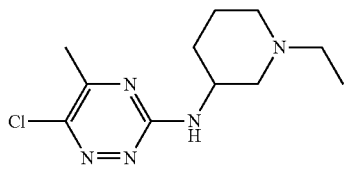 [SMILES: CCN1CCCC(Nc2nnc(Cl)c(C)n2)C1]

A mixture of aforementioned 6-chloro-N-(1-ethyl-3-piperidyl)-5-methyl-1,2,4-triazin-3-amine (40 mg, 0.156 mmol, 1.0 eq), (4-chloro-2-hydroxy-phenyl) boronic acid (CAS #1238196-66-1, 45.7 mg, 0.265 mmol, 1.7 eq), potassium carbonate (103 mg, 0.747 mmol, 4.8 eq) and 1,1'-bis(diphenylphosphino) ferrocene-palladium (ii) dichloride dichloromethane complex (14.8 mg, 0.018 mmol, 0.116 eq) in 1,4-dioxane (0.9 mL) and water (0.5 mL) was flushed with argon and stirred at 90° C. for 4 hours. The reaction mixture was cooled to room temperature and extracted with EtOAc. The aqueous layer was backextracted with EtOAc. The organic layers were washed with water and brine. The combined organic layers were dried over sodium sulfate, filtered over a pad of celite and concentrated in vacuo. The crude product was purified by prep-HPLC (column: Gemini NX, 12 nm, 5 µm, 100×30 mm; condition: ACN/water+0.1% TEA; APS 15 mins run time, gradient 20-40-55-100 ACN in water) to afford the title compound (19.9 mg, 33% yield) as an grey solid. m/z 348.3 [M+H]+, ESI pos.

Example 3:2-[3-[(3-Hydroxy-3-methyl-cyclobutyl)amino]-5-methyl-1,2,4-triazin-6-yl]-5-(trifluoromethyl) phenol

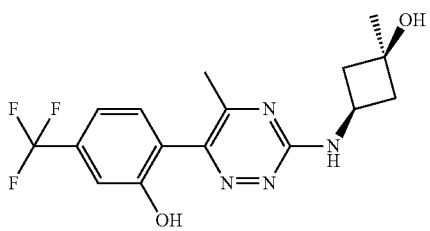 [SMILES: Cc1nc(N[C@H]2C[C@@](C)(O)C2)nnc1-c1ccc(C(F)(F)F)cc1O]

Step A: 3-[(6-chloro-5-methyl-1,2,4-triazin-3-yl)amino]-1-methyl-cyclobutanol

Similarly to example 3: To a mixture of 3,6-dichloro-5-methyl-1,2,4-triazine (CAS #132434-82-3, 200 mg, 1.22 mmol, 1.0 eq) and 3-amino-1-methyl-cyclobutanol hydrochloride (CAS #1820687-11-3, 251.7 mg, 1.83 mmol, 1.5 eq) in 1,4-dioxane (4 mL) was added DIEA (639 µL, 3.66 mmol, 3 eq). The reaction mixture was stirred at room temperature for 3 days. The reaction mixture extracted with EtOAc and water. The organic layer was washed with brine. The aqueous layers were back extracted four times with EtOAc. The combined organic layers were dried over sodium sulfate, filtered and concentrated in vacuo. The crude product (317 mg) was adsorbed on ISOLUTE HM-N and purified by flash chromatography (silica gel, 12 g, n-heptane/EtOAc with EtOAc gradient from 0 to 80%) to afford the title compound (159.4 mg, 90% pure) as a yellow solid. m/z 229.1 [M+H]+, ESI pos.

Step B: 3-[(6-Chloro-5-methyl-1,2,4-triazin-3-yl)amino]-1-methyl-cyclobutanol

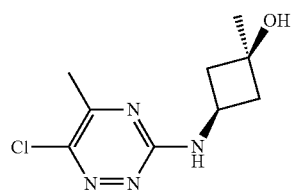

A mixture of aforementioned 3-[(6-chloro-5-methyl-1,2,4-triazin-3-yl)amino]-1-methyl-cyclobutanol (80 mg, 0.315 mmol, 1.0 eq), [2-hydroxy-4-(trifluoromethyl)phenyl]boronic acid (CAS #1072951-50-8, 109.9 mg, 0.534 mmol, 1.7 eq), potassium carbonate (207.9 mg, 1.50 mmol, 4.8 eq) and 1,1'-bis(diphenylphosphino) ferrocene-palladium (ii) dichloride dichloromethane complex (29.7 mg, 0.036 mmol, 0.116 eq) in 1,4-dioxane (1.9 mL) and water (0.9 mL) was flushed with argon and stirred at 90° C. for 16 hours. The reaction mixture was cooled to room temperature and extracted with EtOAc. The aqueous layer was back extracted with EtOAc. The organic layers were washed with water and brine. The combined organic layers were dried over sodium sulfate, filtered over a pad of celite and concentrated in vacuo. The crude product (297 mg) was purified by prep-HPLC (column: Column achiral 100 PEI, 5 µm, 250×20 mm; condition: 35% MeOH; SFC) to afford the title compound (98.9 mg, 78% yield) as a grey solid. m/z 355.2 [M+H]+, ESI pos.

Example 4:2-[3-[[(3R)-1-Ethyl-3-piperidyl]amino]-5-methyl-1,2,4-triazin-6-yl]-5-(trifluoromethyl) phenol

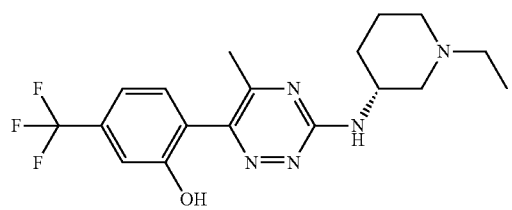 [SMILES: CCN1CCC[C@@H](Nc2nnc(-c3ccc(C(F)(F)F)cc3O)c(C)n2)C1]

Step A: 6-Chloro-N-[(3R)-1-ethyl-3-piperidyl]-5-methyl-1,2,4-triazin-3-amine

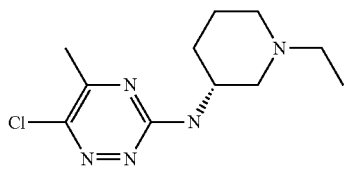 [SMILES: CCN1CCC[C@@H](Nc2nnc(Cl)c(C)n2)C1]

To a mixture of 3,6-dichloro-5-methyl-1,2,4-triazine (CAS #132434-82-3, 1.00 g, 6.1 mmol, 1.0 eq) and [(3R)-1-ethyl-3-piperidyl]amine (CAS #1020396-26-2, 1.24 g, 9.15 mmol, 1.5 eq) in 1,4-dioxane (20 mL) was added N,N-diisopropylethylamine (814 mg, 1.1 mL, 6.3 mmol, 1.03 eq). The reaction mixture was stirred at room temperature for 16 hours. The reaction mixture was extracted with dichloromethane and water. The organic layer was washed with brine. The aqueous layers were backextracted twice with dichloromethane. The combined organic layers were dried over sodium sulfate, filtered and concentrated in vacuo. The crude product was adsorbed on ISOLUTE HM-N and purified by flash chromatography (silica gel, 40 g, gradient 0% to 10% methanol in dichloromethane) to afford the title compound (1.32 g, 80% yield) as a green solid. m/z 256.3 [M+H]$^+$, ESI pos.

Step B: 2-[3-[[(3R)-1-Ethyl-3-piperidyl]amino]-5-methyl-1,2,4-triazin-6-yl]-5-(trifluoromethyl) phenol

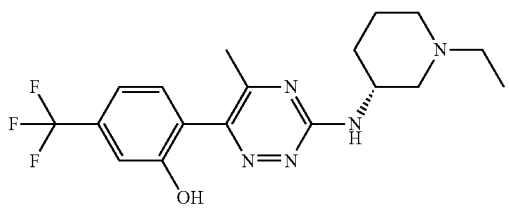 [SMILES: CCN1CCC[C@@H](Nc2nnc(-c3ccc(C(F)(F)F)cc3O)c(C)n2)C1]

A mixture of aforementioned 6-chloro-N-[(3R)-1-ethyl-3-piperidyl]-5-methyl-1,2,4-triazin-3-amine (Example 4, step A) (280 mg, 1.04 mmol, 1.0 eq), [2-hydroxy-4-(trifluoromethyl)phenyl]boronic acid (CAS #1072951-50-8, 365 mg, 1.77 mmol, 1.7 eq), potassium carbonate (690 mg, 4.99 mmol, 4.8 eq) and 1,1'-bis(diphenylphosphino) ferrocene-palladium (ii) dichloride dichloromethane complex (98 mg, 0.120 mmol, 0.115 eq) in 1,4-dioxane (6 mL) and water (3 mL) was flushed with argon and stirred at 85° C. for 16 hours. The reaction mixture was cooled to room temperature and extracted with EtOAc and half-saturated aq. NH$_4$Cl-solution. The aqueous layer was backextracted with EtOAc. The organic layers were washed with water and brine. The combined organic layers were dried over sodium sulfate, filtered and concentrated in vacuo. The crude product was adsorbed on ISOLUTE HM-N and purified by flash chromatography (silica gel, 25 g, gradient 0% to 10% methanol in dichloromethane). The residue was adsorbed on ISOLUTE HM-N and repurified by flash chromatography (silica gel, 25 g, gradient 0% to 100% (dichloromethane:methanol:NH$_4$OH 9:1:0.05) in dichloromethane). All fractions containing product were combined and concentrated in vacuo. The residue was triturated with EtOAc/heptane to afford the title compound (246 mg, 61% yield) as an off-white powder. m/z 382.3 [M+H]$^+$, ESI pos.

Example 5: 5-Chloro-2-[3-[[(3R)-1-ethyl-3-piperidyl]amino]-5-methyl-1,2,4-triazin-6-yl]phenol

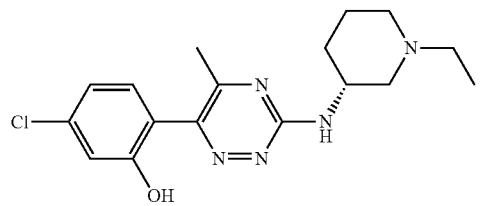 [SMILES: CCN1CCC[C@@H](Nc2nnc(-c3ccc(Cl)cc3O)c(C)n2)C1]

A mixture of 6-chloro-N-[(3R)-1-ethyl-3-piperidyl]-5-methyl-1,2,4-triazin-3-amine (Example 4, step A) (280 mg, 1.04 mmol, 1 eq), (4-chloro-2-hydroxy-phenyl) boronic acid (CAS #1238196-66-1, 305 mg, 1.77 mmol, 1.7 eq), potassium carbonate (690 mg, 4.99 mmol, 4.8 eq) and 1,1'-bis(diphenylphosphino) ferrocene-palladium (ii) dichloride dichloromethane complex (98 mg, 0.120 mmol, 0.115 eq) in 1,4-dioxane (6 mL) and water (3 mL) was flushed with argon and stirred at 85° C. overnight. The reaction mixture was cooled to room temperature and extracted with EtOAc and half-saturated aq. NH$_4$Cl-solution. The aqueous layer was backextracted with EtOAc. The organic layers were washed with water and brine. The combined organic layers were dried over sodium sulfate, filtered and concentrated in vacuo. The crude product was adsorbed on ISOLUTE HM-N and purified by flash chromatography (silica gel, 25 g, gradient 0% to 10% methanol in dichloromethane). The residue was adsorbed on ISOLUTE HM-N and repurified by flash chromatography (silica gel, 12 g, gradient 0% to 60% (dichloromethane:methanol:NH$_4$OH 9:1:0.05) in dichloromethane). All fractions containing product were combined and concentrated in vacuo. The residue was triturated with EtOAc/heptane to afford the title compound (204 mg, 55% yield) as off-white powder. m/z 348.3 [M+H]+, ESI pos

Example 6: 2-[3-[[(3R)-1-Ethyl-3-piperidyl]amino]-5-methyl-1,2,4-triazin-6-yl]-5-fluoro-phenol

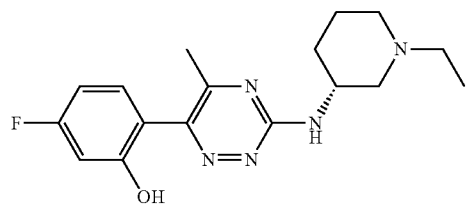 [SMILES: CCN1CCC[C@@H](Nc2nnc(-c3ccc(F)cc3O)c(C)n2)C1]

A mixture of aforementioned 6-chloro-N-[(3R)-1-ethyl-3-piperidyl]-5-methyl-1,2,4-triazin-3-amine (Example 4, step A) (80 mg, 0.313 mmol, 1 eq), (4-fluoro-2-hydroxyphenyl) boronic acid (CAS #850568-00-2, 85 mg, 0.545 mmol, 1.74 eq), potassium carbonate (205 mg, 1.48 mmol, 4.74 eq) and 1,1'-bis(diphenylphosphino) ferrocene-palladium (ii) dichloride dichloromethane complex (29 mg, 0.036 mmol, 0.114 eq) in 1,4-dioxane (1.8 mL) and water (0.900 mL) was flushed with argon and stirred at 90° C. for 2 hours. The reaction mixture was cooled to room temperature and extracted with EtOAc and water. The aqueous layer was backextracted with EtOAc. The organic layers were washed twice with water and once with brine. The combined organic layers were dried over sodium sulfate, filtered and concentrated in vacuo. The crude product was adsorbed on ISOLUTE HM-N and purified by flash chromatography (silica gel, 12 g, gradient 0% to 10% (methanol in dichloromethane) to afford the title compound (50 mg, 46% yield) as brown solid. m/z 332.3 [M+H]+, ESI pos Example 7:5-[3-[[(3R)-1-Ethyl-3-piperidyl]amino]-5-methyl-1,2,4-triazin-6-yl]-2,3-dihydrobenzofuran-4-ol

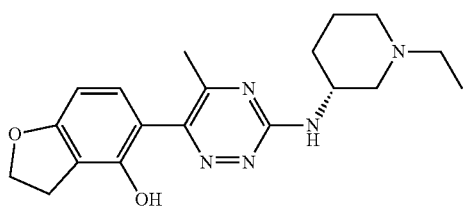

Step A: 5-Bromo-2,3-dihydrobenzofuran-4-ol

To a solution of 2,3-dihydrobenzofuran-4-ol (CAS #144822-82-2, 2.00 g, 14.7 mmol, 1 eq) in methanol (40 mL) was added pyridine tribromide (4.70 g, 14.7 mmol, 1 eq) at −40° C. The resulting mixture was stirred at −40° C. for 0.5 hour, then warmed to 20° C. and stirred for 16 hours. After reaction completion, the reaction mixture was dissolved in EtOAc (100 mL). The organic layer was washed with 1 N hydrochloric acid (100 mL×2), followed by brine (100 mL), dried over anhydrous sodium sulfate, filtered and the filtrate was concentrated under reduced pressure. The residue was purified by column chromatography (SiO$_2$, PE:EtOAc=15:1 to 10:1) to afford the title compound (1.90 g, 60% yield) as a yellow solid. LCMS: m/z 212.8 [M−H]$^-$, ESI neg.

Step B: 2-[(5-Bromo-2,3-dihydrobenzofuran-4-yl)oxymethoxy]ethyl-trimethylsilane

To a solution of 5-bromo-2,3-dihydrobenzofuran-4-ol (Example 7, Step A) (1.00 g, 4.65 mmol, 1.0 eq) in ACN (20 mL) was added K$_2$CO$_3$ (1.29 g, 9.3 mmol, 2.0 eq). The mixture was stirred at 20° C. for 0.5 hour and 2-(trimethylsilyl) ethoxymethyl chloride (0.99 mL, 5.58 mmol, 1.2 eq) was added to the mixture by drop wise. The mixture was stirred at 20° C. for 2 hours. TLC (PE:EtOAc=10:1) showed the starting material was consumed up and another main spot was formed. The mixture was quenched with water (100 mL) and extracted with EtOAc (100 mL×3). The organic phase was washed with brine (150 mL), dried over anhydrous sodium sulfate, filtered and the filtrate was concentrated under reduced pressure. The residue was purified by column chromatography (SiO$_2$, PE:EtOAc=20:1 to 15:1) to the title compound (1.30 g, 81% yield) as yellow oil. 1H NMR (400 MHz, DMSO-d$_6$) δ=7.30 (d, 1H), 6.49 (d, 1H), 5.19 (s, 2H), 4.54 (t, 2H), 3.87-3.74 (m, 2H), 3.32-3.26 (m, 2H), 0.94-0.86 (m, 2H), −0.01--0.05 (m, 9H).

Step C: Trimethyl-[2-[[5-(4,4,5,5-tetramethyl-1,3,2-dioxaborolan-2-yl)-2,3-dihydrobenzofuran-4-yl]oxymethoxy]ethyl]silane To a solution of 2-[(5-bromo-2,3-dihydrobenzofuran-4-yl)oxymethoxy]ethyl-trimethylsilane (1.20 g, 3.48 mmol, 1.0 eq) in isopropyl acetate (20 mL) was added bis(pinacolato)diboron (1.06 g, 4.17 mmol, 1.2 eq), anhydrous AcOK (0.75 g, 7.65 mmol, 2.2 eq), Xphos (166 mg, 0.350 mmol, 0.100 eq) and XPhos Pd G3 (295 mg, 0.350 mmol, 0.100 eq). The mixture was degassed with N$_2$ three times and stirred at 80° C. 12 hours under N$_2$. TLC (PE:EtOAc=20:1) showed the starting material was consumed and one new spot was detected. The mixture was quenched with water (30 mL) and extracted with EtOAc (30 mL×3). The organic phase was washed with brine (30 mL×2), dried over anhydrous sodium sulfate, filtered and the filtrate was concentrated under reduced pressure. The residue was first purified by column chromatography (SiO2, PE:EtOAc=80:1 to 50:1), followed by reversed-phase flash (CombiFlash 0.1% NH$_3$·H$_2$O aqueous-ACN) and follow up lyophilization to afford the title compound (288.3 mg, 20% yield) as colorless oil. LCMS: m/z 393.1 [M+H]$^+$, ESI pos.

Step D: N-[(3R)-1-Ethyl-3-piperidyl]-5-methyl-6-[4-(2-trimethylsilylethoxymethoxy)-2,3-dihydrobenzofuran-5-yl]-1,2,4-triazin-3-amine A mixture of aforementioned 6-chloro-N-[(3R)-1-ethyl-3-piperidyl]-5-methyl-1,2,4-triazin-3-amine (Example 4, step A) (25 mg, 0.098 mmol, 1.0 eq), trimethyl-[2-[[6-(4,4,5,5-tetramethyl-1,3,2-dioxaborolan-2-yl)-2,3-dihydrobenzofuran-4-yl]oxymethoxy]ethyl]silane (53.7 mg, 0.137 mmol, 1.4 eq), potassium carbonate (60.8 mg, 0.440 mmol, 4.5 eq) and 1,1'-bis(diphenylphosphino) ferrocene-palladium (ii) dichloride dichloromethane complex (CAS #95464 May 4, 9.58 mg, 0.012 mmol, 0.120 eq) in 1,4-dioxane (1 mL) and water (0.5 mL) was flushed with argon and stirred at 90° C. for 6 hours and 10 hours at 23° C. The reaction mixture was cooled to room temperature and quenched with water (10 mL) and saturated aq. NH$_4$Cl-solution (10 mL) and then extracted with dichloromethane (2×40 mL). The combined organic layers were washed with brine (20 mL), dried over sodium sulfate, filtered and concentrated in vacuo. The crude product was obtained as a brown oil (85 mg, 70% purity) and directly used in the next step without further purification. LCMS: m/z 486.4 [M+H]$^+$, ESI pos.

Step E: 5-[3-[[(3R)-1-Ethyl-3-piperidyl]amino]-5-methyl-1,2,4-triazin-6-yl]-2,3-dihydrobenzofuran-4-ol To a solution of N-[(3R)-1-ethyl-3-piperidyl]-5-methyl-6-[4-(2-trimethylsilylethoxymethoxy)-2,3-dihydrobenzofuran-5-yl]-1,2,4-triazin-3-amine (85 mg, 0.123 mmol, 1 eq) in dichloromethane, extra dry (5 mL) and methanol (1 mL) was added at room temperature 4 M HCl in dioxane (123 μL, 0.49 mmol, 4 eq). The mixture was stirred at 23° C. for 2 hours. After reaction completion, the mixture was diluted with dichloromethane (20 mL), ice water (20 mL) and sat. NaHCO$_3$ (20 mL). Then, extracted with dichloromethane (3×20 mL). The combined organic extracts were dried over Na$_2$SO$_4$, filtered and concentrated in vacuo. The crude brown material was purified using RP HPLC (column: Gemini NX, 12 nm, 5 μm, 100×30 mm, acetonitrile/water+ 0.1 triethylamine) to afford the title compound (12 mg, 27%) as light yellow amorph freeze-dried solid. LCMS: m/z 356.3 [M+H]$^+$, ESI pos.

Example 8: 3-[3-[[(3R)-1-Ethyl-3-piperidyl]amino]-5-methyl-1,2,4-triazin-6-yl]bicyclo[4.2.0]octa-1(6),2,4-trien-2-ol

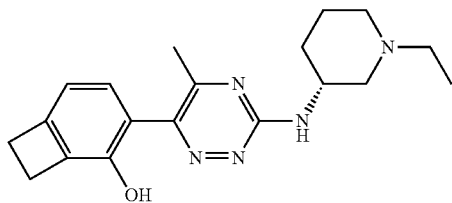 [SMILES: CCN1CCC[C@@H](Nc2nnc(-c3ccc4c(c3O)CC4)c(C)n2)C1]

Step A: 2-[(3-Bromo-2-bicyclo[4.2.0]octa-1,3,5-trienyl)oxymethoxy]ethyl-trimethyl-silane To a solution of 3-bromobicyclo[4.2.0]octa-1,3,5-trien-2-ol (WO2021150574, 195 mg, 0.98 mmol, 1.0 eq) in DMF (5 mL) was added potassium carbonate (302 mg, 2.19 mmol, 2.20 eq) at room temperature. The resulting mixture was sonicated then 2-(trimethylsilyl) ethoxymethyl chloride (200 µL, 1.13 mmol, 1.15 eq) was added and the reaction mixture was stirred at room temperature for 16 h. Then potassium carbonate (140 mg, 1.01 mmol, 1.03 eq) followed by 2-(trimethylsilyl) ethoxymethyl chloride (0.1 mL, 0.570 mmol, 0.58 eq) was added and the reaction mixture was stirred at room temperature for 2 h. The reaction mixture was diluted with EtOAc (50 mL) and 50 v % brine (100 mL) and the separated aqueous layer was further extracted with EtOAc (2×50 mL). The combined organic layers were washed with 50 v % brine (100 mL), dried (MgSO4), filtered and concentrated. The crude reaction mixture was purified by column chromatography on silica gel (40 g, 0-20% MTBE: isoHexane) to afford the title compound (345.0 mg, 100% yield) as a colourless oil. $^1$H NMR (500 MHZ, DMSO) δ 7.39 (d, 1H), 6.67 (d, 1H), 5.27 (s, 2H), 3.72 (dd, 2H), 3.28 (dd, 2H), 3.05 (dd, 2H), 0.91-0.85 (m, 2H), −0.05 (s, 9H). LCMS no ionization.

Step B: Trimethyl-[2-[[3-(4,4,5,5-tetramethyl-1,3,2-dioxaborolan-2-yl)-2-bicyclo[4.2.0]octa-1,3,5-trienyl]oxymethoxy]ethyl]silane 2-[(3-Bromo-2-bicyclo[4.2.0]octa-1,3,5-trienyl)oxymethoxy]ethyl-trimethyl-silane (103.0 mg, 0.270 mmol, 1 eq), bis(pinacolato)diboron (81.0 mg, 0.320 mmol, 1.2 eq) and potassium acetate (111.0 mg, 1.13 mmol, 4.25 eq) in isopropyl acetate (8 mL) was sparged (bubbling nitrogen for 10 min whilst sonicating). XPhos Pd G3 (46.0 mg, 0.05 mmol, 0.05 eq) and XPhos (11.0 mg, 0.02 mmol, 0.02 eq) were added and the reaction mixture was stirred at 90° C. for 16 h. The reaction mixture was concentrated, and the resulting residue was purified by chromatography on silica gel (40 g, 0-20% MTBE: isoHexane) to afford the title compound (199 mg, 41% yield) as a light-yellow oil. 1H NMR (500 MHZ, CDCl$_3$) δ 7.57 (d, 1H), 6.71 (d, 1H), 5.25 (s, 2H), 3.81-3.71 (m, 2H), 3.30 (dd, 2H), 3.18-3.05 (m, 2H), 1.33 (s, 12H), 0.97-0.92 (m, 2H), −0.03 (s, 9H). LCMS no ionization.

Step C: N-[(3R)-1-Ethyl-3-piperidyl]-5-methyl-6-[2-(2-trimethylsilylethoxymethoxy)-3-bicyclo[4.2.0]octa-1(6),2,4-trienyl]-1,2,4-triazin-3-amine A mixture of aforementioned 6-chloro-N-[(3R)-1-ethyl-3-piperidyl]-5-methyl-1,2,4-triazin-3-amine (Example 4, step A) (53 mg, 0.197 mmol, 1.0 eq), trimethyl-[2-[[3-(4,4,5,5-tetramethyl-1,3,2-dioxaborolan-2-yl)-2-bicyclo[4.2.0]octa-1(6),2,4-trienyl]oxymethoxy]ethyl]silane (Example 4, step B) (103.74 mg, 0.276 mmol, 1.4 eq), potassium carbonate (122.4 mg, 0.886 mmol, 4.5 eq) in 1,4-dioxane (2.52 mL) and water (1.26 mL). The mixture was flushed with argon and 1,1'-bis(diphenylphosphino) ferrocene-palladium (ii) dichloride dichloromethane complex (CAS #95464 May 4, 24.1 mg, 0.030 mmol, 0.120 eq) was flushed again with argon. The resulting mixture was stirred at 90° C. for 5 hours. The reaction mixture was cooled to room temperature and quenched with water (10 mL) and saturated aq. NH$_4$Cl-solution (10 mL) and then extracted with dichloromethane (2×40 mL). The combined organic layers were washed with brine (20 mL), dried over Na$_2$SO$_4$, filtered and concentrated in vacuo. The crude product (200 mg) was purified by flash chromatography (SiO$_2$, 12 g, heptane: EtOAc=0 to 50% EtOAc followed by EtOAc:MeOH=9:1) to afford the title compound (75 mg, 78%) as a light brown oil. LCMS: m/z 470.7 [M+H]$^+$, ESI pos.

Step D: 3-[3-[[(3R)-1-Ethyl-3-piperidyl]amino]-5-methyl-1,2,4-triazin-6-yl]bicyclo[4.2.0]octa-1(6),2,4-trien-2-ol To a solution of N-[(3R)-1-ethyl-3-piperidyl]-5-methyl-6-[4-(2-trimethylsilylethoxymethoxy)-2,3-dihydrobenzofuran-5-yl]-1,2,4-triazin-3-amine (75 mg, 0.160 mmol, 1 eq) in dichloromethane (4 mL) and methanol (1 mL) was added at room temperature 4 M HCl in dioxane (399.2 µL, 1.60 mmol, 10 eq). The mixture was stirred at 23° C. for 16 h. After reaction completion, the mixture was diluted with dichloromethane (20 mL), ice water (20 mL) and sat. NaHCO$_3$ (20 mL). The combined organic extracts were dried over Na$_2$SO$_4$, filtered and concentrated in vacuo. The crude material (77 mg) was purified using RP HPLC (column: YMC-triart C$_{18}$, 12 nm, 5 µm, 100×30 mm, acetonitrile/water+0.1 triethylamine) to afford the title compound (32 mg, 59%) off-white amorph freeze-dried solid. LCMS: m/z 340.2 [M+H]$^+$, ESI pos.

Example 9: 2-[3-[[(3R)-1-Ethyl-3-piperidyl]amino]-5-methyl-1,2,4-triazin-6-yl]-3-fluoro-5-(trifluoromethyl) phenol

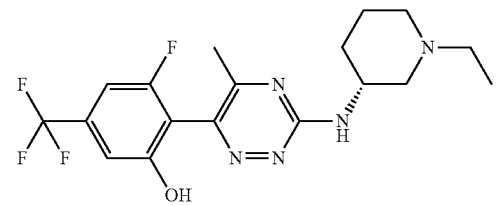 [SMILES: CCN1CCC[C@@H](Nc2nnc(-c3c(O)cc(C(F)(F)F)cc3F)c(C)n2)C1]

Step A: 2-Bromo-6-fluoro-4-(trifluoromethyl) aniline

To a solution of commercially available 2-fluoro-4-(trifluoromethyl) aniline (25.0 g, 140 mmol, 1.00 eq) in DMF (300 mL) was added NBS (26.1 g, 147 mmol, 1.05 eq) at −10° C. The mixture was stirred at 25° C. for 12 h. The reaction mixture was diluted with EtOAc (500 mL) and extracted. The organic phase was washed with brine (500 mL*3), dried over Na$_2$SO$_4$, filtered and concentrated in vacuum. The residue was purified by column chromatography (SiO$_2$, Petroleum ether/Ethyl acetate=1/0 to 10/1) to afford the title compound (36.0 g, 99.9% yield) as yellow oil. LCMS: m/z 257.9 [M+H]$^+$, ESI pos.

Step B: 2-Fluoro-6-(4,4,5,5-tetramethyl-1,3,2-dioxaborolan-2-yl)-4-(trifluoromethyl) aniline To a solution of compound 2-bromo-6-fluoro-4-(trifluoromethyl) aniline (30.0 g, 116 mmol, 1.00 eq) in dioxane (500 mL) was added 4,4,5,5-tetramethyl-2-(4,4,5,5-tetramethyl-1,3,2-dioxaborolan-2-yl)-1,3,2-dioxaborolane (59.1 g, 233 mmol, 2.00 eq), KOAc (28.5 g, 291 mmol, 2.50 eq) and Pd(dppf)Cl$_2$·CH$_2$Cl$_2$ (9.50 g, 11.6 mmol, 0.10 eq) under N$_2$. The mixture was stirred at 100° C. for 3 h. The reaction was concentrated in vacuum. The residue diluted with EtOAc (1000 mL) and extracted. The organic phase was washed with brine (1000 mL), dried over Na$_2$SO$_4$, filtered and concentrated in vacuum to afford the title compound (45.0 g) as black oil, which was used directly in next step. LCMS: m/z 306.1 [M+H]$^+$, ESI pos.

Step D: 2-Amino-3-fluoro-5-(trifluoromethyl) phenol

To a solution of aforementioned 2-fluoro-6-(4,4,5,5-tetramethyl-1,3,2-dioxaborolan-2-yl)-4-(trifluoromethyl) aniline (45.0 g, 148 mmol, 1.00 eq) in THF (600 mL) was added NaOH (2M, 221 mL, 3.00 eq) and H$_2$O$_2$ (100 g, 885 mmol, 85.0 mL, 30.0% purity, 6.00 eq) at 0° C. and the reaction was stirred for 3 hrs at 25° C. The reaction was diluted with EtOAc (1500 mL) and extracted. The organic phase was washed with aqueous Na2SO3 solution (1500 mL*3), dried over Na$_2$SO$_4$, filtered and concentrated under reduced pressure to give a residue. The crude product was purified by reversed-phase HPLC (0.1% formic acid condition) to afford the title compound (11.0 g, 38% yield) as a brown solid. LCMS: m/z 196.0 [M+H]+, ESI pos.

Step E: 3-Fluoro-2-iodo-5-(trifluoromethyl) phenol

To a solution of compound 2-amino-3-fluoro-5-(trifluoromethyl) phenol (11.0 g, 56.4 mmol, 1.00 eq) and H$_2$SO$_4$ (40.5 g, 404 mmol, 22.0 mL, 7.17 eq) in H$_2$O (200 mL) and acetone (50.0 mL) was added NaNO$_2$ (7.78 g, 113 mmol, 2.00 eq) at 0° C. and the reaction was stirred for 30 min at 0° C. Then CuI (26.8 g, 141 mmol, 2.50 eq) and NaI (21.1 g, 141 mmol, 2.50 eq) were added to the reaction at 0° C. and the reaction was stirred for 1.5 h at 0° C. After reaction completion, water (500 mL) was added to the reaction mixture. The water phase was washed with EtOAc (300 mL*2). The combined organic layers were washed with brine (300 mL*2), dried over Na$_2$SO$_4$, filtered and concentrated under reduced pressure to give a residue. The residue was purified by column chromatography (SiO$_2$, Petroleum ether/Ethyl acetate=1/0 to 10/1) to afford the title compound (20.0 g) as brown oil. 1H NMR (400 MHZ, CDCl$_3$) δ=7.04 (s, 1H), 6.89 (dd, 1H), 6.76 (s, 1H).

Step F: 1-(Ethoxymethoxy)-3-fluoro-2-iodo-5-(trifluoromethyl)benzene

To a solution of compound 3-fluoro-2-iodo-5-(trifluoromethyl) phenol (20.0 g, 65.4 mmol, 1.00 eq) and chloromethoxyethane (9.27 g, 98.0 mmol, 9.09 mL, 1.50 eq) in DMF (200 mL) was added Cs$_2$CO$_3$ (31.9 g, 98.0 mmol, 1.50 eq) and the mixture was stirred at 25° C. for 2 h. After reaction completion, EtOAc (500 mL) was added and the phase were separated and extracted. The organic phase was washed with brine (500 mL*3), dried over Na$_2$SO$_4$, filtered and concentrated under reduced pressure to give a residue which was purified by column chromatography (SiO$_2$, Petroleum ether/Ethyl acetate=1/0 to 10/1) to afford the title compound (10.0 g, 42% yield) as colorless oil. 1H NMR (400 MHZ, CDCl$_3$): δ=7.15 (s, 1H), 7.00 (dd, 1H), 5.36 (s, 2H), 3.78 (q, 2H), 1.24 (t, 3H).

Step G: 2-[2-(Ethoxymethoxy)-6-fluoro-4-(trifluoromethyl)phenyl]-4,4,5,5-tetramethyl-1,3,2-dioxaborolane To a solution of 1-(ethoxymethoxy)-3-fluoro-2-iodo-5-(trifluoromethyl)benzene (10.0 g, 27.5 mmol, 1.00 eq) and 2-isopropoxy-4,4,5,5-tetramethyl-1,3,2-dioxaborolane (15.3 g, 82.4 mmol, 16.8 mL, 3.00 eq) in THF (100 mL) was added n-BuLi (2.50 M, 27.5 mL, 2.50 eq) at −70° C. and the reaction was stirred for 1 h at −70° C. After reaction completion, was aq. NH$_4$Cl solution (300 mL) added and the mixture was stirred for 10 min, extracted with EtOAc (200 mL*2). The combined organic layers were washed with brine (300 mL), dried over Na$_2$SO$_4$, filtered and concentrated under reduced pressure to give a residue. The residue was purified by prep-HPLC (Column: Welch Ultimate XB-CN 250*50*10 um; mobile phase: [Hexane-EtOH]; B %: 0%-0%, 7 min) to afford the title compound (7.00 g, 60% yield, 86.3% purity) as a white solid. $^1$H NMR (400 MHz, CDCl$_3$): δ=7.10 (s, 1H), 6.94 (d, 1H), 5.24 (s, 2H), 3.73 (q, 2H), 1.39 (s, 12H), 1.22 (t, 3H).

Step H: 6-[2-(Ethoxymethoxy)-6-fluoro-4-(trifluoromethyl)phenyl]-N-[(3R)-1-ethyl-3-piperidyl]-5-methyl-1,2,4-triazin-3-amine A mixture of aforementioned 6-chloro-N-[(3R)-1-ethyl-3-piperidyl]-5-methyl-1,2,4-triazin-3-amine (Example 4, step A) (67 mg, 0.262 mmol, 1 eq), 2-[2-(ethoxymethoxy)-6-fluoro-4-(trifluoromethyl)phenyl]-4,4,5,5-tetramethyl-1,3,2-dioxaborolane (221.9 mg, 0.524 mmol, 2 eq), potassium carbonate (144.8 mg, 1.05 mmol, 4 eq) in 1,4-dioxane (1.6 mL) and water (0.4 mL). The mixture was flushed with argon for 5 min and SPhos Pd G3 (CAS #1445085-82-4, 0.66 mg, 0.039 mmol, 0.150 eq) was flushed again with argon. The resulting mixture was stirred at 120° C. for 2 h in the microwave. After reaction completion, the reaction mixture was cooled to room temperature and quenched with water (30 mL) and saturated aq. NH$_4$Cl-solution (30 mL) and then extracted with dichloromethane (2×30 mL). The combined organic layers were washed with brine (30 mL), dried over Na$_2$SO$_4$, filtered and concentrated in vacuo. The crude product (140 mg, brown oil, 80% purity) was submitted to the next step. LCMS: m/z 458.5 [M+H]$^+$, ESI pos.

Step I: 2-[3-[[(3R)-1-Ethyl-3-piperidyl]amino]-5-methyl-1,2,4-triazin-6-yl]-3-fluoro-5-(trifluoromethyl) phenol To a solution of aforementioned 6-[2-(Ethoxymethoxy)-6-fluoro-4-(trifluoromethyl)phenyl]-N-[(3R)-1-ethyl-3-piperidyl]-5-methyl-1,2,4-triazin-3-amine (Example 9, step H) (140 mg, 0.245 mmol, 1 eq) and dichloromethane (5 mL) was added under ice cooling TFA (566 µL, 7.34 mmol, 30 eq) dropwise. The reaction mixture was stirred at 0° to +23° C. for 4 h. After complete conversion, the solvent was evaporated. The resulting residue was dissolved in dichloromethane (30 mL), a sat. NaHCO₃ solution (30 mL) was added and extracted. The organic phase was separated and washed with water (20 mL) and brine (20 mL). The aqueous phases were back-extracted with dichloromethane (2×30 mL). The combined organic layers were dried over Na2SO4, filtered and concentrated in vacuo. The residue (190 mg) was purified by flash chromatography (SiO₂, 12 g, gradient 0% to 100% (dichloromethane:MeOH:NH₄OH 110:10:1) in dichloromethane) followed by further purification on preparative RP-HPLC (column: YMC-Triart C₁₈, 12 nm, 5 μm, 100×30 mm, acetonitrile/water+0.1 triethylamine) to afford the title compound (51 mg, 50%) as an off-white amorph freeze-dried solid. LCMS: m/z 400.4 [M+H]⁺, ESI pos.

Example 10 and 11:2-[3-[[(3R)-1-tert-Butyl-3-piperidyl]amino]-5-methyl-1,2,4-triazin-6-yl]-5-(trifluoromethyl) phenol and 2-[3-[[(3S)-1-tert-Butyl-3-piperidyl]amino]-5-methyl-1,2,4-triazin-6-yl]-5-(trifluoromethyl) phenol

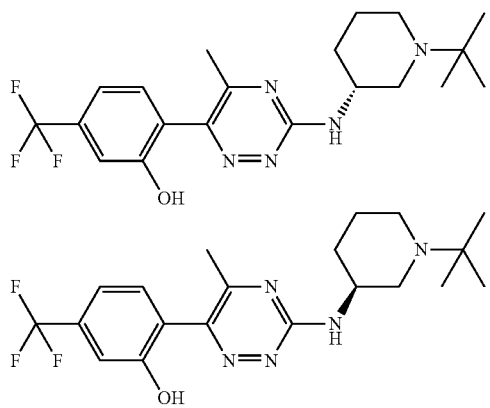

Step A: (rac)-N-(1-tert-Butyl-3-piperidyl)-6-chloro-5-methyl-1,2,4-triazin-3-amine To a mixture of commercially available 3,6-dichloro-5-methyl-1,2,4-triazine (CAS #132434-82-3, 250 mg, 1.45 mmol, 1.0 and commercially available (1-tert-butyl-3-piperidyl)amine; hydrochloride (CAS #2243513-25-7, 418.7 mg, 2.17 mmol, 1.50 eq) in 1,4-dioxane (4.75 mL) was added N,N-diisopropylethylamine (514 µL, 2.94 mmol, 2.03 eq). The reaction mixture was stirred at room temperature 1 hour followed by 22 h at 80° C. After reaction completion, the reaction mixture was cooled to room temperature and extracted with dichloromethane and water. The organic layers were washed with water and brine. The combined organic layers were dried over Na₂SO₄, filtered and concentrated in vacuo. The crude product was adsorbed on ISOLUTE HM-N and purified by flash chromatography (silica gel, 40 g, gradient 0% to 10% methanol in dichloromethane) the title product (273 mg, 66%) as green viscous oil. LCMS: m/z 284.3 [M+H]⁺, ESI pos.

Step B: 2-[3-[(1-tert-Butyl-3-piperidyl)amino]-5-methyl-1,2,4-triazin-6-yl]-5-(trifluoromethyl) phenol A mixture of aforementioned (rac)-N-(1-tert-Butyl-3-piperidyl)-6-chloro-5-methyl-1,2,4-triazin-3-amine (273 mg, 0.962 mmol, 1.0 eq), [2-hydroxy-4-(trifluoromethyl)phenyl] boronic acid (336.8 mg, 1.64 mmol, 1.7 eq), potassium carbonate (638.1 mg, 4.62 mmol, 4.8 eq) and 1,1'-bis(diphenylphosphino) ferrocene-palladium (ii) dichloride dichloromethane complex (90.3 mg, 0.111 mmol, 0.115 eq) in 1,4-dioxane (5.5 mL) and water (2.75 mL) was flushed with argon and stirred at 85° C. for 5 h. After complete conversion, the reaction mixture was cooled to room temperature and extracted with ethyl acetate (30 mL) and half-saturated NH₄Cl-solution (4 mL). The aqueous layer was back-extracted with ethyl acetate (30 mL). The organic layers were washed with water (4 mL) and brine (4 mL). The combined organic layers were dried over Na₂SO₄, filtered and concentrated in vacuo. The crude material was adsorbed on ISOLUTE HM-N and purified by flash chromatography (silica gel, 12 g, MeOH in dichloromethane 0 to 10%) to give the title product (316 mg, 80%) as light brown solid. LCMS: m/z 410.5 [M+H]⁺, ESI pos.

The crude material was submitted to chiral HPLC (column: chiralcel OJ, MeOH 5%+0.2% trimethylamine, SFC) to afford the first enantiomer 10 as a light brown solid (144 mg, 100% ee, contains 6% MeOH) and the second enantiomer 11 as a light brown solid (116 mg, 90% ee, contains 10% MeOH).

Optical Rotations:

Example 10: [α]²⁰ D=−17.47 (c=0.161 g/100 mL, MeOH)

Example 11: [α]²⁰ D=+18.58 (c=0.120 g/100 mL, MeOH)

Example 12:4-[3-[[(3R)-1-Ethyl-3-piperidyl]amino]-5-methyl-1,2,4-triazin-6-yl]-3-hydroxy-benzonitrile

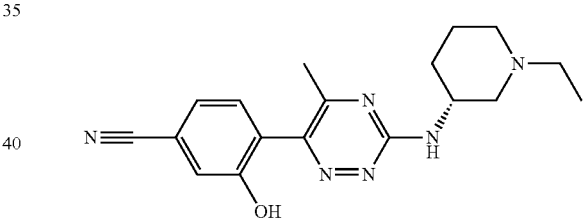

A mixture of aforementioned 6-chloro-N-[(3R)-1-ethyl-3-piperidyl]-5-methyl-1,2,4-triazin-3-amine (Example 4, step A) (120 mg, 0.469 mmol, 1 eq), commercially available 4-cyano-2-hydroxy-phenyl) boronic acid (CAS #n/a, 130.29 mg, 0.800 mmol, 1.7 eq), potassium carbonate (311.3 mg, 2.25 mmol, 4.8 eq) and 1,1'-bis(diphenylphosphino) ferrocene-palladium (ii) dichloride dichloromethane complex (44.2 mg, 0.054 mmol, 0.115 eq) in 1,4-dioxane (2.8 mL) and water (1.4 mL) was flushed with argon and stirred at 85° C. overnight. The reaction mixture was cooled to room temperature and extracted with ~15 mL EtOAc and ~15 mL half-saturated NH₄Cl-solution. The aqueous layer was back-extracted with ~15 mL EtOAc. The organic layers were washed with ~10 mL water and ~10 mL brine. The combined organic layers were dried over Ns2SO4, filtered and concentrated in vacuo. The crude product was adsorbed on ISOLUTE HM-N and purified by flash chromatography (silica gel, 4 g, gradient 0% to 10% methanol in dichloromethane) to afford the title compound (120 mg, 72%) as light brown powder. LCMS: m/z 333.9 [M+H]⁺, ESI pos.

Example 13: 2-[3-[[(3R,5S)-5-Fluoro-1-methyl-3-piperidyl]amino]-5-methyl-1,2,4-triazin-6-yl]-5-(trifluoromethyl) phenol

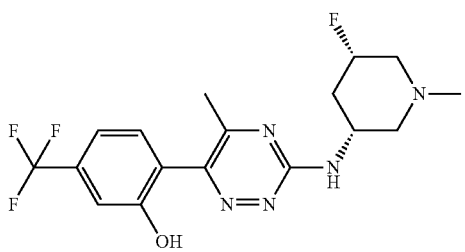

Step A: N-[(3R,5S)-5-Fluoro-1-methyl-3-piperidyl] carbamic acid tert-butyl ester To a solution of commercially available N-[(3R,5S)-5-fluoro-3-piperidyl]carbamic acid tert-butyl ester (CAS #1363378-08-8, 469 mg, 2.15 mmol, 1.0 eq) in tetrahydrofuran, extra dry (10 mL) was added N,N-diisopropylethylamine (938 µL, 5.37 mmol, 2.5 eq) followed by dropwise addition of iodomethane (161.2 µL, 2.58 mmol, 1.2 eq) The solution was stirred at 40° C. overnight. The reaction mixture was poured into ice water (10 mL) and sat. NaHCO$_3$ (30 mL) solution and extracted with ethyl acetate (2×80 mL). The organic layers were washed with water (30 mL) and brine (30 mL). The combined organic extracts were dried over Na$_2$SO$_4$, filtered off and concentrated in vacuo to afford the desired crude product (461 mg, 88%) as light yellow solid, which was used as if in the next step. LCMS: m/z 233.1 [M+H]+, ESI pos.

Step B: [(3R,5S)-5-Fluoro-1-methyl-3-piperidyl] amine

To a solution of aforementioned N-[(3R,5S)-5-fluoro-1-methyl-3-piperidyl]carbamic acid tert-butyl ester (Example 13, step A) (461 mg, 1.89 mmol, 1 eq) in dichloromethane (10 mL) and methanol (5 mL) was added 4 M HCl in dioxane (3.77 mL, 15.1 mmol, 8 eq) dropwise. The light yellow reaction solution was stirred at 23° C. for 16 h. The reaction mixture was then concentrated in vacuo and dried at high vacuum at 50° C. for 1 h to afford the desired title compound as (369 mg, 1:1 hydrogen chloride) as a light yellow solid which was directly used in the next step. LCMS: m/z 133.1 [M+H]$^+$, ESI pos.

Step C: 6-Chloro-N-[(3R,5S)-5-Fluoro-1-methyl-3-piperidyl]-5-methyl-1,2,4-triazin-3-amine To a mixture of aforementioned [(3R,5S)-5-fluoro-1-methyl-3-piperidyl]amine; hydrochloride (Example 13, step B) (359.9 mg, 2.13 mmol, 1.4 eq) in 1,4-dioxane, extra dry (10 mL) and N,N-dimethylformamide (2 mL) was added at ambient temperature N,N-diisopropylethylamine (1.33 mL, 7.62 mmol, 5.0 eq) resulting in a light yellow solution. After stirring for 10 min at 23° C., commercially available 3,6-dichloro-5-methyl-1,2,4-triazine (CAS #132434-82-3, 250 mg, 1.52 mmol, 1.0 eq) was added and the reaction mixture was stirred at 23° C. for 60 hours. After reaction completion, the main amount of solvents was evaporated, and then the reaction mixture was quenched with a half sat. NaHCO$_3$ solution (80 mL) and extracted with ethylacetate (2×80 mL). The organic layers were washed with water (60 mL) and brine (60 mL). The combined organic extracts were dried over Na$_2$SO$_4$, filtered and concentrated on vacuo. The crude material was adsorbed on ISOLUTE HM-N and purified by flash chromatography (silica gel, 12 g, 0-50% ethyl acetate in heptane; then ethyl acetate: methanol 9:1) to afford the title compound (271 mg, 65%) as light yellow solid. LCMS: m/z 260.2 [M+H]$^+$, ESI pos.

Step D: 2-[3-[[(3R,5S)-5-Fluoro-1-methyl-3-piperidyl]amino]-5-methyl-1,2,4-triazin-6-yl]-5-(trifluoromethyl) phenol A mixture of aforementioned 6-chloro-N-[(3R,5S)-5-fluoro-1-methyl-3-piperidyl]-5-methyl-1,2,4-triazin-3-amine (Example 13, step C) (72 mg, 0.277 mmol, 1.0 eq), [2-hydroxy-4-(trifluoromethyl)phenyl]boronic acid (91.3 mg, 0.444 mmol, 1.6 eq), potassium carbonate (1.25 mmol, 4.5 eq) in 1,4-dioxane (1.9 mL) and water (0.9 mL) was flushed with argon for 2 mins, followed by 1,1'-bis(diphenylphosphino) ferrocene-palladium (ii) dichloride dichloromethane complex (27.2 mg, 0.033 mmol, 0.120 eq). The resulting mixture was stirred at 90° C. for 16 hours. After complete conversion, the reaction mixture was cooled to room temperature and extracted with ethyl acetate (2×20 mL) and half-saturated NH$_4$Cl-solution (20 mL). The organic layers were washed with water (30 mL) and brine (30 mL). The combined organic layers were dried over Na$_2$SO$_4$, filtered and concentrated in vacuo. The crude material was adsorbed on ISOLUTE HM-N and purified by flash chromatography (silica gel, 25 g, 0-50% ethyl acetate in heptane; then ethyl acetate: methanol 9:1) followed by crystallization with ethyl acetate/heptane 1:1 to afford the title product (39 mg, 35%) as white solid. LCMS: m/z 386.2 [M+H]$^+$, ESI pos.

Example 14: 2-[5-Methyl-3-(5,6,7,8-tetrahydroimidazo[1,2-a]pyridin-8-ylamino)-1,2,4-triazin-6-yl]-5-(trifluoromethyl) phenol

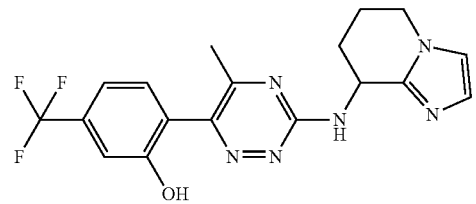 [SMILES: Cc1nc(NC2CCCn3ccnc32)nnc1-c1ccc(C(F)(F)F)cc1O]

Step A: (6-Chloro-5-methyl-1,2,4-triazin-3-yl)-(5,6,7,8-tetrahydroimidazo[1,2-a]pyridin-8-yl)amine To a mixture of commercially available 3,6-dichloro-5-methyl-1,2,4-triazine (CAS #132434-82-3, 71 mg, 0.433 mmol, 1 eq) and commercially available 5,6,7,8-tetrahydroimidazo[1,2-a]pyridin-8-ylamine; dihydrochloride (CAS #2408962-15-0, 136.45 mg, 0.649 mmol, 1.5 eq) in 1,4-dioxane, extra dry (2 mL) was added at room temperature N-ethyldiisopropylamine (233.8 µL, 1.34 mmol, 3.1 eq). The reaction mixture was stirred at 23° C. for 16 hour. Since no product was formed, the reaction mixture was heated at 80° C. for 2 hours. LCMS showed minimal conversion, so that the mixture was transferred in a sealed tube in order to perform a microwave reaction at 100° C. for 1 hour. LCMS showed product but still mainly starting material. Therefore additional N-ethyldiisopropylamine (233.8 μL, 1.34 mmol, 3.1 eq) was added, then the mixture was further microwaved for 90 min at 120° C. and again another 60 min at 120° C. Since more conversion to he product was formed, the reaction was stopped. The reaction mixture was extracted with dichloromethane (30 mL) and water (30 mL). The organic layer was washed with brine (30 mL). The aqueous layers were back-extracted with dichloromethane (2×30 mL). The combined organic layers were dried over Na$_2$SO$_4$, filtered and concentrated in vacuo. The crude product was adsorbed on ISOLUTE HM-N and purified by flash chromatography (silica gel, 12 g, gradient 0% to 10% methanol in dichloromethane) to afford the title compound (23 mg, 20%) as brown solid. LCMS: m/z 265.1 ([{35Cl} M+H]+), 267.1 ([{37Cl} M+H]+), ESI pos.

Step B: 2-[5-Methyl-3-(5,6,7,8-tetrahydroimidazo[1,2-a]pyridin-8-ylamino)-1,2,4-triazin-6-yl]-5-(trifluoromethyl) phenol A mixture of aforementioned (6-chloro-5-methyl-1,2,4-triazin-3-yl)-(5,6,7,8-tetrahydroimidazo[1,2-a]pyridin-8-yl)amine (Example 14, step A) (23 mg, 86.9 μmol, 1.0 eq) and [2-hydroxy-4-(trifluoromethyl)phenyl]boronic acid (30.4 mg, 147.7 μmol, 1.7 eq) and potassium carbonate (48.0 mg, 347.6 μmol, 4.0 eq) was dissolved in 1,4-dioxane (1000 μL) and water (500 μL). The sealable tube was flushed with argon and 1,1'-bis(diphenylphosphino) ferrocene-palladium (ii) dichloride dichloromethane complex (8.51 mg, 10.4 μmol, 0.120 eq) was added. Flushed again with argon and the sealed tube was stirred at 90° C. for 6 hours. The reaction mixture was cooled to room temperature and quenched with water (10 mL) and sat. NH$_4$Cl sol (10 mL), then extracted with dichlormethane (2×40 mL). Organic layers were washed with brine (20 mL), dried over Na$_2$SO$_4$, filtered off and concentrated in vacuo. The crude material was purified by prep RP HPLC (column: YMC-Triart C18, 12 nm, 5 μm, 100×30 mm, eluent: acetonitrile/water+0.1 HCOOH) followed by lyophilisated overnight to afford the desired title compound (3.5 mg, 10%) as white amorph freeze-dried solid. LCMS: m/z 391.3 [M+H]$^+$, ESI pos.

Example 15:5-Fluoro-2-[5-methyl-3-[[(3R)-1-methyl-3-piperidyl]amino]-1,2,4-triazin-6-yl]phenol

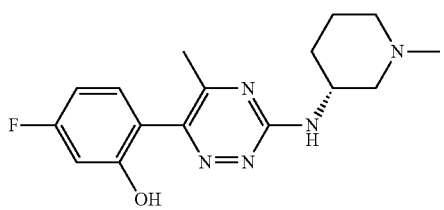

Step A: 6-Chloro-5-methyl-N-[(3R)-1-methyl-3-piperidyl]-1,2,4-triazin-3-amine

To a mixture of 3,6-dichloro-5-methyl-1,2,4-triazine (CAS #132434-82-3, 400 mg, 2.44 mmol, 1.0 eq) and (3R)-1-methylpiperidin-3-amine (CAS #1001353-92-9, 418 mg, 3.66 mmol, 1.5 eq) in 1,4-dioxane (8.0 mL) was added N,N-diisopropylethylamine (326 mg, 0.440 mL, 2.52 mmol, 1.03 eq). The reaction mixture was stirred at room temperature for 16 hours. The reaction mixture extracted with dichloromethane and water. The organic layer was washed with brine. The aqueous layers were backextracted twice with dichloromethane. The combined organic layers were dried over sodium sulfate, filtered and concentrated in vacuo. The crude product was adsorbed on ISOLUTE HM-N and purified by flash chromatography (silica gel, 25 g, gradient 0% to 5% methanol in dichloromethane) to afford the title compound (290 mg, 47% yield) as a brown solid. LCMS: m/z 242.2 [M+H]$^+$, ESI pos.

Step B: 5-Fluoro-2-[5-methyl-3-[[(3R)-1-methyl-3-piperidyl]amino]-1,2,4-triazin-6-yl]phenol A mixture of 6-chloro-5-methyl-N-[(3R)-1-methyl-3-piperidyl]-1,2,4-triazin-3-amine (Example 15, step A) (80 mg, 0.31 mmol, 1.0 eq), (4-fluoro-2-hydroxy-phenyl) boronic acid (CAS #850568-00-2, 77 mg, 0.49 mmol, 1.57 eq), cesium carbonate (326 mg, 1.00 mmol, 3.18 eq) and XPhos Pd G3 (30 mg, 0.04 mmol, 0.11 eq) in 1,4-dioxane (1.2 mL) and water (0.300 mL) was flushed with argon and stirred at 90° C. for 16 hours. The reaction mixture was cooled to room temperature and extracted with ethyl acetate and half-saturated aq. NH$_4$Cl-solution. The aqueous layer was backextracted with ethyl acetate. The organic layers were washed with water and brine. The combined organic layers were dried over sodium sulfate, filtered and concentrated in vacuo. The crude product was adsorbed on ISOLUTE HM-N and purified by flash chromatography (silica gel, 12 g, gradient 0% to 20% methanol in dichloromethane). All fractions containing product were combined and concentrated in vacuo. The residue was adsorbed on ISOLUTE HM-N and repurified by flash chromatography (silica gel, 12 g, gradient 0% to 50% (dichloromethane:methanol:NH$_4$OH 9:1:0.05) in dichloromethane) to afford the title compound (42 mg, 40% yield) as a yellow solid. LCMS: m/z 318.3 [M+H]$^+$, ESI pos.

Example 16:5-Chloro-2-[5-methyl-3-[[(3R)-1-methyl-3-piperidyl]amino]-1,2,4-triazin-6-yl]phenol

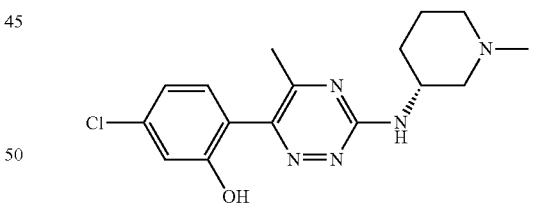

A mixture of 6-chloro-5-methyl-N-[(3R)-1-methyl-3-piperidyl]-1,2,4-triazin-3-amine (Example 15, step A) (95 mg, 0.37 mmol, 1.0 eq), (4-chloro-2-hydroxy-phenyl) boronic acid (CAS #1238196-66-1, 109 mg, 0.63 mmol, 1.69 eq), potassium carbonate (248 mg, 1.79 mmol, 4.81 eq) and 1,1'-bis(diphenylphosphino) ferrocene-palladium (ii) dichloride dichloromethane complex (35 mg, 0.04 mmol, 0.11 eq) in 1,4-dioxane (2.2 mL) and water (1.1 mL) was flushed with argon and stirred at 90° C. for 5 hours and at room temperature for 16 hours. The reaction mixture was extracted with ethyl acetate and half-saturated aq. NH$_4$Cl-solution. The aqueous layer was backextracted twice with ethyl acetate. The organic layers were washed with water and brine. The combined organic layers were dried over sodium sulfate, filtered and concentrated in vacuo. The crude product was adsorbed on ISOLUTE HM-N and purified by flash chromatography (silica gel, 12 g, gradient 0% to 10% methanol in dichloromethane). The residue was adsorbed on ISOLUTE HM-N and repurified by flash chromatography (Si-amine, 12 g, gradient 0% to 10% methanol in ethyl acetate) to afford the title compound (71 mg, 54% yield) as a light brown solid. LCMS: m/z 334.3 [M+H]$^+$, ESI pos.

Example 17: 2-[5-Methyl-3-[[(3R)-3-piperidyl]amino]-1,2,4-triazin-6-yl]-5-(trifluoromethyl) phenol

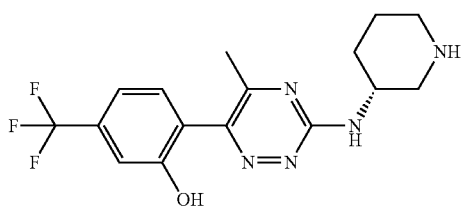

Step A: tert-Butyl (3R)-3-[(6-chloro-5-methyl-1,2,4-triazin-3-yl)amino]piperidine-1-carboxylate To a mixture of 3,6-dichloro-5-methyl-1,2,4-triazine (CAS #132434-82-3, 180 mg, 1.10 mmol, 1.0 eq) and commercially available tert-butyl (3R)-3-aminopiperidine-1-carboxylate (CAS #188111-79-7, 330 mg, 1.65 mmol, 1.5 eq) in 1,4-dioxane (3.6 mL) was added N,N-diisopropylethylamine (148 mg, 0.200 mL, 1.15 mmol, 1.04 eq). The reaction mixture was stirred at room temperature for 16 hours. The reaction mixture extracted with dichloromethane and water. The organic layer was washed with brine. The aqueous layers were back-extracted twice with dichloromethane. The combined organic layers were dried over sodium sulfate, filtered and concentrated in vacuo. The crude product was adsorbed on ISOLUTE HM-N and purified by flash chromatography (silica gel, 12 g, gradient 0% to 40% ethyl acetate in heptane). All fractions containing product were combined and concentrated in vacuo to afford the title compound (351 mg, 93% yield) as a yellow oil. LCMS: m/z 328.3 [M+H]$^+$, ESI pos.

Step B: tert-Butyl (3R)-3-[[6-[2-hydroxy-4-(trifluoromethyl)phenyl]-5-methyl-1,2,4-triazin-3-yl]amino]piperidine-1-carboxylate A mixture of tert-butyl (3R)-3-[(6-chloro-5-methyl-1,2,4-triazin-3-yl)amino]piperidine-1-carboxylate (Example 17, step A) (100 mg, 0.29 mmol, 1.0 eq), [2-hydroxy-4-(trifluoromethyl)phenyl]boronic acid (CAS #1072951-50-8, 115 mg, 0.56 mmol, 1.93 eq), potassium carbonate (220 mg, 1.59 mmol, 5.49 eq) and 1,1'-bis(diphenylphosphino) ferrocene-palladium (ii) dichloride dichloromethane complex (30 mg, 0.04 mmol, 0.13 eq) in 1,4-dioxane (2.0 mL) and water (1.0 mL) was flushed with argon and stirred at 90° C. for 16 hours. The reaction mixture was cooled to room temperature and extracted with ethyl acetate and half-saturated aq. NH$_4$Cl-solution. The aqueous layer was back-extracted with ethyl acetate. The organic layers were washed once with water and once with brine. The combined organic layers were dried over sodium sulfate, filtered and concentrated in vacuo. The crude product was adsorbed on ISOLUTE HM-N and purified by flash chromatography (silica gel, 12 g, gradient 0% to 40% ethyl acetate in heptane). All fractions containing product were combined and concentrated to afford the title compound (105 mg, 76% yield) as a yellow foam. LCMS: m/z 454.4 [M+H]$^+$, ESI pos.

Step C: 2-[5-Methyl-3-[[(3R)-3-piperidyl]amino]-1,2,4-triazin-6-yl]-5-(trifluoromethyl) phenol To a solution of tert-butyl (3R)-3-[[6-[2-hydroxy-4-(trifluoromethyl)phenyl]-5-methyl-1,2,4-triazin-3-yl]amino]piperidine-1-carboxylate (Example 17, step B) (100 mg, 0.21 mmol, 1.0 eq) in dichloromethane (0.55 mL) and methanol (0.27 mL) was added dropwise 4 M HCl in dioxane (528 mg, 0.440 mL, 1.76 mmol, 8.4 eq). The reaction mixture was stirred at room temperature for 2 hours. The reaction mixture was concentrated in vacuo. The residue was extracted with a mixture of dichloromethane/methanol (19:1) and saturated aq. NaHCO3-solution. The aqueous layer was backextracted twice with a mixture of dichloromethane/methanol (19:1) and three times with a mixture of dichloromethane/methanol (9:1). The combined organic layers were dried over sodium sulfate, filtered and concentrated in vacuo to afford the title compound (70 mg, 85% yield) as a yellow foam. LCMS: m/z 354.3 [M+H]$^+$, ESI pos.

Example 18: 2-[5-Methyl-3-[[(3R)-1-methyl-3-piperidyl]amino]-1,2,4-triazin-6-yl]-5-(trifluoromethyl) phenol

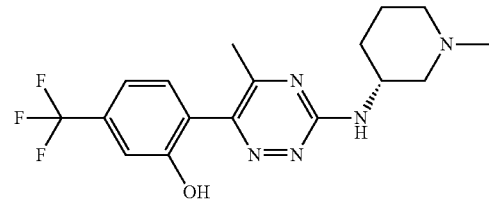 [SMILES: Cc1nc(N[C@@H]2CCCN(C)C2)nnc1-c1ccc(C(F)(F)F)cc1O]

A mixture of 6-chloro-5-methyl-N-[(3R)-1-methyl-3-piperidyl]-1,2,4-triazin-3-amine (Example 15, step A) (90 mg, 0.35 mmol, 1.0 eq), [2-hydroxy-4-(trifluoromethyl)phenyl]boronic acid (CAS #1072951-50-8, 124 mg, 0.60 mmol, 1.7 eq), potassium carbonate (235 mg, 1.7 mmol, 4.81 eq) and 1,1'-bis(diphenylphosphino) ferrocene-palladium (ii) dichloride dichloromethane complex (34 mg, 0.04 mmol, 0.12 eq) in 1,4-dioxane (2.0 mL) and water (1.0 mL) was flushed with argon and stirred at 90° C. for 16 h. The reaction mixture was extracted with ethyl acetate and half-saturated aq. NH$_4$Cl-solution. The aqueous layer was backextracted twice with ethyl acetate. The organic layers were washed with water and brine. The combined organic layers were dried over sodium sulfate, filtered and concentrated in vacuo. The crude product was adsorbed on ISO-LUTE HM-N and purified by flash chromatography (silica gel, 12 g, gradient 0% to 10% methanol in dichloromethane). All fractions containing product were combined and concentrated in vacuo. The residue was triturated with ethyl acetate/heptane (~1:1) to afford the title compound (24 mg, 18% yield) as an off-white powder. LCMS: m/z 368.3 [M+H]$^+$, ESI pos.

Example 19: 2-[3-[[(1R,2R)-2-Hydroxycyclohexyl]amino]-5-methyl-1,2,4-triazin-6-yl]-5-(trifluoromethyl) phenol

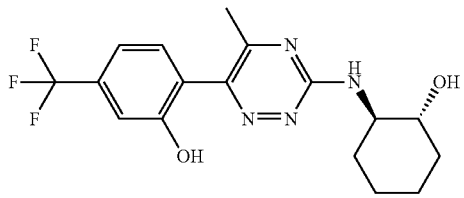

Step A: (1R,2R)-2-[(6-Chloro-5-methyl-1,2,4-triazin-3-yl)amino]cyclohexanol

To a mixture of 3,6-dichloro-5-methyl-1,2,4-triazine (CAS #132434-82-3, 200 mg, 1.22 mmol, 1.0 eq) and commercially available (1R,2R)-2-aminocyclohexanol hydrochloride (CAS #13374-31-7, 277 mg, 1.83 mmol, 1.5 eq) in 1,4-dioxane (4.0 mL) was added N,N-diisopropylethylamine (636 mg, 0.860 mL, 4.92 mmol, 4.04 eq). The reaction mixture was stirred at room temperature for five days. The reaction mixture extracted with dichloromethane and water. The organic layer was washed with brine. The aqueous layers were backextracted twice with dichloromethane. The combined organic layers were dried over sodium sulfate, filtered and concentrated in vacuo. The crude product was adsorbed on ISOLUTE HM-N and purified by flash chromatography (silica gel, 25 g, gradient 0% to 5% methanol in dichloromethane) to afford the title compound (178 mg, 57% yield) as light brown solid. LCMS: m/z 243.1 [M+H]$^+$, ESI pos.

Step B: 2-[3-[[(1R,2R)-2-Hydroxycyclohexyl]amino]-5-methyl-1,2,4-triazin-6-yl]-5-(trifluoromethyl) phenol A mixture of (1R,2R)-2-[(6-chloro-5-methyl-1,2,4-triazin-3-yl)amino]cyclohexanol (Example 19, step A) (96 mg, 0.38 mmol, 1.0 eq), [2-hydroxy-4-(trifluoromethyl)phenyl]boronic acid (CAS #1072951-50-8, 132 mg, 0.64 mmol, 1.71 eq), potassium carbonate (250 mg, 1.81 mmol, 4.81 eq) and 1,1'-bis(diphenylphosphino) ferrocene-palladium (ii) dichloride dichloromethane complex (36 mg, 0.04 mmol, 0.12 eq) in 1,4-dioxane (2.2 mL) and water (1.1 mL) was flushed with argon and stirred at 85° C. for 16 hours. The reaction mixture was cooled to room temperature and extracted with ethyl acetate and half-saturated aq. NH$_4$Cl-solution. The aqueous layer was back-extracted with ethyl acetate. The organic layers were washed with water and brine. The combined organic layers were dried over sodium sulfate, filtered and concentrated in vacuo. The crude product was adsorbed on ISOLUTE HM-N and purified by flash chromatography (silica gel, 12 g, gradient 0% to 5% methanol in dichloromethane). All fractions containing product were combined and concentrated in vacuo. The residue was triturated with ethyl acetate to afford the title compound (87 mg, 60% yield) as an off-white powder. LCMS: m/z 369.2 [M+H]$^+$, ESI pos.

Example 21: 2-[3-[[(3R)-1-Ethyl-3-piperidyl]amino]-5-methyl-1,2,4-triazin-6-yl]-3-methyl-5-(trifluoromethyl) phenol

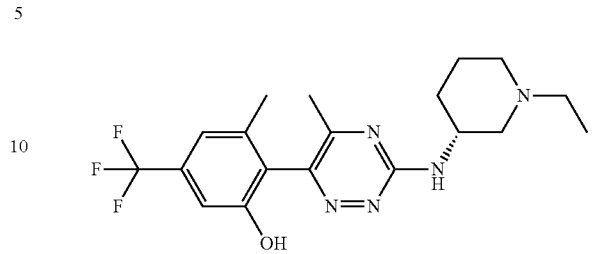

A mixture of 6-chloro-N-[(3R)-1-ethyl-3-piperidyl]-5-methyl-1,2,4-triazin-3-amine (Example 4, step A) (60 mg, 0.22 mmol, 1.0 eq), 3-methyl-2-(4,4,5,5-tetramethyl-1,3,2-dioxaborolan-2-yl)-5-(trifluoromethyl) phenol (CAS #2557358-38-8, 100 mg, 0.33 mmol, 1.49 eq), cesium carbonate (220 mg, 0.68 mmol, 3.03 eq) and XPhos Pd G3 (20 mg, 0.02 mmol, 0.11 eq) in 1,4-dioxane (0.80 mL) and water (0.20 mL) was flushed with argon and stirred at 100° C. for 2 hours. The reaction mixture was cooled to room temperature and extracted with ethyl acetate and half-saturated aq. NH$_4$Cl-solution. The aqueous layer was back-extracted with ethyl acetate. The organic layers were washed with water and brine. The combined organic layers were dried over sodium sulfate, filtered and concentrated in vacuo. The crude product was adsorbed on ISOLUTE HM-N and purified by flash chromatography (silica gel, 12 g, gradient 0% to 100% (dichloromethane:methanol:NH$_4$OH 9:1:0.05) in dichloromethane) to afford the title compound (67 mg, 72% yield) as a brown foam. LCMS: m/z 396.3 [M+H]$^+$, ESI pos.

Example 22: 2-[3-[[(3R)-1-Ethyl-3-piperidyl]amino]-5-methyl-1,2,4-triazin-6-yl]-5-(trifluoromethoxy) phenol

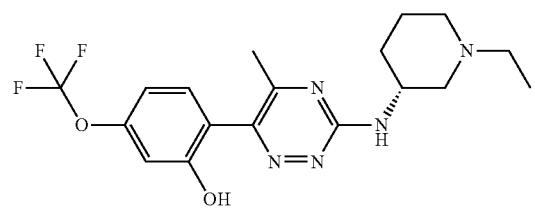 [SMILES: CCN1CCC[C@@H](Nc2nnc(-c3ccc(OC(F)(F)F)cc3O)c(C)n2)C1]

A mixture of 6-chloro-N-[(3R)-1-ethyl-3-piperidyl]-5-methyl-1,2,4-triazin-3-amine (Example 4, step A) (70 mg, 0.26 mmol, 1.0 eq), [2-hydroxy-4-(trifluoromethoxy)phenyl]boronic acid (CAS #1309768-22-6, 90 mg, 0.41 mmol, 1.56 eq), cesium carbonate (257 mg, 0.79 mmol, 3.03 eq) and XPhos Pd G3 (24 mg, 0.03 mmol, 0.11 eq) in 1,4-dioxane (1.2 mL) and water (0.30 mL) was flushed with argon and stirred at 100° C. for 3 hours. The reaction mixture was cooled to room temperature and extracted with ethyl acetate and water. The aqueous layer was backextracted with ethyl acetate. The organic layers were washed with water and brine. The combined organic layers were dried over sodium sulfate, filtered and concentrated in vacuo. The crude product was adsorbed on ISOLUTE HM-N and purified by flash chromatography (silica gel, 12 g, gradient 0% to 10% methanol in dichloromethane). All fractions containing product were combined and concentrated in vacuo. The residue was adsorbed on ISOLUTE HM-N and repurified by flash chromatography (silica gel, 12 g, gradient 0% to 100% (dichloromethane:methanol:NH₄OH 9:1:0.05) in dichloromethane). All fractions containing product were combined and concentrated in vacuo. The residue was triturated with ethyl acetate/heptane to afford the title compound (28 mg, 26% yield) as a light yellow powder. LCMS: m/z 398.3 [M+H]⁺, ESI pos.

Example 23: (3S,5R)-1-Ethyl-5-[[6-[2-hydroxy-4-(trifluoromethyl)phenyl]-5-methyl-1,2,4-triazin-3-yl]amino]piperidin-3-ol

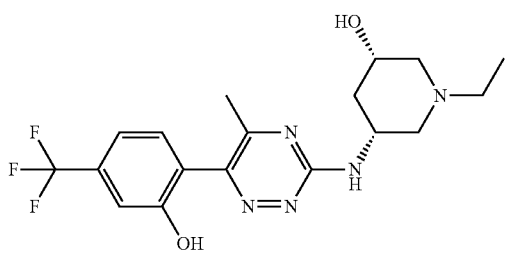

Step A: tert-Butyl (3R,5S)-3-[(6-chloro-5-methyl-1,2,4-triazin-3-yl)amino]-5-hydroxy-piperidine-1-carboxylate To a mixture of 3,6-dichloro-5-methyl-1,2,4-triazine (CAS #132434-82-3, 250 mg, 1.52 mmol, 1.0 eq) and tert-butyl (3R,5S)-3-amino-5-hydroxy-piperidine-1-carboxylate (CAS #1932513-59-1, 396 mg, 1.83 mmol, 1.2 eq) in 1,4-dioxane (5.0 mL) was added N,N-diisopropylethylamine (204 mg, 0.275 mL, 1.57 mmol, 1.03 eq). The reaction mixture was stirred at room temperature for 16 hours. To the reaction mixture was added N,N-dimethylformamide (0.50 mL). Let stir at room temperature for 16 hours. The reaction mixture extracted with dichloromethane and water. The organic layer was washed with brine. The aqueous layers were back-extracted twice with dichloromethane. The combined organic layers were dried over sodium sulfate, filtered and concentrated in vacuo. The crude product was adsorbed on ISOLUTE HM-N and purified by flash chromatography (silica gel, 24 g, gradient 0% to 100% ethyl acetate in heptane) to afford the title compound (443 mg, 80% yield) as a yellow oil. LCMS: m/z 344.2 [M+H]⁺, ESI pos.

Step B: (3S,5R)-5-[(6-Chloro-5-methyl-1,2,4-triazin-3-yl)amino]piperidin-3-ol hydrochloride To a solution of tert-butyl (3R,5S)-3-[(6-chloro-5-methyl-1,2,4-triazin-3-yl)amino]-5-hydroxy-piperidine-1-carboxylate (Example 23, step A) (338 mg, 0.93 mmol, 1.0 eq) in dichloromethane (3.6 mL) and methanol (1.8 mL) was added dropwise 4 M HCl in dioxane (3.0 mL, 12 mmol, 12.85 eq). Let stir at room temperature for 16 hours. The reaction mixture was concentrated in vacuo to afford the title compound (388 mg, 96% yield, 65% purity) as a yellow foam, which was used without further purification. LCMS: m/z 244.1 [M+H]⁺, ESI pos.

Step C: (3S,5R)-5-[(6-Chloro-5-methyl-1,2,4-triazin-3-yl)amino]-1-ethyl-piperidin-3-ol To a suspension of (3S,5R)-5-[(6-chloro-5-methyl-1,2,4-triazin-3-yl)amino]piperidin-3-ol hydrochloride (Example 23, step B) (385 mg, 0.89 mmol, 1.0 eq, 65% purity) in dichloromethane (3.9 mL) was added sodium acetate (149 mg, 1.82 mmol, 2.03 eq) followed by acetaldehyde (101 mg, 0.130 mL, 2.3 mmol, 2.58 eq) under ice-bath cooling. Sodium triacetoxyborohydride (285 mg, 1.34 mmol, 1.51 eq) was added at 0° C. and the reaction mixture was stirred at 0° C. for 15 minutes and at room temperature for 4 hours. The reaction mixture was carefully basified with saturated aq. NaHCO₃-solution and then extracted three times with dichloromethane. The combined organic layers were dried over sodium sulfate, filtered and concentrated in vacuo. The crude product was adsorbed on ISOLUTE HM-N and purified by flash chromatography (silica gel, 12 g, 0% to 10% methanol in dichloromethane) to afford the title compound (85 mg, 33% yield) as an orange foam. LCMS: m/z 272.1 [M+H]⁺, ESI pos.

Step D: (3S,5R)-1-Ethyl-5-[[6-[2-hydroxy-4-(trifluoromethyl)phenyl]-5-methyl-1,2,4-triazin-3-yl]amino]piperidin-3-ol To a solution of (3S,5R)-5-[(6-chloro-5-methyl-1,2,4-triazin-3-yl)amino]-1-ethyl-piperidin-3-ol (Example 23, step C) (85 mg, 0.30 mmol, 1.0 eq), [2-hydroxy-4-(trifluoromethyl)phenyl]boronic acid (CAS #1072951-50-8, 105 mg, 0.51 mmol, 1.72 eq) and potassium carbonate (198 mg, 1.43 mmol, 4.82 eq) in 1,4-dioxane (1.32 mL) and water (0.33 mL) was added 1,1'-bis(diphenylphosphino) ferrocene-palladium (ii) dichloride dichloromethane complex (28 mg, 0.03 mmol, 0.12 eq). Let stir under argon at 90° C. for 16 hours. The reaction mixture was cooled to room temperature and then extracted with ethyl acetate and half-saturated aq. NH₄Cl-solution. The aqueous layer was backextracted twice with ethyl acetate. The organic layers were washed with water and brine. The combined organic layers were dried over sodium sulfate, filtered and concentrated in vacuo. The crude product was adsorbed on ISOLUTE-HM-N and purified by flash chromatography (silica gel, 12 g, gradient 0% to 100% (dichloromethane:methanol:NH₄OH 9:1:0.05) in dichloromethane). All fractions containing product were combined and concentrated in vacuo. The residue was triturated with ethyl acetate/heptane to afford the title compound (51 mg, 41% yield) as a light brown powder. LCMS: m/z 398.3 [M+H]⁺, ESI pos.

Example 24: (3S,5R)-1-Ethyl-5-[[6-[2-hydroxy-6-methyl-4-(trifluoromethyl)phenyl]-5-methyl-1,2,4-triazin-3-yl]amino]piperidin-3-ol

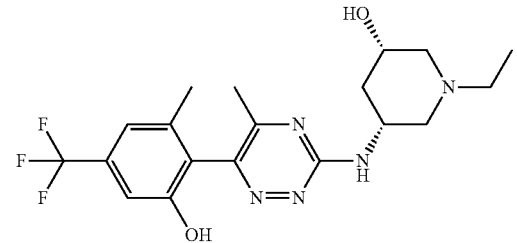 [SMILES: CCN1C[C@@H](O)C[C@@H](Nc2nnc(-c3c(C)cc(C(F)(F)F)cc3O)c(C)n2)C1]

A mixture of (3S,5R)-5-[(6-chloro-5-methyl-1,2,4-triazin-3-yl)amino]-1-ethyl-piperidin-3-ol (Example 23, step C) (55 mg, 0.18 mmol, 1.0 eq), [2-hydroxy-6-methyl-4-(trifluoromethyl)phenyl]boronic acid (CAS #2557358-06-0, 60 mg, 0.26 mmol, 1.42 eq), cesium carbonate (179 mg, 0.55 mmol, 3.02 eq) and XPhos Pd G3 (18 mg, 0.021 mmol, 0.12 eq) in 1,4-dioxane (0.80 mL) and water (0.20 mL) was flushed with argon and stirred at 100° C. for 2.75 hours. To the reaction mixture was added at room temperature [2-hydroxy-6-methyl-4-(trifluoromethyl)phenyl]boronic acid (CAS #2557358-06-0, 21 mg, 0.09 mmol, 0.50 eq) and XPhos Pd G3 (6 mg, 0.01 mmol, 0.04 eq). The mixture was flushed with argon and stirred at 100° C. for 1.25 hours. The reaction mixture was cooled to room temperature and extracted with ethyl acetate and water. The aqueous layer was backextracted with ethyl acetate. The organic layers were washed with water and brine. The combined organic layers were dried over sodium sulfate, filtered and concentrated in vacuo. The crude product was adsorbed on ISOLUTE HM-N and purified by flash chromatography (silica gel, 12 g, gradient 0% to 100% (dichloromethane:methanol: NH$_4$OH 9:1:0.05) in dichloromethane) to afford the title compound (49 mg, 59% yield, 90% purity) as an orange solid. LCMS: m/z 412.3 [M+H]$^+$, ESI pos.

Example 25: 5-[3-[[(3R)-1-Ethyl-3-piperidyl]amino]-5-methyl-1,2,4-triazin-6-yl]indan-4-ol

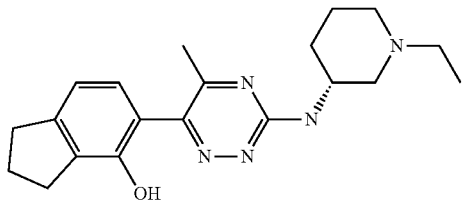

Step A: 2-(4-Benzyloxyindan-5-yl)-4,4,5,5-tetramethyl-1,3,2-dioxaborolane

To a solution of 4-benzyloxy-5-bromo-indane (CAS #2676863-60-6, 538 mg, 1.51 mmol, 1.00 eq, 85% purity) and 2-isopropoxy-4,4,5,5-tetramethyl-1,3,2-dioxaborolane (465 mg, 0.510 mL, 2.5 mmol, 1.66 eq) in tetrahydrofuran (6.5 mL) was added dropwise n-butyllithium, 1.6 M solution in hexanes (1.9 mL, 3.04 mmol, 2.02 eq) at −76° C. (keeping the internal temperature below −68° C.). Let stir at −76° C. for 3 h. The reaction mixture was warmed to −60° C., quenched with saturated aq. NH$_4$Cl-solution at −60° C., warmed to room temperature and then extracted with ethyl acetate and saturated aq. NH$_4$Cl-solution. The aqueous layer was back extracted with ethyl acetate. The organic layers were washed with brine. The combined organic layers were dried over sodium sulfate, filtered and concentrated in vacuo. The crude product was adsorbed on ISOLUTE HM-N and purified by flash chromatography (silica gel, 25 g, gradient 0% to 10% ethyl acetate in heptane) to afford the title compound (391 mg, 70% yield) as a colorless oil. LCMS: m/z 351.2 [M+H]$^+$, ESI pos.

Step B: 5-(4,4,5,5-Tetramethyl-1,3,2-dioxaborolan-2-yl)indan-4-ol

A solution of aforementioned 2-(4-benzyloxyindan-5-yl)-4,4,5,5-tetramethyl-1,3,2-dioxaborolane (Example 25, step A) (388 mg, 1.05 mmol, 1.00 eq) in ethyl acetate (4.8 mL) was three times alternating evacuated and flushed with argon. Palladium on activated charcoal, 10% Pd basis (39 mg, 0.037 mmol, 0.04 eq) was added carefully. The reaction flask was evacuated, flushed with argon, evacuated and flushed with hydrogen. The reaction mixture was stirred under hydrogen atmosphere (balloon) at room temperature for 16 hours. The reaction mixture was filtered and rinsed well with ethyl acetate/methanol. The filtrate was concentrated in vacuo to afford the title compound (286 mg, quantitative yield) as an off-white solid. LCMS: m/z 261.2 [M+H]$^+$, ESI pos.

Step C: 5-[3-[[(3R)-1-Ethyl-3-piperidyl]amino]-5-methyl-1,2,4-triazin-6-yl]indan-4-ol A mixture of 6-chloro-N-[(3R)-1-ethyl-3-piperidyl]-5-methyl-1,2,4-triazin-3-amine (Example 4, step A) (80 mg, 0.29 mmol, 1.00 eq), 5-(4,4,5,5-tetramethyl-1,3,2-dioxaborolan-2-yl) indan-4-ol (Example 25, step B) (129 mg, 0.47 mmol, 1.60 eq), potassium carbonate (187 mg, 1.35 mmol, 4.60 eq) and 1,1'-bis(diphenylphosphino) ferrocene-palladium (ii) dichloride dichloromethane complex (36 mg, 0.044 mmol, 0.15 eq) in 1,4-dioxane (1.8 mL) and water (0.90 mL) was flushed with argon and stirred at 100° C. for 2.5 hours. The reaction mixture was cooled to room temperature and then extracted with ethyl acetate and water. The aqueous layer was backextracted with ethyl acetate. The organic layers were washed with water and brine. The combined organic layers were dried over sodium sulfate, filtered and concentrated in vacuo. The crude product was adsorbed on ISOLUTE HM-N and purified by flash chromatography (silica gel, 12 g, gradient 0% to 10% methanol in dichloromethane). The residue was triturated with ethyl acetate/heptane. The filtrate was concentrated in vacuo to afford the title compound (69 mg, 63% yield) as a brown solid. LCMS: m/z 354.3 [M+H]$^+$, ESI pos.

Examples 26 and 27: 2-[5-Methyl-3-[[rac-(8S,8aR)-1,2,3,5,6,7,8,8a-octahydroindolizin-8-yl]amino]-1,2,4-triazin-6-yl]-5-(trifluoromethyl) phenol and 2-[5-methyl-3-[[rac-(8S,8aS)-1,2,3,5,6,7,8,8a-octahydroindolizin-8-yl]amino]-1,2,4-triazin-6-yl]-5-(trifluoromethyl) phenol

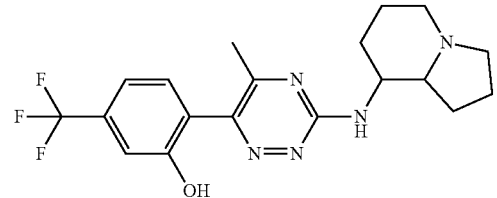 [SMILES: Cc1nc(NC2CCCN3CCCC23)nnc1-c1ccc(C(F)(F)F)cc1O]

Step A: (6-Chloro-5-methyl-1,2,4-triazin-3-yl)-indolizidin-8-yl-amine

To a solution of commercially available 3,6-dichloro-5-methyl-1,2,4-triazine (CAS #132434-82-3, 277 mg, 1.69 mmol, 1.0 eq) and commercially available indolizidin-8-ylamine (374 mg, 2.53 mmol, 1.5 eq) in 1,4-dioxane, extra dry (6 mL) was added at room temperature N-ethyldiisopropylamine (303 μL, 1.74 mmol, 1.03 eq) resulting in a brown clear solution. The reaction mixture was stirred at 23° C. for 16 h. After reaction completion, the reaction mixture was extracted with dichloromethane (30 mL) and water (30 mL). The organic layer was washed with brine (30 mL). The aqueous layers were back-extracted with dichloromethane (2×30 mL). The combined organic layers were dried over Na₂SO₄, filtered and concentrated in vacuo. The crude product was adsorbed on ISOLUTE HM-N and purified by flash chromatography (silica gel, 25 g, gradient 0% to 10% methanol in dichloromethane) to afford the title compounds in two fractions: the first one (255 mg, 55%) as a light brown gum and the second one (37 mg, 8%) as a light brown oil. LCMS: m/z 268.2 ([{35Cl} M+H]+), 270.1 ([{37Cl} M+H]+), ESI pos.

Step B: 2-[5-Methyl-3-[[rac-(8S,8aR)-1,2,3,5,6,7,8,8a-octahydroindolizin-8-yl]amino]-1,2,4-triazin-6-yl]-5-(trifluoromethyl) phenol

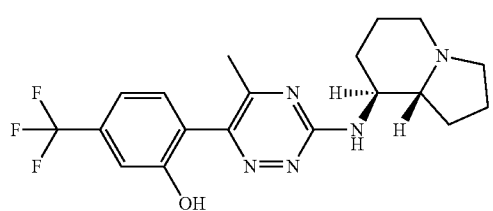

A mixture of aforementioned (Example 26/27, step A, fraction 1) (6-chloro-5-methyl-1,2,4-triazin-3-yl)-indolizidin-8-yl-amine (255 mg, 0.952 mmol, 1.00 eq) and [2-hydroxy-4-(trifluoromethyl)phenyl]boronic acid (333 mg, 1.62 mmol, 1.70 eq) and potassium carbonate (632 mg, 4.57 mmol, 4.80 eq) was dissolved in 1,4-dioxane (6 mL) and water (3 mL). The sealable tube was flushed with argon and 1,1'-bis(diphenylphosphino) ferrocene-palladium (ii) dichloride dichloromethane complex (93 mg, 0.114 mmol, 0.120 eq) was added. Flushed again with argon and the sealed tube was stirred at 90° C. for 3 hours. The reaction mixture was cooled to room temperature and quenched with water (10 mL) and sat. NH₄Cl solution (10 mL), then extracted with dichloromethane (2×40 mL). Organic layers were washed with brine (20 mL), dried over Na₂SO₄, filtered off and concentrated in vacuo. The crude product was adsorbed on ISOLUTE HM-N and purified by flash chromatography (silica gel, 40 g, gradient 0% to 10% methanol in dichloromethane) followed by trituration in tert-Butyl methyl ether (5 mL) to afford the title compound (Example 26) (226 mg, 57% yield) as an off-white solid. LCMS: m/z 394.1 [M+H]⁺, ESI pos.

Step C: 2-[5-Methyl-3-[[rac-(8S,8aS)-1,2,3,5,6,7,8,8a-octahydroindolizin-8-yl]amino]-1,2,4-triazin-6-yl]-5-(trifluoromethyl) phenol

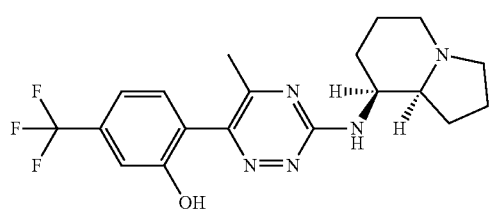

A mixture of aforementioned (Example 26/27, step A, fraction 2,) (6-chloro-5-methyl-1,2,4-triazin-3-yl)-indolizidin-8-yl-amine (37 mg, 138.2 μmol, 1.00 eq) and [2-hydroxy-4-(trifluoromethyl)phenyl]boronic acid (48.4 mg, 235 μmol, 1.70 eq) and potassium carbonate (91.7 mg, 663.3 μmol, 4.80 eq) was dissolved in 1,4-dioxane (871 μL) and water (435 μL). The sealable tube was flushed with argon and 1,1'-bis(diphenylphosphino) ferrocene-palladium (ii) dichloride dichloromethane complex (13.5 mg, 16.6 μmol, 0.120 eq) was added. Flushed again with argon and the sealed tube was stirred at 90° C. for 3 hours. The reaction mixture was cooled to room temperature and quenched with water (10 mL) and sat NH₄Cl sol (10 mL), then extracted with dichloromethane (2×40 mL). Organic layers were washed with brine (20 mL), dried over Na₂SO₄, filtered off and concentrated in vacuo. The crude product was adsorbed on ISOLUTE HM-N and purified by flash chromatography (silica gel, 12 g, gradient 0% to 10% methanol in dichloromethane) followed by prep HPLC to the title compound (Example 27) (22 mg, 38%) as light brown foam. The relative stereo chemistry was attributed but not verified at this point.

Examples 28 and 29:2-[3-[[(8R,8aS)-1,2,3,5,6,7,8,8a-octahydroindolizin-8-yl]amino]-5-methyl-1,2,4-triazin-6-yl]-5-(trifluoromethyl) phenol and 2-[3-[[(8S,8aR)-1,2,3,5,6,7,8,8a-octahydroindolizin-8-yl]amino]-5-methyl-1,2,4-triazin-6-yl]-5-(trifluoromethyl) phenol

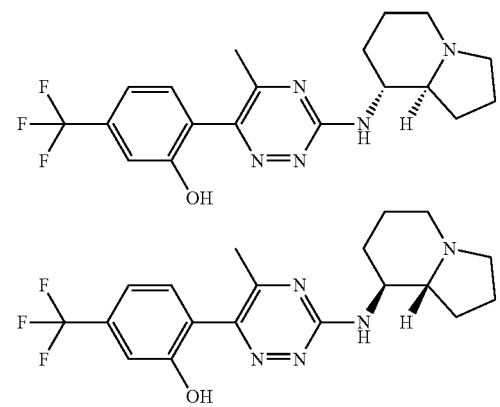

The aforementioned title compound (Example 26) (92 mg, 0.234 mmol, 1.00 eq) was subjected to chiral prep HPLC (SFC, column chiral Lux C4, 5 μm, 250×20 mm; method: 25% iPrOH+DEA; 120 bar BPR, 90 mL/min) to afford two fractions of the enantiopure Example 28 as an off-white solid (41 mg, rt=1.706 min, 100% ee) and the enantiopure Example 29 as an off-white solid (38 mg, rt=2.184 min, 100% ee).

Example 30: 2-[3-[[(3R)-1-Ethyl-3-piperidyl]amino]-5-(trifluoromethyl)-1,2,4-triazin-6-yl]-5-(trifluoromethyl) phenol; 2,2,2-trifluoroacetic acid

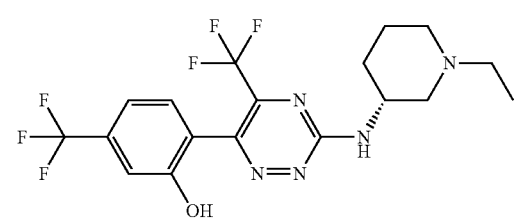

Step A: 5-(Trifluoromethyl)-1,2,4-triazin-3-amine

The solution of NaOAc (9.53 g, 70.0 mmol, 2.1 eq) in water (36 mL) was added commercially available 1,1-dibromo-3,3,3-trifluoroacetone (CAS #431-67-4, 9.0 g, 33.4 mmol, 1.0 eq), then stirred at 100° C. for 30 min, then cooled to 20° C., commercially available [(E)-aminocarbonohydrazonoyl]ammonium; hydron; carbonate (CAS #2582-30-1, 4.54 g, 33.4 mmol, 1.0 eq.) was added in portions at 20° C., and stirred at 20° C. for 3 h. The NaOH (16.7 mL, 66.7 mmol, 2.0 eq, 4 M in water) was added (adjusted the pH to about 10), then stirred at 20° C. for 36 h. The reaction solution was diluted with water (200 mL), extracted with ethyl acetate (100 mL×3). The combined organic phase was washed with brine (200 mL), dried over anhydrous sodium sulfate, filtered and concentrated under reduced pressure. The residue was purified by column (silica gel, petroleum ether:ethyl acetate=1:0 to 3:1) to afford the title compound (500 mg, 9% yield) as a white solid. 1H NMR (400 MHZ, DMSO-$d_6$) δ 9.07 (s, 1H), 8.00 (br.s, 2H).

Step B: 6-Bromo-5-(trifluoromethyl)-1,2,4-triazin-3-amine

To a solution of 5-(trifluoromethyl)-1,2,4-triazin-3-amine (300.0 mg, 1.83 mmol, 1.0 eq.) in DMF (6 mL) was added NBS (388.1 mg, 2.19 mmol, 1.2 eq), then stirred at 20° C. for 2 h. The reaction solution was diluted with water (50 mL), extracted with ethyl acetate (20 mL×3). The combined organic phase was washed with brine (30 mL×3), dried over anhydrous sodium sulfate, filtered and the filtrate was concentrated under reduced pressure. The crude product was purified by column (silica gel, petroleum ether:EtOAc=1:0 to 2:1) to afford the title compound (220 mg, 50% yield) as a yellow solid. 1H NMR (400 MHZ, CDCl$_3$) δ 5.94 (br.s, 2H).

Step C: 2-(3-Amino-5-(trifluoromethyl)-1,2,4-triazin-6-yl)-5-(trifluoromethyl) phenol To a solution of 6-bromo-5-(trifluoromethyl)-1,2,4-triazin-3-amine (170 mg, 0.7 mmol, 1.0 eq) in 1,4-dioxane (2 mL) and water (0.500 mL) was added (2-hydroxy-4-(trifluoromethyl)phenyl) boronic acid (172.9 mg, 0.84 mmol, 1.2 eq.), Na2CO$_3$ (185.4 mg, 1.75 mmol, 2.5 eq), then Pd(dppf)Cl$_2$ (102.4 mg, 0.14 mmol, 0.2 eq.). The reaction mixture was stirred at 100° C. for 2 h under N$_2$ atmosphere. The reaction mixture was cooled to 25° C., and was diluted with water (50 mL), extracted with ethyl acetate (20 mL×3). The combined organic phase was washed with brine (50 mL), dried over anhydrous sodium sulfate, filtered and the filtrate was concentrated under reduced pressure. The residue was purified by column (silica gel, petroleum ether:ethyl acetate=1:0 to 2:1) to afford the title compound (180 mg, 79% yield) as a yellow solid. 1H NMR (400 MHz, DMSO-$d_6$) δ 10.50 (br.s, 1H), 8.08 (br.s, 2H), 7.54 (d, 1H), 7.27 (dd, 1H), 7.18 (s, 1H).

Step D: 2-(3-Chloro-5-(trifluoromethyl)-1,2,4-triazin-6-yl)-5-(trifluoromethyl) phenol To a mixture of 2-(3-amino-5-(trifluoromethyl)-1,2,4-triazin-6-yl)-5-(trifluoromethyl) phenol (90.0 mg, 0.28 mmol, 1.0 eq), CuCl (82.5 mg, 0.83 mmol, 3.0 eq), LiCl (23.5 mg, 0.56 mmol, 2.0 eq), benzyl(triethyl) azanium; chloride (240.3 mg, 1.05 mmol, 3.8 eq) in MeCN (3 mL) was added tert-butyl nitrite (143.1 mg, 1.39 mmol, 5.0 eq) at 25° C., then the mixture was stirred at 70° C. for 1 h under N$_2$. The mixture was filtered and the filtrate was concentrated under reduced pressure. The crude product was purified by prep-TLC (petroleum ether:ethyl acetate=4:1, Rf=0.5) to afford the title compound (20.0 mg, 21% yield) as a yellow oil. LCMS: m/z 436.3 [M+H]$^+$, ESI pos.

Examples 31, 32, 33 and 34: 2-[3-[[(6S or 6R,8aS or 8aR)-1,2,3,5,6,7,8,8a-octahydroindolizin-6-yl]amino]-5-methyl-1,2,4-triazin-6-yl]-5-(trifluoromethyl) phenol; 2-[3-[[(6R or 6S,8aS or 8aR)-1,2,3,5,6,7,8,8a-octahydroindolizin-6-yl]amino]-5-methyl-1,2,4-triazin-6-yl]-5-(trifluoromethyl) phenol; 2-[3-[[(6S or 6R,8aR or 8aS)-1,2,3,5,6,7,8,8a-octahydroindolizin-6-yl]amino]-5-methyl-1,2,4-triazin-6-yl]-5-(trifluoromethyl) phenol and 2-[3-[[(6R or 6S, 8aR or 8aS)-1,2,3,5,6,7,8,8a-octahydroindolizin-6-yl]amino]-5-methyl-1,2,4-triazin-6-yl]-5-(trifluoromethyl) phenol

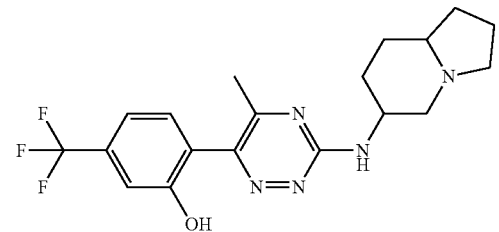 [SMILES: Cc1nc(NC2CCC3CCCN3C2)nnc1-c1ccc(C(F)(F)F)cc1O]

Step A: N-(6-Chloro-5-methyl-1,2,4-triazin-3-yl)-1,2,3,5,6,7,8,8a-octahydroindolizin-6-amine To a mixture of commercially available 3,6-dichloro-5-methyl-1,2,4-triazine (CAS #132434-82-3, 260 mg, 1.51 mmol, 1.00 eq) and commercially available indolizin-6-ylamine (1824202-77-8, 316.8 mg, 2.26 mmol, 1.50 eq) in 1,4-dioxane (4.9 mL) was added N,N-diisopropylethylamine (201 mg, 272 µL, 1.56 mmol, 1.033 eq). The reaction mixture was stirred at room temperature overnight. The reaction mixture was extracted with dichloromethane and water. The organic layer was washed with brine. The aqueous layers were back extracted twice with dichloromethane. The combined organic layers were dried over sodium sulfate, filtered and concentrated in vacuo. The crude product was adsorbed on ISOLUTE HM-N and purified by flash chromatography (silica gel, 24 g, gradient 0% to 10% methanol in dichloromethane) to afford the title compounds in two fractions: the first one (124 mg, 29% yield) as a green solid and the second one (80 mg, 19% yield) as a light green powder. LCMS: m/z 268.3 [M+H]$^+$, ESI pos.

Step B: 2-[3-[[(6S or 6R,8aS or 8aR)-1,2,3,5,6,7,8,8a-octahydroindolizin-6-yl]amino]-5-methyl-1,2,4-triazin-6-yl]-5-(trifluoromethyl) phenol; 2-[3-[[(6R or 6S,8aS or 8aR)-1,2,3,5,6,7,8,8a-octahydroindolizin-6-yl]amino]-5-methyl-1,2,4-triazin-6-yl]-5-(trifluoromethyl) phenol; 2-[3-[[(6S or 6R,8aR or 8aS)-1,2,3,5,6,7,8,8a-octahydroindolizin-6-yl]amino]-5-methyl-1,2,4-triazin-6-yl]-5-(trifluoromethyl) phenol and 2-[3-[[(6R or 6S, 8aR or 8aS)-1,2,3,5,6,7,8,8a-octahydroindolizin-6-yl]amino]-5-methyl-1,2,4-triazin-6-yl]-5-(trifluoromethyl) phenol To a solution of aforementioned N-(6-chloro-5-methyl-1,2,4-triazin-3-yl)-indolizidin-6-yl-amine (step A, fraction one) (124 mg, 0.463 mmol, 1.00 eq) and [2-hydroxy-4-(trifluoromethyl)phenyl]boronic acid (138.3 mg, 0.672 mmol, 1.45 eq) in 1,4-dioxane, extra dry (1.8 mL) and water (0.45 mL) was added under argon cesium carbonate (434.6 mg, 1.33 mmol, 2.88 eq) followed by methanesulfonato (2-dicyclohexylphosphino-2',4',6'-tri-i-propyl-1,1'-biphenyl) (2'-amino-1,1'-biphenyl-2-yl) palladium (II) (38.4 mg, 0.045 mmol, 0.098 eq). The reaction mixture was flushed with argon and stirred at 100° C. for one hour. The color changed from dark green dark brown. The reaction mixture was cooled to room temperature and extracted with ~5 mL EtOAc and ~5 mL water. The aqueous layer was back extracted with ~5 mL EtOAc. The organic layers were washed with ~5 mL water and ~5 mL brine. The combined organic layers were dried over sodium sulfate, filtered and concentrated in vacuo. The crude product was adsorbed on ISOLUTE HM-N and purified by flash chromatography (silica gel, 12 g, MeOH in DCM 0 to 5%) to give the desired products in two fractions yellow powders: the first one (56 mg, 31%) and a second one (24 mg, 13%). LCMS (both fractions): m/z 394.3 [M+H]$^+$, ESI pos.

In a separate flask: to a solution of aforementioned (step A, fraction two) N-(6-chloro-5-methyl-1,2,4-triazin-3-yl)-indolizidin-6-yl-amine (80 mg, 0.284 mmol, 1.0 eq) and [2-hydroxy-4-(trifluoromethyl)phenyl]boronic acid (84.8 mg, 0.412 mmol, 1.45 eq) in 1,4-dioxane, extra dry (0.95 mL) and water (0.24 mL) was added under argon cesium carbonate (266.3 mg, 0.817 mmol, 2.88 eq) followed by methanesulfonato (2-dicyclohexylphosphino-2',4',6'-tri-i-propyl-1,1'-biphenyl) (2'-amino-1,1'-biphenyl-2-yl) palladium (II) (23.5 mg, 0.028 mmol, 0.098 eq). The reaction mixture was flushed with argon and stirred at 90° C. for 18 h. The color changed from brown to dark brown. The reaction mixture was cooled to room temperature and extracted with ~5 mL ethyl acetate and ~5 mL water. The aqueous layer was back extracted with ~5 mL ethyl acetate. The organic layers were washed with ~5 mL water and ~5 mL brine. The combined organic layers were dried over sodium sulfate, filtered and concentrated in vacuo. The crude product was purified by flash chromatography (silica gel, 4 g, heptan/MeOH in DCM 0 to 10%) to give the title compounds in two fractions as yellow powders: the first one (37 mg, 33% yield) and a second one (18 mg, 16% yield). LCMS: m/z 394.4 [M+H]$^+$, ESI pos.

In a final stage, the two fractions mention above (37 mg) and (56 mg) were combined and submitted for SFC separation (column chiral O J-H, 5 μm, 250×20 mm; 10% iPrOH+0.2% diethylamine) to afford two new enantiomerically fractions: the first one Example 31 as an off-white powder (30 mg, 51%) and the second fraction Example 32 as a white powder (35 mg, 60%). The relative stereochemistry was not investigated at this stage.

In addition, the two other left fractions mention above (24 mg) and (18 mg) were combined and submitted for RP separation (column: Gemini N X, 12 nm, 5 μM, 100×30 mm; CAN/water+0.1% trimethylamine) to afford 2 additional enantiomerically pure fractions both as white powder Example 34 (8 mg, 13%) and Example 33 (12 mg, 20%). The relative stereochemistry was not investigated at this stage.

Reference Example RE-A: 2-[6-[(1-ethyl-3-piperidyl)amino]-4-methyl-pyridazin-3-yl]-5-(trifluoromethyl) phenol RE-A was synthesized as described in WO20200234715.

Example A'

A compound of formula Ib can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B'

A compound of formula Ib can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |

-continued
|  | Per capsule |
|---|---|
| Lactose | 95.0 mg |
| Talc | 4.5 mg |
| Magnesium stearate | 0.5 mg |
|  | 220.0 mg |
The invention claimed is:
1. A compound represented by:
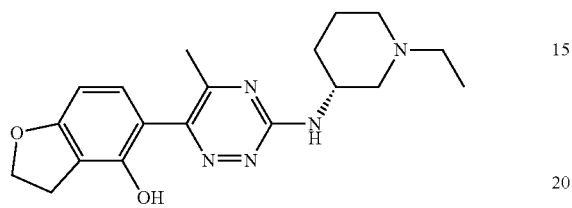
or a pharmaceutically acceptable salt thereof.
2. A pharmaceutical composition comprising the compound according to claim 1 and a therapeutically inert carrier.
* * * * *